United States Patent
Chu et al.

(10) Patent No.: US 8,470,819 B2
(45) Date of Patent: Jun. 25, 2013

(54) BENZIMIDAZOLE AND AZA-BENZIMIDAZOLE CARBOXAMIDES

(75) Inventors: Lin Chu, Scotch Plains, NJ (US); Anthony Ogawa, Mountainside, NJ (US); Hyun O. Ok, Colonia, NJ (US); Feroze Ujjainwalla, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 172 days.

(21) Appl. No.: 13/126,086

(22) PCT Filed: Oct. 26, 2009

(86) PCT No.: PCT/US2009/062034
§ 371 (c)(1),
(2), (4) Date: Apr. 26, 2011

(87) PCT Pub. No.: WO2010/051245
PCT Pub. Date: May 6, 2010

(65) Prior Publication Data
US 2011/0207750 A1      Aug. 25, 2011

Related U.S. Application Data

(60) Provisional application No. 61/198,119, filed on Nov. 3, 2008.

(51) Int. Cl.
| | |
|---|---|
| A61K 31/535 | (2006.01) |
| A61K 31/44 | (2006.01) |
| A61K 31/41 | (2006.01) |
| C07D 403/14 | (2006.01) |
| C07D 413/14 | (2006.01) |
| C07D 249/08 | (2006.01) |
| C07D 271/10 | (2006.01) |
| C07D 417/14 | (2006.01) |
| C07D 401/14 | (2006.01) |

(52) U.S. Cl.
USPC ........ 514/234.5; 514/364; 514/339; 514/383; 514/256; 546/270.1; 546/256; 548/143; 548/266.4; 544/131; 544/333

(58) Field of Classification Search
USPC ..... 546/270.1, 256; 548/143, 266.4; 514/364, 514/339, 383, 234.5, 256; 544/131, 333
See application file for complete search history.

(56) References Cited

U.S. PATENT DOCUMENTS

| | | |
|---|---|---|
| 6,130,235 A | 10/2000 | Mavunkel et al. |
| 2005/0143438 A1 | 6/2005 | Wallace et al. |
| 2005/0267147 A1 | 12/2005 | Poitout et al. |

FOREIGN PATENT DOCUMENTS

| | | |
|---|---|---|
| WO | 95/13064 | 5/1995 |
| WO | 2005/063754 | 7/2005 |

OTHER PUBLICATIONS

International Search Report of PCT/US2009/062034, dated Dec. 23, 2009.
Int'l Preliminary Report on Patentability of PCT/US2009/062034, dated Dec. 13, 2009.
Supp. European Search Report of EP 09824047, dated Jun. 12, 2012.
Database Caplus, Chem. Abstr. XP002677467, Database Accession No. 958567-28-7, dated Dec. 18, 2007.

*Primary Examiner* — Rebecca Anderson
(74) *Attorney, Agent, or Firm* — Carol. S. Quagliato; Catherine D. Fitch

(57) ABSTRACT

This invention provides compounds of Formula I which are PAFR antagonists: I and the pharmaceutically acceptable salts thereof. The compounds are useful for treating PAF-mediated disorders, and can be used in methods for treating atherosclerosis and preventing or reducing risk for atherosclerotic disease events. The compounds are also useful for treating or ameliorating pain, e.g. inflammatory pain and/or nociceptive pain, and for treating or ameliorating autoimmune and/or inflammatory diseases, among other conditions.

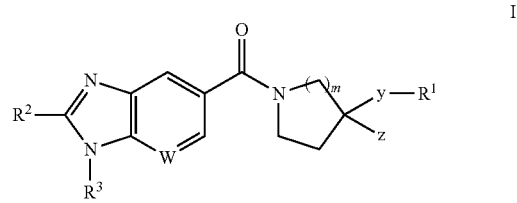

19 Claims, No Drawings

BENZIMIDAZOLE AND AZA-BENZIMIDAZOLE CARBOXAMIDES

TECHNICAL FIELD

This invention relates to amide-substituted benzimidazole and aza-benzimidazole compounds which have platelet activating factor (PAF) receptor antagonist activity, pharmaceutical compositions containing these compounds and methods of treating PAF-mediated disorders, including inflammatory, cardiovascular and immune disorders.

BACKGROUND OF THE INVENTION

Platelet-activating factor (PAF, 1-0-alkyl-2-acetyl-sn-glycerol-3-phosphorylcholine) is a potent inflammatory phospholipid mediator that binds to and activates platelet-activating factor receptor (PAFR). PAF is produced and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. PAF is similar to other lipid mediators such as thromboxane A, prostaglandins, and leukotrienes with respect to the level of potency (active at $10^{-12}$ to $10^{-9}$ M), tissue amount (picomoles) and short plasma half life (2-4 minutes). PAF is physiologically active and causes contraction of the airway smooth muscle, increased vascular permeability, platelet aggregation, and hypotension. Reviewed in: Prescott, S. M. et al. *Annu. Rev. Biochem.* 2000, 69, 419-445; Honda et al. *J. Biochem.* 2002, 131, 773-779; Stafforini et al. *Crit. Rev. Clin. Lab Sci.* 2003, 40, 643-672.

PAF has been reported to participate in several aspects of the inflammatory response associated with the pathogenesis of atheroscloerosis, however, the precise role of PAF/PAFR has not been defined. PAF activates the adhesive interaction of leukocytes with the vascular endothelium and the transmigration of leukocytes, promotes the release of reactive oxygen species and tissue-damaging enzymes from leukocytes and endothelial cells, induces the synthesis of inflammatory cytokines from monocytes, and causes the aggregation and degranulation of platelets. In addition, PAF receptor has been shown to recognize both PAF and PAF-like oxidized phospholipids on LDL and may promote an inflammatory response to them (Frostegard, J. et al., *Arterioscler. Thromb. Vasc. Biol.* 1997, 17, 963-968; Leitinger, N. *Curr. Opin. Lipidol.* 2003, 14, 421-430). A PAFR antagonist was reported to reduce atherosclerotic lesion area by 62% in Ldlr–/– mice fed an atherogenic diet (Subbanagounder, G. et al., *Circ. Res.* 1999, 85, 311-318). PAF may also promote smooth muscle cell proliferation, angiogenesis and elastase release. These activities have the potential to contribute to lesion formation or to the generation of occlusive thrombi at the site of plaque rupture (Reviewed in: Demopoulos, C. A. et al., *Eur. J. Lipid Sci. Technol.* 2003, 105, 705-716; Zimmerman, G. A. et al. *Crit. Care Med.* 2002, 30, S294-S301).

PAF has also been implicated in both peripheral and neuropathic pain responses. PAF can induce hyperalgesia when injected subcutaneously into a rat paw (Bonnet, J. et al., *INSERM* 1981, 100, 111; Vargaftig, B. B.; Ferreira, S. H. *Braz. J. Med. Biol. Res.* 1981, 14, 187) and PAFR antagonists were reported to decrease the inflammatory nociceptive response in rats (Teather, L. A. *Psychopharmacology* 2002, 163, 430-433). PAF may also mediate neuropathic pain responses. Intrathecal administration of PAF in mice caused the development of tactile allodynia and thermal hyperalgesia (Morita, K. et al., *Pain* 2004, 111, 351-359). PAF is expressed in the spinal cord and DRG neurons. A PAFR agonist evoked an intracellular $Ca^{2+}$ flux in capsaicin-sensitive DRG but not in Pafr$^{-/-}$ mice, and it has been proposed that PAF may function in both persistent pain and the sensitization of primary sensory neurons after tissue injury (Tsuda, M. et al., *J. Neurochem.* 2007, 102, 1658-1668).

PAF also appears to play a role in pathological allergic, hypersecretory and additional inflammatory responses. Many published studies suggest the involvement of PAF in autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, inflammatory bowel diseases, edema, rhinitis, thrombosis, bronchitis, urticaria, psoriasis, retinal and corneal diseases, chemically induced liver cirrhosis, and ovimplantation in pregnancy, and acute respiratory distress syndrome. References include: Piper, P. J. et al., *Ann. NY Acad. Sci.* 1991, 629, 112-119; Holtzman, M. J. *Am. Rev. Respir. Dis.* 1991, 143, 188-203; Snyder, F. *Am. J. Physiol. Cell Physiol.* 1990, 259, C697-C708; Prescott, S. M. et al., *J. Biol. Chem.* 1990, 265, 17381-17384; (cardiac diseases) Feuerstein, G. et al., *J Lipid Mediat. Cell Signal.* 1997, 15, 255-284; (liver injury) Karidis, N. P. et al., *World J. Gastroenterol.* 2006, 12, 3695-3706; (pancreatitis) Liu, L. R.; Xia, S. H. *World J. Gastroenterol.* 2006, 12, 539-545; (lung) Uhlig, S. et al., *Pharamcol. Rep.* 2005, 57, 206-221; (thrombosis) Prescott, S. M. et al., *Arterioscler. Thromb. Vasc. Biol.* 2002, 22, 727-733; Ishii, S.; Shimizu, T. *Prog. Lipid Res.* 2000, 39, 41-82. Compounds and/or pharmaceutical compositions which act as PAF receptor antagonists should be of value in the treatment of any of the above conditions.

Despite significant therapeutic advances in the treatment and prevention of atherosclerosis and ensuing atherosclerotic disease events, such as the improvements that have been achieved with HMG-CoA reductase inhibitors, further treatment options are clearly needed. Moreover, there is a need for additional treatment options, in addition to the therapeutics that exist, for the treatment of both inflammatory and neuropathic pain. The instant invention addresses those needs by providing compounds, compositions and methods for the treatment or prevention of atherosclerosis and pain as well as related and other immune conditions.

SUMMARY OF THE INVENTION

The instant invention relates to compounds of Formula I which are PAFR antagonists, methods of their preparation, and methods and pharmaceutical formulations for using these compounds in mammals, especially humans. This invention provides compounds of structural Formula I:

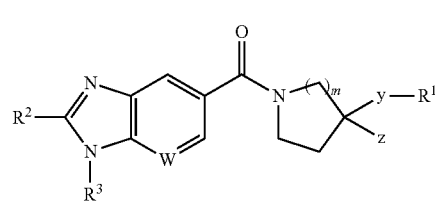

and the pharmaceutically acceptable salts thereof. This invention also involves the use of compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

The compounds of Formula I are also useful as to treat or ameliorate inflammatory pain and nociceptive pain. They are also useful to treat or ameliorate autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, inflammatory bowel diseases, edema, rhinitis, thrombosis, bronchitis, urticaria, psoriasis, retinal and corneal diseases, chemically induced liver cirrhosis, and ovimplantation in pregnancy, and acute respiratory distress syndrome. The instant invention provides methods of treatment comprising administering a therapeutically effective amount of a compound of Formula I to a patient in need of the above-described treatments.

A further object is to provide the use of PAFR inhibitors of Formula I in combination with other therapeutically effective agents, including other drugs useful for the treatment of atherosclerosis and pain. These and other objects will be evident from the description contained herein.

DETAILED DESCRIPTION OF THE INVENTION

The instant invention provides compounds having structural Formula I:

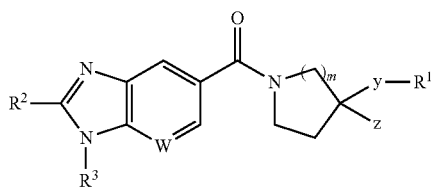

I and the pharmaceutically acceptable salts thereof wherein:

$R^1$ is selected from the group consisting of
(a) 5-membered heterocyclic ring containing 1 to 4 heteroatoms selected from 1 to 4 of N, 0 (zero) to 1 of O, and 0 (zero) to 1 of S, wherein the ring is optionally substituted with $R^4$, and
(b) 6-membered heterocyclic ring containing 1 to 2 of N, wherein the ring is optionally substituted with $R^4$;

$R^2$ is selected from the group consisting of
(a) —$C_{1-6}$alkyl optionally substituted with one or more substituents selected from the group consisting of: (i) fluoro, (ii) hydroxy,
(iii) Hetcy optionally substituted with one or more substituents selected from the group consisting of —F, —OH and methyl, and
(iv) phenyl optionally substituted with one or more substituents selected from the group consisting of —F, —Cl, —OH, —CN, —OC$_{1-4}$alkyl optionally substituted with one or more substituents selected from the group consisting of fluoro and cyano, and $C_{1-4}$alkyl optionally substituted with one or more substituents selected from the group consisting of fluoro, cyano and —OC(O)$C_{1-4}$alkyl,
(b) —$C_{3-6}$cycloalkyl optionally substituted with one or more substituents selected from the group consisting of: (i) fluoro, (ii) hydroxy, and (iii) —$C_{1-4}$alkyl optionally substituted with one or more of fluoro,
(c) —N($C_{1-3}$allyl)$_2$ optionally substituted with one or more substituents selected from the group consisting of fluoro and hydroxy,
(d) phenyl optionally mono- or di-substituted with $R^5$,
(e) Hetcy optionally substituted with one or more substituents selected from the group consisting of fluoro, hydroxy and methyl,
(f) 5-membered heterocyclic ring containing 1 to 4 heteroatoms selected from 1 to 4 of N, 0 (zero) to 1 of O, and 0 (zero) to 1 of S, wherein the ring is optionally mono- or di-substituted with $R^5$, and
(g) 6-membered heterocyclic ring containing 1 to 2 of N, wherein the ring is optionally mono- or di-substituted with $R^5$;

$R^3$ is selected from the group consisting of
(a) —$C_{1-6}$alkyl optionally substituted with one or more substituents selected from the group consisting of: (i) fluoro, (ii) hydroxy, and
(iii) phenyl optionally substituted with one or more substituents selected from the group consisting of —F, —Cl, —CN, —OH, —OMe, —OC(O)$C_{1-4}$alkyl, —CF$_3$ and —OCF$_3$,
(b) —$C_{3-6}$cycloalkyl optionally substituted with one or more substituents selected from the group consisting of: (i) fluoro, (ii) hydroxy,
(iii) —$C_{1-4}$alkyl optionally substituted with one or more of fluoro, and
(iv) —OC$_{1-4}$allyl optionally substituted with one or more of fluoro,
(c) phenyl optionally mono- or di-substituted with $R^5$, and
(d) 6-membered heterocyclic ring containing 1 to 2 of N, wherein the ring is optionally mono- or di-substituted with $R^5$;

$R^4$ is selected independently at each occurrence from the group consisting of (a) —F, (b) —Cl, (c) hydroxy, (d) cyano, (e) oxo, (f) amino, (g) —$C_{1-6}$alkyl optionally substituted with one or more of fluoro, (h) —$C_{3-6}$cycloalkyl optionally substituted with one or more of fluoro, and (i) —OC$_{1-6}$alkyl optionally substituted with one or more of fluoro;

$R^5$ is selected independently at each occurrence from the group consisting of (a) —F, (b) —Cl, (c) —OH, (d) —OC(O)$C_{1-4}$alkyl, (e) —NR$^a$R$^b$, (f) —CN, (g) —$C_{1-4}$alkyl optionally substituted with one or more of fluoro and (h) —OC$_{1-4}$alkyl optionally substituted with one or more of fluoro;

$R^a$ and $R^b$ are independently selected from the group consisting of (a) hydrogen, (b) —$C_{1-4}$alkyl optionally substituted with one or more substituents selected from the group consisting of (i) fluoro, (ii) hydroxy and (iii) phenyl optionally substituted with one or more substituents selected from the group consisting of —F, —Cl, —OCH$_3$, —CF$_3$ and —OCF$_3$, and (c) —$C_{3-6}$cycloalkyl optionally substituted with one or more substituents selected from the group consisting of fluoro, hydroxy and —$C_{1-4}$allyl;

or $R^a$ and $R^b$ together with the nitrogen to which they are both attached represent azetidinyl, pyrrolidinyl, piperidinyl, piperazinyl or morpholinyl, each optionally substituted with one or more substituents selected from —OH and —F;

m is an integer selected from 1 and 2;

W is selected from N and CH;

y is selected from a bond and —$CR^{6a}R^{6b}$—;

z is selected from the group consisting of hydrogen, fluoro, hydroxy, and —$C_{1-4}$alkyl optionally substituted with one or more of —OH and —F;

$R^{6a}$ and $R^{6b}$ are independently selected from the group consisting of (a) —H, (b) hydroxy, (e) —$C_{1-4}$alkyl optionally substituted with one or more of fluoro, (d) —$OC_{1-4}$alkyl optionally substituted with one or more of fluoro and (e) —$OC(O)C_{1-4}$alkyl;

or $R^{6a}$ and $R^{6b}$ are joined together with the carbon to which they are both attached to form a $C_{3-6}$cycloalk-diyl ring, for example cyclopropyl-1,1-diyl; and Hetcy is selected from the group consisting of azetidinyl, pyrrolidinyl, piperidinyl, piperidinyl and morpholinyl.

In an embodiment of this invention are compounds of Formula I wherein m is one. In another embodiment are compounds wherein m is two. In another embodiment are compounds of Formula I wherein y is a bond, that is, wherein y represents a bond that directly connects $R^1$ to the pyrrolidinyl or piperidinyl ring shown in the Formula I structure. In another embodiment are compounds of Formula I wherein y is —$CR^{6a}R^{6b}$—, and in a class thereof y is —$CH_2$—. Preferably, y is a bond.

In a further embodiment of this invention are compounds of Formula I having the structural Formula Ia:

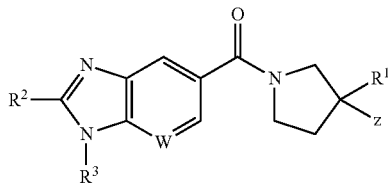

Ia and pharmaceutically acceptable salts thereof, wherein the variable substituents (e.g., $R^1$, $R^2$, $R^3$, W, z, etc.), are as defined in Formula I.

In another embodiment of this invention are compounds of Formula I or Ia having the structural Formula Ib:

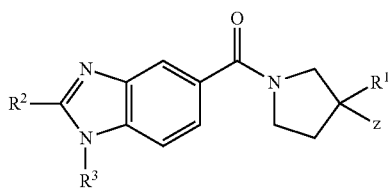

Ib and pharmaceutically acceptable salts thereof, wherein the variable substituents (e.g., $R^1$, $R^2$, $R^3$, z, etc.), are as defined in Formula I.

In another embodiment of this invention are compounds of Formula I, Ia, or Ib having the structural Formula Ic:

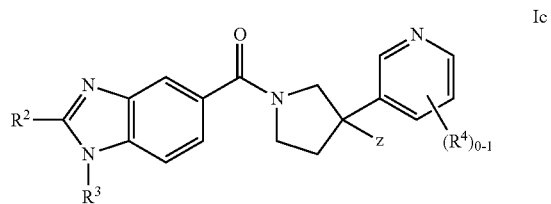

Ic and pharmaceutically acceptable salts thereof, wherein the variable substituents (e.g., $R^1$, $R^2$, $R^3$, $R^4$, z, etc.), are as defined in relation to Formula I.

In another embodiment of this invention are compounds of Formula I or Ia, wherein W is CH. In yet another embodiment of the present invention are compounds of Formula I or Ia wherein W is N.

In another embodiment of this invention are compounds of Formula I, Ia or Ib, wherein $R^1$ is selected from the group consisting of pyridyl, pyrimidinyl, oxadiazolyl, tetrazolyl, triazolyl, pyrazolyl, thiazolyl, and isoxazolyl, each of which is optionally substituted with $R^4$. Examples of suitable $R^1$ groups include, but are not limited to,

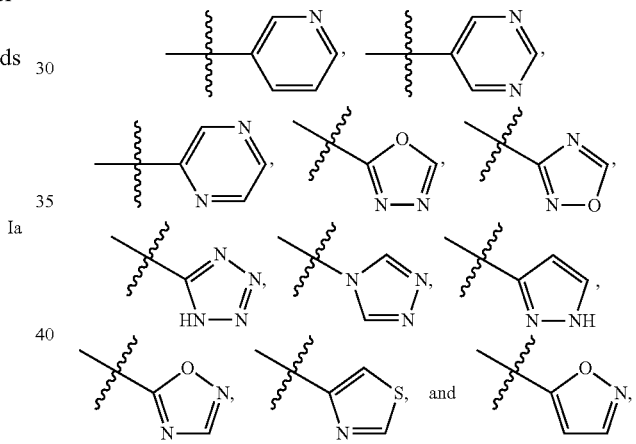

each of which is optionally substituted with $R^4$. Each optional $R^4$ substituent may be attached to the $R^1$ five-membered heterocyclic ring via any suitable carbon or nitrogen or to the $R^1$ six-membered heterocyclic ring via any suitable carbon.

In another embodiment of this invention are compounds of Formula I, Ia, Ib or Ic wherein $R^4$, when present, is independently selected at each occurrence from the group consisting of fluoro, chloro, hydroxy, oxo, methyl, —$CF_3$, methoxy, ethoxy and cyano. In a class thereof, $R^4$ is fluoro, hydroxy, oxo, methyl, methoxy or ethoxy or is absent. In a preferable sub-class thereof, $R^4$ is absent (i.e., $R^1$ is unsubstituted).

In another embodiment of this invention are compounds of Formula I, Ia, or Ib wherein $R^1$ is selected from pyridyl and oxadiazolyl, each optionally substituted with $R^4$, and particularly wherein each is mono-substituted with $R^4$. In a class of compounds of Formula I, Ia, Ib or Ic wherein $R^1$ is pyridyl, $R^4$ is preferably selected from fluoro, methyl, methoxy, and ethoxy. In an alternate class of compounds of Formula I, Ia, or Ib wherein $R^1$ is oxadiazolyl, $R^4$ is preferably selected from methyl, methoxy and ethoxy. In a sub-class, $R^1$ is unsubstituted pyridyl; pyridyl mono-substituted with methyl, methoxy, ethoxy or fluoro; or oxadiazolyl mono-substituted with methyl. In a preferable sub-class, $R^1$ is unsubstituted pyridyl.

In another embodiment of this invention are compounds of Formulas I, Ia, Ib, or Ic wherein Hetcy, when present, is selected from optionally substituted pyrrolidinyl, piperidinyl, and morpholinyl. In a class thereof, when $R^2$ is Hetcy, Hetcy is optionally substituted pyrrolidinyl, piperidinyl or morpholinyl bonded to the imidazole ring via a nitrogen in Hetcy.

In a further embodiment of this invention are compounds of Formula I, Ia, Ib or Ic wherein $R^3$ is selected from —$C_{1-4}$alkyl optionally substituted with phenyl, wherein the phenyl is optionally substituted with 1 to 2 substituents selected from the group consisting of —F, —Cl and —$OCF_3$; —$C_{3-6}$cycloalkyl optionally substituted with methyl; pyridinyl optionally mono- or di-substituted with $R^5$; and phenyl optionally mono- or di-substituted with $R^5$. In a class thereof, $R^3$ is selected from isopropyl; tert-butyl; cyclobutyl; cyclopropyl optionally substituted with methyl; and phenyl optionally mono- or di-substituted with $R^5$.

In yet another embodiment of this invention are compounds of Formula I, Ia, Ib, or Ic wherein $R^2$ is selected from optionally substituted —$C_{1-4}$alkyl, and more particularly optionally substituted with phenyl; optionally substituted —$C_{3-6}$cycloalkyl, and more particularly optionally substituted with methyl; optionally substituted Hetcy, and more particularly optionally substituted with hydroxy; and phenyl optionally mono- or di-substituted with $R^5$. In a class thereof, $R^2$ is isopropyl; branched butyl e.g., tert-butyl or 1-methylpropyl; cyclopropyl optionally substituted with methyl; cyclobutyl optionally substituted with methyl; morpholinyl; pyrrolidinyl optionally mono- or di-substituted with fluoro; piperidinyl optionally substituted with hydroxy or fluoro; or phenyl optionally mono- or di-substituted with $R^5$.

In another embodiment of the invention are compounds of Formula I, Ia, Ib or Ic wherein when one of $R^2$ and $R^3$ contains an aromatic or partially unsaturated moiety bonded directly to the imidazole ring, the other of $R^2$ and $R^3$ contains a saturated moiety bonded directly to the imidazole ring, and wherein the $R^2$ and $R^3$ moieties are optionally substituted as defined in Formula I. In other words, when $R^2$ is phenyl, a 5-membered heterocycle or a 6-membered heterocycle, then $R^3$ is selected from the group consisting of —$C_{1-6}$alkyl and —$C_{3-6}$cycloalkyl; and when. $R^3$ is phenyl or a 6-membered heterocycle, then $R^2$ is selected from the group consisting of —$C_{1-6}$alkyl, —$C_{3-6}$cycloalkyl, —$N(C_{1-3}$alkyl$)_2$ and Hetcy; and wherein $R^2$ and $R^3$ are each optionally substituted. In a class thereof, when $R^2$ is optionally substituted phenyl or an optionally substituted 5- or 6-membered heterocycle, $R^3$ is preferably —$C_{1-6}$alkyl or —$C_{3-6}$cycloalkyl, each of which is optionally substituted, and more preferably $R^3$ isopropyl. In an alternate class thereof, when $R^2$ is —$C_{1-6}$alkyl, —$C_{3-6}$cycloalkyl, —$N(C_{1-3}$alkyl$)_2$ or Hetcy, each of which is optionally substituted, $R^3$ is preferably optionally substituted phenyl or an optionally substituted 6-membered heterocycle, and more preferably $R^3$ is substituted phenyl.

In another embodiment of this invention are compounds of Formula I, Ia, Ib or Ic wherein $R^5$, when present, is independently selected at each occurrence from —F, —Cl, -Me, —OMe, —OEt, —$CF_3$ and —$OCF_3$. Preferably, $R^5$ is —$OCF_3$.

In another embodiment of this invention are compounds of Formula I, Ia, Ib or Ic wherein z is —H or hydroxy. In a preferable class, z is —H.

Each embodiment, class or sub-class described above for each variable (i.e., $R^1$, $R^2$, $R^3$, $R^4$, $R^5$, $R^{6a}$, $R^{6b}$, m, W, y, z and Hetcy) in Formula I, Ia, Ib or Ic, may be combined with one or more of the embodiments, classes or sub-classes described above for one or more other variables, and all such sub-generic combinations are included within the scope of this invention. A non-limiting example of a sub-generic combination encompassed herein are compounds of any of Formulas I, Ia, Ib or Ic wherein:

$R^1$ is optionally substituted with $R^4$ and is selected from the group consisting of pyridyl, pyrimidinyl, oxadiazolyl, tetrazolyl, triazolyl, pyrazolyl, thiazolyl, and isoxazolyl; and particularly $R^1$ is selected from a) unsubstituted pyridyl, b) pyridyl mono-substituted with methyl, methoxy, ethoxy or fluoro, and c) oxadiazolyl mono-substituted with methyl;

z is selected from —H and hydroxy;

$R^2$ is selected from a) —$C_{1-4}$alkyl optionally substituted with phenyl, b) —$C_{3-6}$cycloalkyl optionally substituted with methyl, c) Hetcy optionally substituted with hydroxy and d) phenyl optionally mono- or di-substituted with $R^5$; and particularly $R^2$ is selected from a) isopropyl, b) branched butyl, c) cyclopropyl optionally substituted with methyl, d) cyclobutyl optionally substituted with methyl, e) morpholinyl, f) pyrrolidinyl optionally mono- or di-substituted with fluoro, g) piperidinyl optionally substituted with hydroxy or fluoro, and h) phenyl optionally mono- or di-substituted with $R^5$;

$R^3$ is selected from a) —$C_{1-4}$alkyl optionally substituted with phenyl, wherein the phenyl is optionally substituted with 1 to 2 substituents selected from the group consisting of —F, —Cl and —$OCF_3$, b) —$C_{3-6}$cycloalkyl optionally substituted with methyl, c) pyridinyl optionally mono- or di-substituted with $R^5$ and d) phenyl optionally mono- or di-substituted with $R^5$; and particularly $R^3$ is selected from a) isopropyl, b) tert-butyl, c) cyclobutyl, d) cyclopropyl optionally substituted with methyl and e) phenyl optionally mono- or di-substituted with $R^5$.

As used herein, the term "alkyl" means carbon chains which may be linear or branched, or combinations thereof, containing the indicated number of carbon atoms. Examples of alkyl groups include methyl (Me), ethyl (Et), propyl, isopropyl (i-propyl, $^i$Pr), butyl, sec- and tert-butyl (s-butyl, t-butyl, $^s$Bu, $^t$Bu), pentyl, hexyl, and the like. "Cycloalkyl" is intended to be a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule. Preferably, cycloalkyl is cyclopropyl or cyclobutyl, and more particularly, when it is substituted with —$CH_3$ or —$CF_3$, the substituent is on the ring carbon which serves as the point of attachment to the rest of the molecule.

"Halogen" (Halo) includes fluoro, chloro, bromo and iodo. Preferred halogens are —F and —Cl, more preferably —F.

As used herein, "heterocyclic ring" and "heterocycle" mean an aromatic or partially unsaturated heterocyclic ring containing one or more carbon atoms and one or more heteroatoms selected from nitrogen (N), oxygen (O) and sulfur (S), in total containing 5 to 6 atoms in the ring. A heterocyclic ring may be more specifically defined where appropriate in the specification, for example with respect to the number of members (i.e. atoms) in the ring and/or the type and quantity of heteroatoms in the ring. Examples of aromatic or partially unsaturated heterocyclic rings include but are not limited to pyridyl, pyrimidyl, imidazolyl, tetrazolyl, triazolyl, pyrazolyl, thiazolyl, isoxazolyl, and the like. For 5-membered aromatic or partially unsaturated heterocyclic rings, the point of attachment in a compound structure may be via any available carbon or nitrogen in the ring which results in the creation of a stable structure, unless specified otherwise. For 6-membered aromatic or partially unsaturated heterocyclic rings, the point of attachment in a compound structure may be via any available carbon in the ring which results in the creation of a stable structure, unless specified otherwise. The heterocyclic ring may be substituted on any available carbon or nitrogen in the ring which results in the creation of a stable structure.

The term "Hetcy" is meant to encompass the specific definition provided within Formula I. The point of attachment of Hetcy to a compound of structural Formula I is via the nitrogen in the Hetcy ring.

The phrases "optionally substituted" and "optionally substituted with one or more substituents" are both intended to mean that the total number of substituents on the optionally substituted moiety overall may be zero, one or more than one, and that each carbon and heteroatom (when present) available for substitution in the given moiety may independently be unsubstituted or mono- or poly-substituted, with one or more substituents that are the same or different at each occurrence and which result in the creation of a stable structure as is understood to be reasonable by one skilled in the art. In some instances the number of substituents which may optionally be present on a moiety is specified, for example but not limited to, 1 to 3 of fluoro and mono- or di-substituted with $R^5$. For example, $C_{1-3}$alkyl optionally substituted with fluoro includes, but is not limited to, —$CH_3$, —$CH_2F$, —$CHF_2$, —$CF_3$, —$CH_2CH_3$, —$CH_2$—$CH_2F$, —CHF—$CH_2F$, —$CF_2$—$CF_3$, —$CH(CF_3)$—$CH_3$, —$CF_2$—$CF_2$—$CF_3$, and the like; methyl optionally substituted with 1 to 3 of fluoro includes —$CH_3$, —$CH_2F$, —$CHF_2$ and —$CF_3$; and phenyl optionally mono- or di-substituted with $R^5$ includes

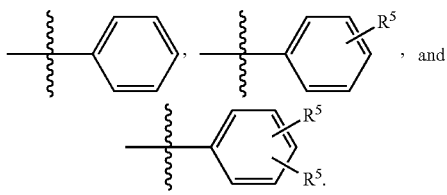

Some of the compounds encompassed herein may exist as tautomers, e.g., keto-enol tautomers. For the purpose of illustration, when $R^1$ is a 5-membered heteroaryl ring and $R^4$ is oxo or —OH, the resulting compound may be capable of tautomerism, as exemplified below:

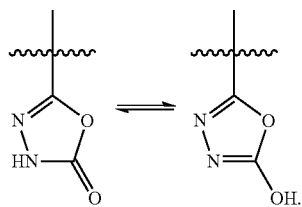 [SMILES: *c1n[nH]c(=O)o1 ; *c1nnc(O)o1]

Other nitrogen-containing 5-member heterocycles can also exist as tautomers. Examples include but are not limited to:

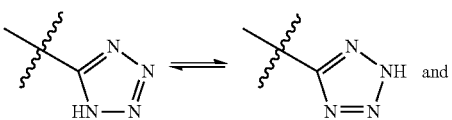

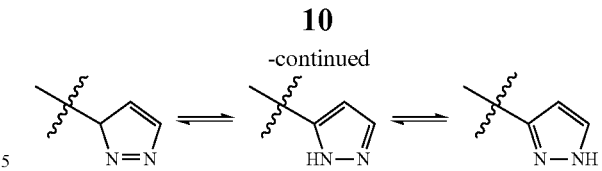

Where compounds of this invention are capable of tautomerization, all individual tautomers as well as mixtures thereof are included in the scope of this invention.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

Reference to the compounds of this invention as those of "Formula I," "Formula Ia," "Formula Ib," "Formula Ic" or any other generic structural formula or specific compound described or claimed herein is intended to encompass the specific compound or compounds falling within the scope of the generic structural formula including salts thereof, particularly pharmaceutically acceptable salts, as well as the esters and/or solvates of such compounds and salts thereof, where such forms are possible unless specified otherwise. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like, and particularly citric, fumaric, hydrobromic, hydrochloric, trifluoroacetic, maleic, phosphoric, sulfuric, and tartaric acids.

Any pharmaceutically acceptable pro-drug modification which results in conversion in vivo to an active form of a compound within the scope of this invention is also within the scope of this invention. For example, esters can optionally be made by esterification of an available carboxylic acid group or by formation of an ester on an available hydroxy group in a compound. Pharmaceutically acceptable esters of the compounds of this invention may serve as pro-drugs which can be hydrolyzed back to their acid or hydroxy fox in particularly in vivo and as such are encompassed within the scope of this invention. Examples of pharmaceutically acceptable esters include, but are not limited to, —$C_{1-4}$alkyl and —$C_{1-4}$alkyl substituted with phenyl.

The compounds of Formula I may contain one or more asymmetric centers, and can thus occur as racemates, racemic mixtures, single enantiomers, diastereoisomeric mixtures and individual diastereoisomers. The present invention includes all such isomers, as well as salts, esters and/or solvates of such racemates, mixtures, enantiomers and diastereoisomers. Compounds of structural Formula I may be separated into their individual diastereoisomers by, e.g., fractional crystallization from suitable solvents, e.g., DCM/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, synthesis can be performed using one or more chiral intermediates which results in a chiral final product.

Furthermore, compounds of the present invention may exist in amorphous or crystalline physical forms, and a single compound may exist in more than one polymorphic crystalline form. All such physical forms are intended to be included in the scope of the present invention. In addition, some of the compounds of the instant invention may form solvates with water (hydrates) or with common organic solvents. Such solvates and hydrates are likewise encompassed within the scope of this invention.

Accordingly, the compounds within the generic structural formulas and specific compounds described and claimed herein encompass salts thereof, esters thereof, and salts of esters thereof where such forms are possible unless specified otherwise. The instant invention further encompasses all possible stereoisomers, physical forms (e.g., amorphous and crystalline forms), solvate forms, tautomers and combinations of these forms of the compounds falling within the generic structural formulas as well as the specific compounds described and claimed herein, the salts thereof, esters thereof, and salts of esters thereof, where such forms are possible unless specified otherwise.

This invention also involves the use of the PAF receptor antagonist compounds described herein to slow or halt atherogenesis. Therefore, one object of the instant invention is to provide a method for treating atherosclerosis, which includes halting or slowing the progression of atherosclerotic disease once it has become clinically evident, comprising administering a therapeutically effective amount of a compound of Formula I to a patient in need of such treatment. Another object is to provide methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of Formula I of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may already have atherosclerotic disease at the time of administration, or may be at risk for developing it.

This invention also involves the use of compounds of Formula I described herein to treat or ameliorate inflammatory pain and nociceptive pain in mammals, and especially in humans. Therefore, one object of the instant invention is to provide a method for treating pain, comprising administering a therapeutically effective amount of a compound of Formula I to a patient in need of such treatment. Another object is to provide methods for preventing or reducing the risk of developing inflammatory and nociceptive pain, comprising administering a prophylactically effective amount of a compound of Formula I to a patient who is at risk of developing inflammatory or nociceptive pain.

Compounds and/or pharmaceutical compositions which act as PAF receptor antagonists appear to play a role in pathological allergic, hypersecretory and inflammatory responses. Many published studies suggest the involvement of PAF in autoimmune and inflammatory human diseases, including anaphylaxis, rheumatoid arthritis, acute inflammation, asthma, endotoxic shock, ischemia, gastrointestinal ulceration, transplanted organ rejection, reperfusion injury, myocardial infarction, inflammatory bowel diseases, pain, edema, rhinitis, thrombosis, bronchitis, urticaria, psoriasis, retinal and corneal diseases, chemically induced liver cirrhosis, and ovimplantation in pregnancy, and acute respiratory distress syndrome. Accordingly, another object of the instant invention is to provide a method for treating a PAF receptor mediated medical condition, particularly a pathological allergic, hypersecretory and/or inflammatory condition including those conditions described above, comprising administering a therapeutically effective amount of a compound of Formula I to a patient in need of such treatment.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment atherosclerosis or pain, and a prophylactically effective amount, e.g., for prevention of an atherosclerotic disease event or inflammatory or neuropathic pain.

In general, PAFR antagonists can be identified as those compounds which have an $IC_{50}$ in the "PAF Binding Assay" that is less than or equal to about 1 µM, and preferably 200 nM or less, and most preferably 40 nM or less.

An effective amount of a PAFR antagonist in the method of this invention is in the range of about 0.1 mg/kg to about 100 mg/kg of body weight per day, preferably 0.1 mg to about 30 mg per kg, in single or divided doses. A single daily dose is preferred but not necessary. For an average body weight of 70 kg, the dosage level is therefore from about 7 mg to about 2000 mg of drug dosed one to four times per day, e.g. 10 mg, 25 mg, 50 mg, 75 mg, 100 mg, 125 mg, 150 mg, 175 mg, 200 mg, 250 mg, 500 mg, 1000 mg, 1500 mg, or 2000 mg per dose, preferably given as a single daily dose or in divided doses two to four times a day, or in sustained release form. It will be understood, however, that the specific dose level for any particular patient will depend upon a variety of factors including the age, body weight, general health, sex, diet, time of administration, route of administration, rate of excretion, drug combination and the severity of the patient's condition. A consideration of these factors is well within the purview of the ordinarily skilled clinician for the purpose of determining the therapeutically effective or prophylactically effective dosage amount needed to prevent, counter, or arrest the progress of the condition. It is expected that the PAFR antagonist will administered chronically on a daily basis for a length of time appropriate to treat or prevent the medical condition relevant to the patient, including a course of therapy lasting months, years or the life of the patient.

A therapeutically effective amount of a compound of this invention can be used for the preparation of a medicament useful for treating or preventing any of the medical conditions described herein, in dosage amounts described herein. For example, a compound of this invention can be used for the preparation of a medicament useful for preventing or reducing the risk of developing atherosclerotic disease, halting or slowing the progression of atherosclerotic disease once it has become clinically manifest, and/or preventing or reducing the risk of a first or subsequent occurrence of an atherosclerotic disease event. A compound of this invention can also be used for the preparation of a medicament useful for treating pain. Additionally, a compound of this invention can be used for the preparation of a medicament useful for the treatment of a pathological allergic, hypersecretory and/or inflammatory condition including such conditions described herein. The medicament comprised of a compound of this invention may also be prepared with one or more additional active agents, such as those described below.

One or more additional active agents may be administered with a compound of Formula I. The term "additional active agent (or agents)" is intended to mean a pharmaceutically active agent (or agents) different from the compound of Formula I. In a broad embodiment, any suitable additional active agent or agents, including but not limited to anti-atherosclerotic agents such as a lipid modifying compound, anti-diabetic agents and/or anti-obesity agents, and additional pain-reducing agents may be used in any combination with the compound of Formula I in a single dosage formulation, or may be administered to the patient in one or more separate dosage formulations, which allows for concurrent or sequential administration of the active agents. The additional active agent or agents may have more than one pharmaceutical activity, for example it may have both lipid-modifying effects and anti-diabetic activity. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (MEVACOR® see U.S. Pat. No. 4,342,767), simvastatin (ZOCOR® see U.S. Pat. No. 4,444,784), pravastatin, particularly the sodium salt thereof (PRAVACHOL® see U.S. Pat. No. 4,346,227), fluvastatin particularly the sodium salt thereof (LESCOL® see U.S. Pat. No. 5,354,772), atorvastatin, particularly the calcium salt thereof (LIPITOR® see U.S. Pat. No. 5,273,995), pitavastatin also referred to as NK-104 (see PCT international publication number WO 97/23200) and rosuvastatin (CRESTOR®; see U.S. Pat. No. 5,260,440); cholesterol absorption inhibitors (CM), for example ezetimibe (ZETIA®) or a combination of a CAI with a statin such as ezetimibe with simvastatin (VYTORIN®) or with atorvastatin; 5-lipoxygenase inhibitors; cholesterol ester transfer protein (CETP) inhibitors, for example anacetrapib or JTT-705; HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABCA1 gene expression; FXR and LXR ligands including both inhibitors and agonists; and bisphosphonate compounds such as alendronate sodium. Anti-obesity agents can be employed in combination with a compound of this invention including, but not limited to, sibutramine, orlistat, topiramate, naltrexone, bupriopion, phentermine, and phentermine/topiramate combination (QNEXA®); NPY5 antagonists; Acetyl-CoA Carboxylase-1 and -2 (ACC) inhibitors; MCH1R antagonists; and CB1 antagonists/inverse agonists such as those described in WO03/077847 and WO05/000809. Additional anti-diabetes agents which may be employed in combination with a compound of this invention include but are not limited to DPP-4 (dipeptidylpeptidase-4) inhibitors such as sitagliptin (JANUVIA®, JANUMET®) and vildagliptin (GALVUS®); sulfonylureas e.g., chlorpropamide, tolazamide, glyburide, glipizide, and glimepiride; biguanides, e.g., metformin; alpha-glucosidase inhibitors e.g., acarbose and miglitol; meglitinides e.g., repaglinide; glucagon-receptor antagonists; and glucokinase activators. Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, and the calcium antagonists nifedipine, diltiazem, nitrendipine, verapamil, nimodipine, felodipine, etc. Compounds of this invention can be used in combination with orally inhaled corticosteroids, such as beclomethasone (e.g. QVAR® Inhalation Aerosol), budesonide (e.g. Pulmicort Respules), flunisolide (e.g., AEROBID® and AEROBID®-M Inhaler System), fluticasone (e.g., FLOVENT® DISKUS® inhalation powder, FLOVENT® HFA Inhalation Aerosol), mometasone (e.g., ASMANEX® TWISTHALER®), and triamcinolone (e.g., AZMACORT® Inhalation Aerosol), and also with inhaled corticosteroid/LABA products such as fluticasone propionate/salmeterol (e.g., ADVAIR DISKUS®); corticosteroids such as hydrocortisone, methylprednisolone, betamethasone, dexamethasone, beclomethasone, and the like; with leukotriene receptor antagonists such as montelukast (e.g., SINGULAIR®); phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-phenylalanine-2-(diethylamino)ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Still other types of agent that can be used in combination with the compounds of this invention for the treatment of pain are non-steroidal anti-inflammatory drugs (NSAIDs), for example aspirin, ibuprofen, ketoprofen, and naproxen; non-opioid analgesics such as acetaminophen; and cyclooxygenase-2 (COX-2) inhibitors such as etoricoxib (ARCOXIA®) and celecoxib (CELEBREX®).

In the method of treatment of this invention, the PAFR antagonists may be administered via any suitable route of administration such as orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred.

For oral use, the pharmaceutical compositions of this invention containing the active ingredient may be in forms such as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed. One example of a time-controlled release device is described in U.S. Pat. No. 5,366,738. They may also be coated by the technique described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients.

The compounds of structural Formula I of the present invention can be prepared according to the procedures of the following Schemes and Examples, using appropriate materials and are further exemplified by the specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. All temperatures are degrees Celsius unless otherwise noted. Mass spectra (MS) were measured by electron-spray ion-mass spectroscopy (ES-MS).

The instant compounds are generally isolated in a pharmaceutically acceptable form which can either be the free base or an appropriate salt derivative, such as those described above. The free amine bases corresponding to the isolated salts can be generated by neutralization with a suitable base, such as aqueous sodium hydrogencarbonate, sodium carbonate, sodium hydroxide, or potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization.

Some abbreviations used herein are as follows: ABCA1 is adenosyltriphosphate-binding cassette-family A1; Ac is acetyl; AcOH is acetic acid; AIBN is 2,2'-azobis(2-methylpropionitrile); aq. is aqueous; Ar is Aryl; Atm. is atmospheric pressure units; Bn is benzyl; Boc is tertbutylcarbamoyl; br is broad; Bu is butyl; $^c$Bu is cyclobutyl; $^i$Bu is isobutyl; $^t$Bu is tert-butyl; celite is Celite® diatomaceous earth; conc. is concentrated; cpm is counts per minute; δ is chemical shift; d is doublet; DAST is diethylaminosulfur trifluoride; DBU is 1,8-diazabicyclo[5.4.0]undec-7-ene; DCE is 1,2-dichloroethane; DCM is dichloromethane; d is doublet; DEAD is diethylazodicarboxylate; DIAD is diisopropylazodicarboxylate; DIBAL-H is diisobutylaluminum hydride; DIPEA is diisopropylethylamine; DMAP is 4-dimethylaminopyridine; DME is 1,2-dimethoxyethane; DMF is N,N-dimethylformamide; dppf is 1,1'-bis(diphenylphosphino)ferrocene; DMSO is dimethyl sulfoxide; dppf is 1,1'-Bis(diphenylphosphino)ferrocene; EDC is N-(3-dimethylaminopropyl)-N'-ethylcarbodiimide hydrochloride; EDTA is ethylendiamine tetraacetic acid; equiv. is equivalent(s); ES-MS is electrospray ion-mass spectroscopy; Et is ethyl; Et$_2$O is diethyl ether; EtOH is ethanol, EtOAc is ethyl acetate; FXR is farnesoid X receptor; g is gram; h is hours; HATU is O-(7-azabenzotriazol-1-yl)-N,N,N',N'-tetramethyluronium hexafluorophosphate; HetAr or HAR is Heteroaryl; HMG-CoA is 3-hydroxy-3-methylglutaryl coenzyme A; $^1$H NMR is proton nuclear magnetic resonance; HOAt is 1-hydroxy-7-azabenzotriazole; HOBt is 1-hydroxybenzotriazole; HPLC is high performance liquid chromatography; Hz is hertz; i is Iso; IC$_{50}$ is concentration at which 50% inhibition exists; J is internuclear coupling constant; kg is kilogram; LDA is lithium diisopropylamide; LG is leaving group; LHMDS is lithium bis(trimethylsilyl)amide; LTB$_4$ is leukotriene B$_4$; LXR is liver X receptor; m is multiplet; M is molar; Me is methyl; m.p. is melting point; mg is milligram; μg is microgram; MeCN is acetonitrile; MeOH is methanol; MHz is megahertz; mM is minute; mL is milliliter; mm is millimeter; μL is microliter; mM is milimolar; μM is micromolar; mmol is milimoles; Ms is methanesulfonyl; MS is mass spectrum, and a mass spectrum obtained by ES-MS may be denoted herein by "ES"; m/z is mass to charge ratio; n is normal; N is normal; NaHMDS is sodium bis(trimethylsilyl)amide; NBS is N-bromosuccinimide; NIS is N-iodosuccinimide; nm is nanometer; nM is nanomolar; NMM is N-methylmorpholine; NMO is N-methylmorpholine-N-oxide; NMP is N-methylpyrrolidin-2-one; Pr is propyl; $^c$Pr is cyclopropyl; $^i$Pr is isopropyl; $^n$Pr is n-propyl; $^i$PrOH is isopropyl alcohol; p is pentet; p is para; PEG is polyethylene glycol; Ph is phenyl; Phth is phthalimidoyl; PPARα is peroxisome proliferator activated receptor alpha; p-TSA is para-toluenesulfonic acid; PyBOP is benzotriazole-1-yl-oxy-tris-pyrrolidino-phosphonium hexafluorophosphate; q is quartet; rt is room temperature; s is singlet; satd. is saturated; sec is secondary; t is triplet; $^t$BuOH is tert-butanol; tert is tertiary; Tf is trifluoromethanesulfonyl; TFA is trifluoroacetic acid; and THF is tetrahydrofuran; TMS is trimethylsilyl; Ts is tosyl; UV is ultraviolet; wt is weight; wt. % is weight percent; w/v is weight/volume ratio; xg is times gravity; ° C. is degrees Celsius.

In the Schemes, all substituents are as defined above unless indicated otherwise. Reaction schemes A-M illustrate the methods employed in the synthesis of the compounds of the present invention of structural Formula I. All abbreviations are as defined above unless indicated otherwise.

Reaction scheme A illustrates a general method for the synthesis of compounds of type 8. In this method, an aryl fluoride of type 1 is treated with an amine of type 2 in a nucleophilic aromatic substitution reaction. Preferred conditions for effecting such a nucleophilic displacement of an activated aryl fluoride include the addition of a base, such as potassium carbonate or cesium carbonate, typically in an inert solvent, such as DMSO at temperatures between 100° C. and the boiling point of the reaction mixture. In addition, the reaction may be accelerated by the use of a microwave reactor. The product of the reaction is a nitroaniline of type 3 that can be converted to the corresponding diaminobenzene derivative of type 4. The reaction is usually conducted in the presence of a suitable palladium-on-carbon catalyst, at atmospheric pressure of hydrogen, in an inert solvent, such as EtOH or EtOAc, or combinations thereof, at room temperature. Intermediates of type 4 are acylated with an acid chloride derivative of type 5, often generated from the respective carboxylic acid precursor using methods know to those skilled in the art of organic synthesis, in the presence of a suitable base, such as triethylamine, in an inert solvent such as DCM or THF, most generally at temperatures between −20° C. and room temperature. The product of the reaction is an acetamide of type 6 that can be cyclized to the desired benzimidazole product 7, commonly in the presence of a protic acid, such as glacial acetic acid, trifluoroacetic acid, polyphosphoric acid, or the like, at elevated temperatures ranging from approximately 70° C. to the boiling point of the reaction mixture. The reaction can be accelerated by the use of a microwave reactor, wherein solvents, such as THF, can be superheated to reaction temperatures up to 150° C. When X═—CN, the benzimidazole product of type 7 is then hydrolyzed to a carboxylic acid of type 8 in the presence of a suitable base, such as concentrated sodium hydroxide, commonly in the presence of a suitable co-solvent, such as dioxane, at the boiling temperature of the reaction mixture. The above hydrolysis can be accelerated by the use of a microwave reactor, which permits superheating of reaction mixtures. Alternatively, for a benzimidazole of type 7 wherein X═—CO$_2$Me, the base promoted hydrolysis is typically performed under milder conditions using methods known to those skilled in the art of organic synthesis. The product is a compound of type 8, which can be elaborated to compounds of the present invention (I) as described in the subsequent schemes.

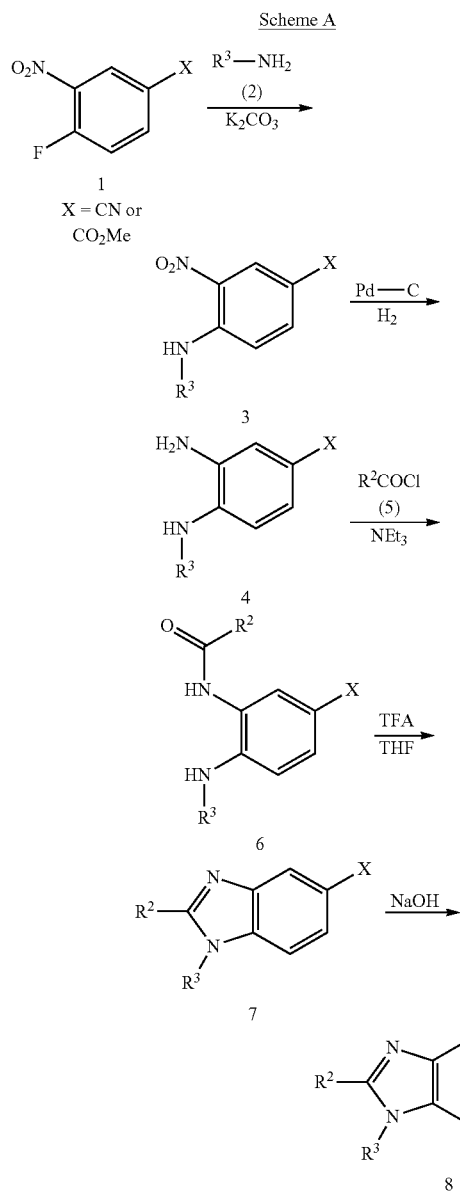

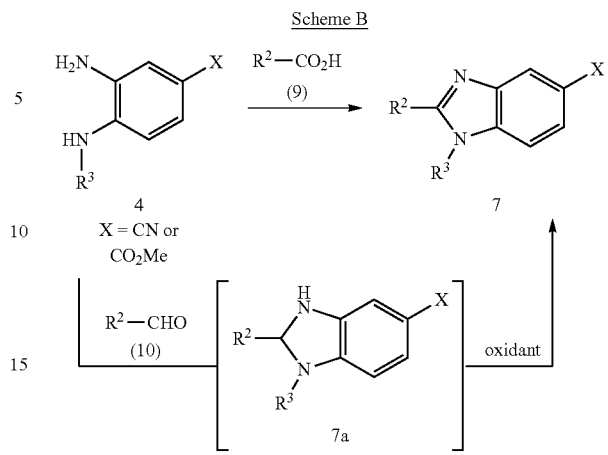

Reaction scheme C illustrates a preferred method for the synthesis of compounds of type 7. In this method, nitroanilines of type 3 are subjected to a multi-step, one pot process to afford benzimidazoles of type 7 (Yang, D., et al. *Synthesis* 2005, 47-56). In the first step, the nitro group from compounds of type 3 is reduced by a suitable mild reductant, such as sodium thiosulfide, to afford an aryl diamine of type 4, that reacts in situ with an aldehyde of type 10, under similar conditions as described above in Scheme B to form an intermediate benzoxazolidine (see Scheme B, cpd 7a) that subsequently reacts with a suitable oxidant, such as air, to afford the target compound of type 7. This multi-step reaction is run in a suitable inert solvent, such as DMSO or ethanol, or a mixture thereof, at a reaction temperature between 100° C. and the boiling point of the reaction mixture, for between 8-24 h. The product derived from this method is a compound of type 7, which can be elaborated to compounds of the present invention (I) as described in the subsequent schemes.

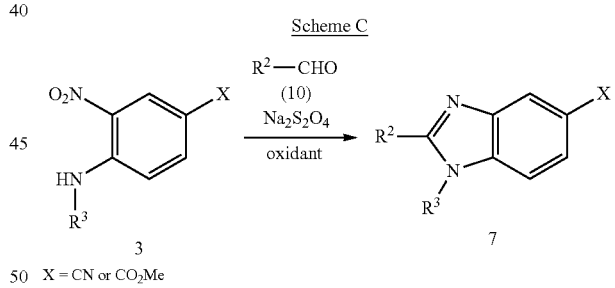

Reaction scheme B illustrates a general method for the synthesis of compounds of type 7. In this method, an aryl diamine of type 4 is either reacted with a suitable carboxylic acid of type 9, commonly at reaction temperatures between 150° C. and the boiling point of the reaction mixture. The reaction is typically run neat or in the presence of polyphosphoric acid. An alternate preferred method for the synthesis of compounds of type 7 involves reacting an aryl diamine of type 4 with an aldehyde of type 10 via a benzoxazolidine intermediate of type 7a that reacts in situ with a suitable oxidant, such as ozone or air, typically between room temperature and the boiling point of the reaction mixture. The product derived from both methods is a compound of type 7, which can be elaborated to compounds of the present invention (1) as described in the subsequent schemes.

Reaction scheme D illustrates a preferred method for the synthesis of compounds of type 15. In this method, an aryl diamine of type 4 is treated with an acylating agent capable of reacting with two vicinal amine moieties, such as 1,1'-carbonyldiimidazole or triphosgene, in an inert solvent such as DCM, typically at room temperature. The product of the reaction is a 2-oxobenzimidazole of type 11, which can be subsequently reacted with an electrophilic activating agent, such as phosphorous oxychloride, or the like. It is customary for the reaction to be run neat at elevated temperatures, commonly above 100° C., up to the boiling point of the reaction mixture. The product of the reaction is a 2-chlorobenzimidazole of type 12 that can be treated with a suitable amine of type 13 in a nucleophilic displacement reaction. The reaction can be run in a number of solvents, such as isopropyl alcohol or toluene, at elevated temperature between 60° C. and the boiling temperature of the reaction mixture, and as previously stated for a nucleophilic displacement, the reaction may be accelerated by the use of a microwave reactor. The product of the reaction is a 2-aminobenzimidazole of type 14 that can be submitted to general procedures previously described for the conversion of compounds of type 7 to carboxylic acids of type 8 in Scheme A to afford a benzimidazole carboxylic acid of type 15, which can be elaborated to compounds of the present invention (I) as described in the subsequent schemes.

128, 5360-5361), in a modification of the method commonly referred to as the Suzuki reaction. The reaction requires the addition of a suitable base, such as sodium bis(trimethylsilyl) amide, and is typically assembled and run under an inert atmosphere, preferably with the assistance of a glove box, generally at temperatures between 60° C. and 80° C. for between 5-12 h. The product of the reaction is a substituted cyclic amine of type 19, which can be elaborated to compounds of the present invention (I) as described in the subsequent schemes.

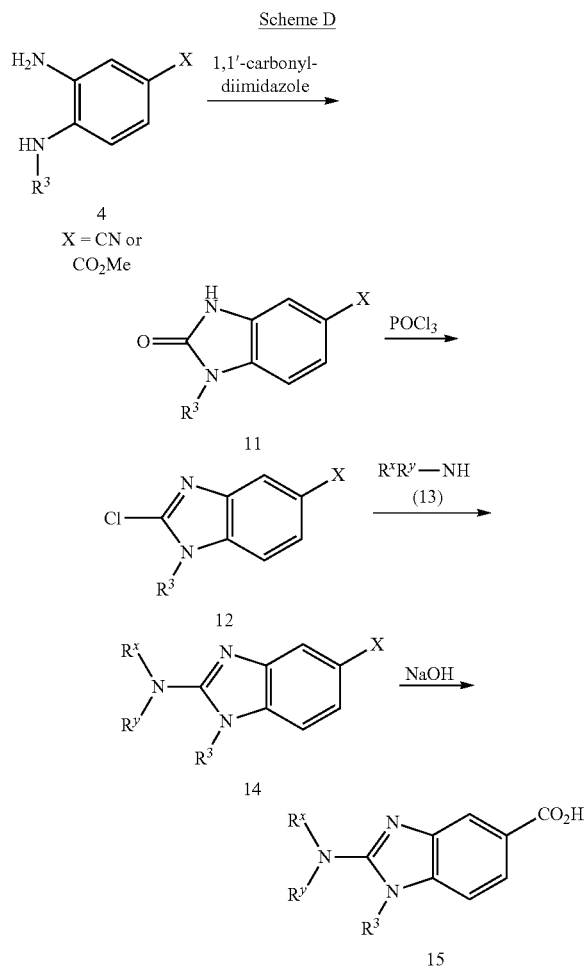

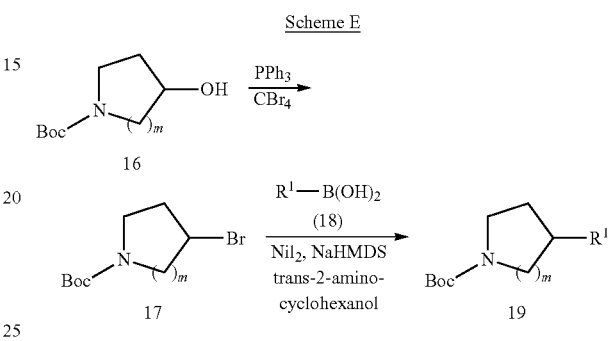

Reaction scheme F illustrates a general method for the synthesis of compounds of type 22. In this method, commercially available amine (20) is treated with an activating acid, such as TFA or the like, in the presence of a suitable olefin of type 21 in a [3+2] cycloaddition reaction in which amine 20 in activated by the acid source such that it can subsequently participate in the cycloaddition reaction. (Terao, Y., et al. *Chem. Pharm. Bull.* 1985, 33, 2762-2766) The reaction is typically conducted at room temperature in an inert solvent, such as DCM or benzene, or the like. The product of the reaction is a pyrrolidine of type 22, which can be elaborated to compounds of the present invention (I) as described in the subsequent schemes.

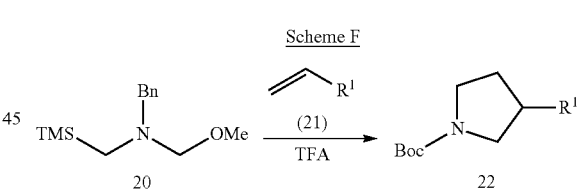

Reaction scheme E illustrates a preferred method for the synthesis of compounds of type 19. In this method, a protected aminoalcohol of type 16 is reacted in the presence of triphenylphosphine and an activating agent, such as carbon tetrabromide, for which the conjugate base from the initial reaction, bromide ion, subsequently participates in a nucleophilic displacement of the activated alcohol moiety. The reaction can be run in a number of inert solvents, such as THF, acetonitrile or DCM, and is commonly initiated at reduced temperatures, such as 0° C., while permitting slow warming to room temperature. The product of the reaction is a bromide of type 17 that is treated with a boronic acid (18) in the presence of a suitable catalyst, such as nickel diiodide, and ligand, such as trans-2-aminocyclohexanol, according to the procedures reported by Fu, et al. (*J. Am. Chem., Soc.* 2006, Reaction scheme G illustrates an alternate general method for the synthesis of compounds of type 19. In this method, a cyclic amine ketone of type 23 is treated with a base, such as lithium bis(trimethylsilyl)amide, or LDA, or the like, followed by the addition of a suitable triflating reagent, such as trifle anhydride. The reaction is typically performed in an etheral solvent, such as diethyl ether, or THF, or a mixture thereof, at −78° C. The product of the reaction is a vinyl triflate of type 24 that is reacted with an aryl boronic acid of type 18 in a method commonly referred to as a Suzuki reaction. The reaction is performed in the presence of a suitable palladium catalyst, such as [1,1'-bis(diphenylphosphino)ferrocene]-dichloropalladium(II), or tetrakis(triphenylphosphine)palladium(0), or the like, and a mild base, such as sodium carbonate, sodium phosphate tribasic, or the like (*Pure Appl. Chem.* 1991, 63, 419-422). The reaction is usually performed in a suitable degassed aqueous mixture of inert solvents, such as toluene, ethanol or dioxane, at elevated temperatures, generally between 70° C. and the boiling temperature of the reaction mixture, for a period of 3-24 h. Recently, conditions suitable for performing Suzuki reaction at room temperature have been published (for example, see: *J. Am. Chem. Soc.* 2000, 122, 4020-4028, and references therein). The product of the reaction is a vinyl compound of type 25 that is converted to a saturated cyclic amine of type 19 by treatment with a suitable palladium catalyst, such as palladium on carbon, at either atmospheric or elevated pressures of hydrogen. The reaction is usually conducted in an inert solvent, such as ethanol or ethyl acetate, or a mixture thereof, at room temperature for a period of 3-5 h. The cyclic amine product 19 can be elaborated to compounds of the present invention (I) as described in the subsequent schemes.

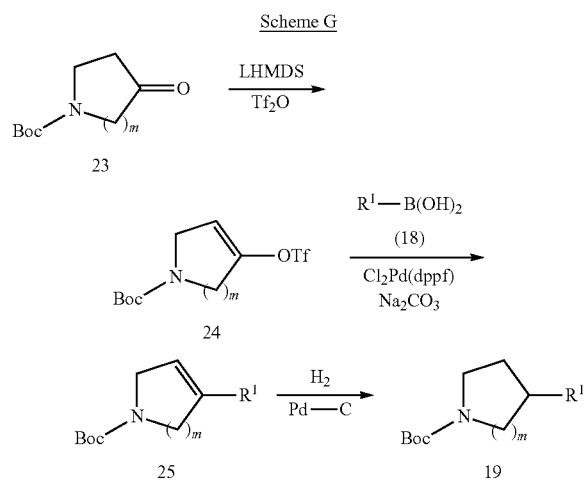

Reaction scheme H illustrates a general method for the synthesis of compounds of type 27. In this method, a cyclic amine ketone of type 23 is treated with an organometallic reagent of type 26, commonly referred to as Grignard or Gilman reagents, capable of transferring an aryl group, to afford a tertiary alcohol of type 27. It is customary to conduct the reaction in a suitable etheral solvent, such as diethyl ether or THF, or a mixture thereof, at temperatures between −78° C. and room temperature. The product of the reaction, a tertiary alcohol of type 27 can be elaborated to compounds of the present invention (I) as described in the subsequent schemes.

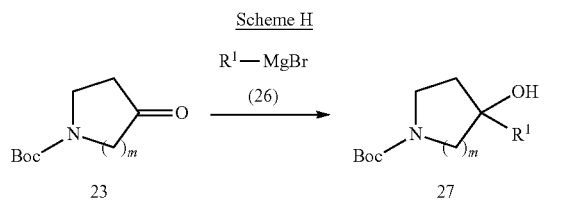

Reaction scheme I illustrates a general method for the synthesis of compounds of type 28. In this method, a tertiary alcohol of type 27 is treated with a fluorinating reagent, such as DAST or Deoxofluor™, in a suitable inert solvent, such as DCM, at −78° C. The product of the reaction, fluoride 28 can be elaborated to compounds of the present invention (I) as described in the subsequent schemes.

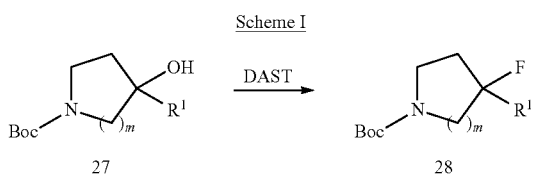

Reaction scheme J illustrates a general method for the synthesis of compounds of type 34, wherein v=a suitable —C$_{1-4}$alkyl substituent optionally substituted with —F, as defined for substituent "z" in Formula I. In this method, an aryl ketone of type 29 is treated with a phosphonate anion to afford an α,β-unsaturated ester (30) in a reaction commonly known as the Horner-Emmons reaction. The phosphonate reagent, trimethylphosphonoacetate, or the like, is initially treated with a suitable base, such as sodium hydride, typically in an etheral solvent, such as diethyl ether or THF, commonly between 0° C. and room temperature, following which, the ketone (29) is added to the reaction mixture. The product is an α,β-unsaturated ester of type 30 that is treated with an excess of nitromethane in the presence of a suitable base, such as cesium carbonate, or the like, in an inert polar aprotic solvent, such as DMSO, at elevated temperatures between 120° C. and the boiling point of the reaction mixture, and as previously indicated for a nucleophilic addition in Scheme A, the reaction may be accelerated by the use of a microwave reactor. The product of the reaction is a γ-nitroester of type 31, which is treated under similar reaction conditions as those described above in Scheme A for the reduction of nitroaniline 3 to aryl diamine 4. The direct product of the reaction, a γ-aminoester of type 32, can spontaneously undergo cyclization to a lactam of type 33 during the reduction step, to afford a crude mixture of both amine 32 and lactam 33. This product mixture can be converted to a lactam of type 33 by heating at elevated temperatures between 40° C. and the boiling point of the reaction mixture in a suitable inert solvent, such as EtOH. It is common to add a suitable base, such as potassium carbonate, or a catalyst, such as DMAP, to accelerate the reaction. The product of the reaction is a lactam of type 33 that is treated with a suitable reducing agent, such as borane-THF complex, or the like, in an inert solvent, such as THF or toluene, at elevated temperatures between 50° C. and the boiling temperature of the reaction mixture for 1-24 h. It is common to heat the reaction mixture in an appropriate sealed vessel. The product of the reaction is an amine of type 34, which can be elaborated to compounds of the present invention (I) as described in subsequent schemes.

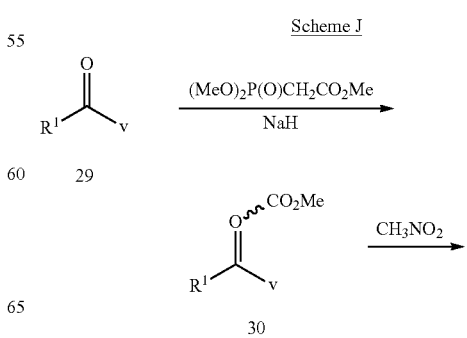

25

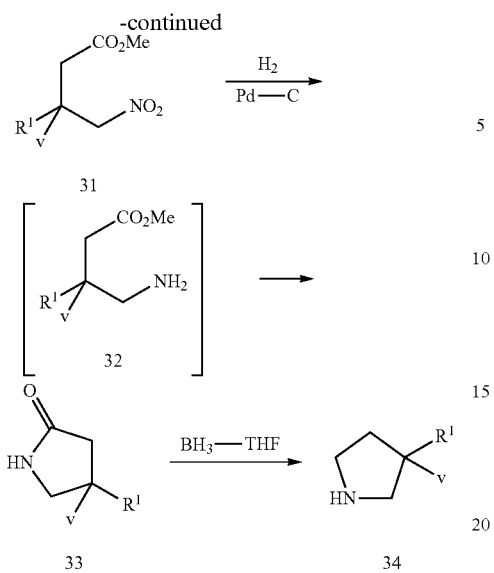

v = a suitable ——C1-4alkyl substituent optionally substituted with —— F, as defined for substituent "z" in Formula I Scheme K illustrates that compounds of structural formula 35 can be elaborated to a variety of heterocyclic (HAR) derivatives of structural formula 36 using known methods in organic synthesis. Specific examples of such transformations are shown in the Examples section. Leading references for effecting such transformations include:

Joule, J. A.; Mills, K. and Smith, G. F. *Heterocyclic Chemistry*, Chapman & Hall, 1995, 3rd Edn., and references cited therein;

Katrittzky, A. R.; Rees, C. W. (Eds), *Comprehensive Heterocyclic Chemistry: The Structure, Reactions, Synthesis, and Uses of Heterocyclic Compounds*, Pergamon Press, Oxford, 1984, 8v, and references cited therein; and Comprehensive Heterocyclic Chemistry II: Review of the Literature 1982-1995: The Structure, Reactions, Synthesis and Uses of Heterocyclic Compounds, Pergamon Press, New York, 2nd Edn., 1996, 11v, and references cited therein.

Scheme K

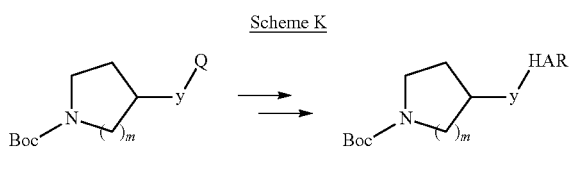

Q = CO$_2$H or NH$_2$
HAR = heteroaryl as defined within R$^1$

Reaction scheme L illustrates methods for the syntheses of compounds of type 38. For example, a benzimidazole carboxylic acid of type 8 can participate in amide bond coupling reactions with an amine of type 37 to afford an amide structural formula 38, in an appropriate inert solvent such as DMF, DCM or the like and may be performed with a variety of reagents suitable for amide coupling reactions such as HATU, EDC or PyBOP. Preferred conditions for the amide bond coupling reaction shown in reaction Scheme L are known to those skilled in organic synthesis. Such modifications may include, but are not limited to, the use of basic reagents such

26 as triethylamine, DIPEA, or NMM, or the addition of an additive such as DMAP, HOAt or HOBt.

Scheme L

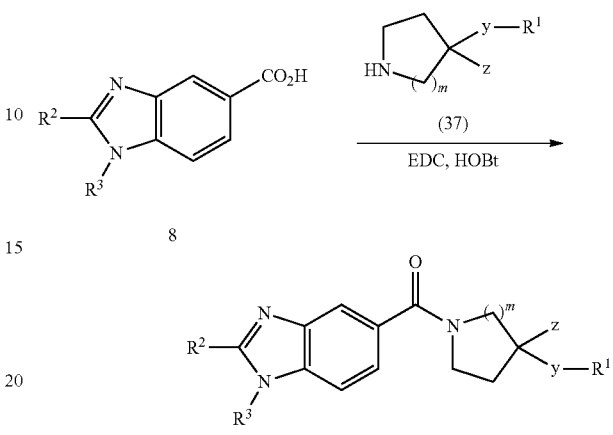

Scheme M illustrates a method for the resolution of representative compounds or intermediates of structural formula 39. Generally, representative compounds, or intermediates en route to their preparation, may be resolved to afford enantiomerically pure compounds such as 40 and 41 by chiral stationary phase liquid chromatography techniques or other suitable methods known in organic synthesis.

Scheme M

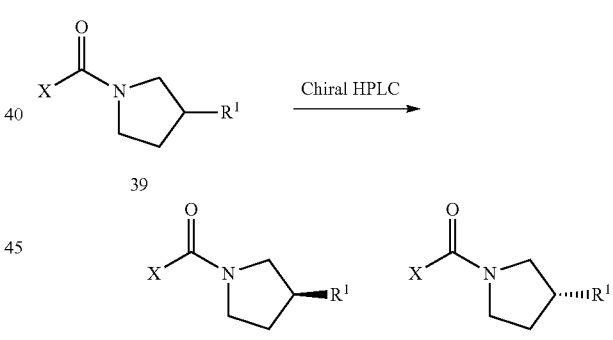

X = a suitable protecting group, or any structure consistent with the structural formula I.

Intermediates used in the synthesis of compounds of this invention can be prepared using the following procedures. In the Tables associated with the following Schemes, compounds having mass spectral data were synthetically prepared.

For compounds that were enantiomerically resolved according to the procedures described in Scheme M and other Schemes and Examples herein, the slower eluting enantiomers yielded preferable IC$_{50}$ results in the PAF Binding Assay over the corresponding faster eluting enantiomers, with the exception of compound 1Ar, where the faster eluting enantiomer was preferred. The absolute stereochemistry of the isolated enantiomers was not determined.

Scheme i-1

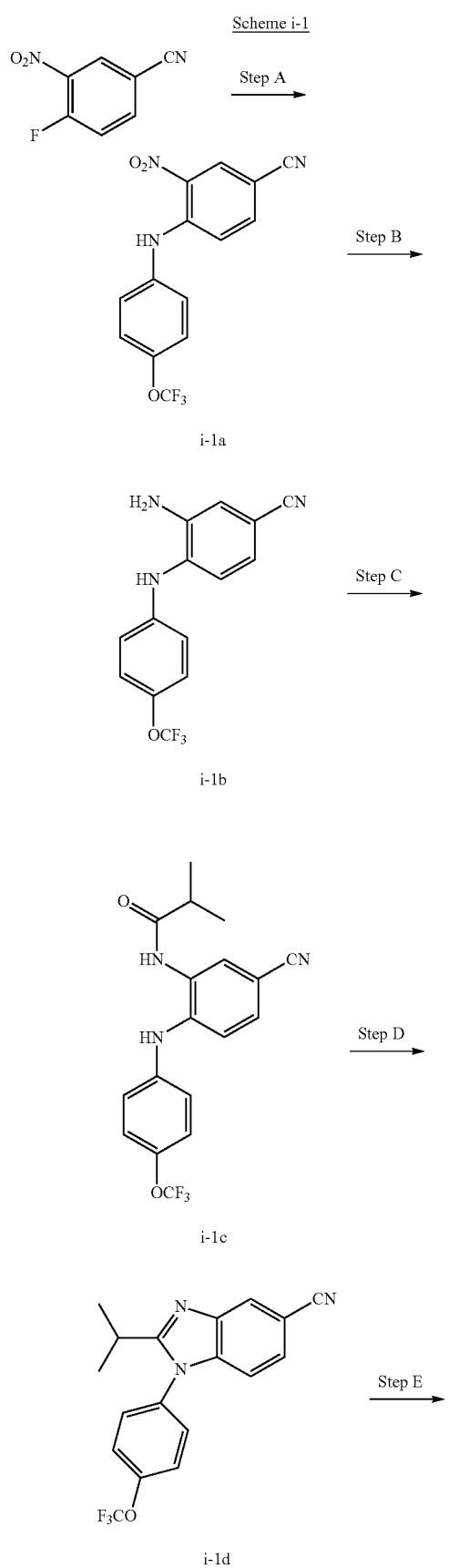

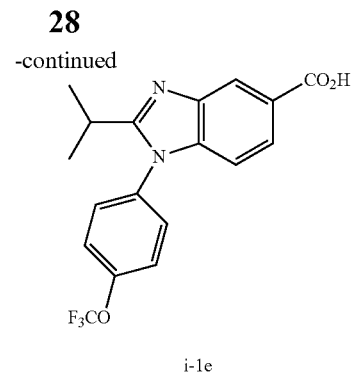

Preparation of i-1e

Step A: Preparation of 3-nitro-4-{[4-(trifluoromethoxy)phenyl]amino}benzonitrile (i-1a)

A solution of 4-fluoro-3-nitrobenzonitrile (500 mg, 3.01 mmol), 4-trifluoromethoxyaniline (404 µL, 3.01 mmol) and potassium carbonate (416 mg, 3.01 mmol) in DMSO (15.0 mL) were heated in a sealed tube within a microwave reactor at 120° C. for 10 min. The reaction mixture was cooled to rt and partitioned between EtOAc and water. The organic layer was washed with water and brine, dried (sodium sulfate) and concentrated in vacuo. Purification of the crude residue by flash chromatography on silica gel (gradient elution; 0%-40% EtOAc/hexanes as eluent) afforded the title compound i-1a. m/z (ES) 324 (MH)$^+$. $^1$H NMR (500 MHz, CDCl$_3$): δ 9.81 (s, 1H), 8.60 (d, 1H, J=1.9 Hz), 7.58 (dd, 1H, J=1.8, 9.1 Hz), 7.29 (m, 4H), 7.16 (d, 1H, J=8.9 Hz).

Step B: Preparation of 3-amino-4-{[4-(trifluoromethoxy)phenyl]amino}benzonitrile (i-1b)

A degassed solution of i-1a (690 mg, 2.14 mmol) and 10 wt. % palladium on carbon (227 mg, 0.213 mmol) in methanol (21.0 mL) was stirred under hydrogen (1 Atm.) at rt for 1 h. The reaction mixture was diluted with EtOAc and filtered through a short column of Celite®. The Celite® column was rinsed with additional portions of EtOAc, and the combined organic fractions were dried (sodium sulfate) and concentrated in vacuo to afford the title compound i-1b. m/z (ES) 294 (MH)$^+$.

Step C: Preparation of N-(5-cyano-2-{[4-(trifluoromethoxy)phenyl]amino}phenyl)-2-methylpropanamide (i-1c)

Isobutyryl chloride (42.0 µL, 0.400 mmol) was added to a stirred suspension of i-1b (117 mg, 0.400 mmol) and cesium carbonate (261 mg, 0.800 mmol) in DCM (2.00 mL), and the resulting mixture was allowed to stir at rt. After 2 h, the reaction was quenched with 1.0 M aq. HCl and extracted with EtOAc. The combined organics were washed with brine, dried (sodium sulfate) and concentrated in vacuo to afford the title compound i-1c. m/z (ES) 364 (MH)$^+$.

Step D: Preparation of 2-isopropyl-1-[4-(trifluoromethoxy)phenyl]-1H-benzimidazole-5-carbonitrile (i-1d)

A solution of i-1c (117 mg, 0.322 mmol) in THF (1.60 mL) and TFA (1.60 mL) was heated in a sealed tube within a microwave reactor at 100° C. for 10 min. The reaction mixture was cooled to rt and quenched into chilled satd. aq. NaHCO$_3$. The resulting mixture was extracted with EtOAc, and the combined organics were washed with brine, dried (sodium sulfate) and concentrated in vacuo to afford the title compound i-1d. m/z (ES) 346 (MH)$^+$.

Step E: Preparation of 2-isopropyl-1-[4-(trifluoromethoxy)phenyl]-1H-benzimidazole-5-carboxylic acid (i-1e)

A solution of i-1d (1.33 g, 3.86 mmol) and 5N aq. NaOH (3.90 mL, 19.5 mmol) in dioxane (4.80 mL) and water (10.0 mL) was heated in a sealed tube within a microwave reactor at 150° C. for 20 min. The reaction mixture was cooled to rt, quenched into satd. aq. NH$_4$Cl, and adjusted to pH ~4 with conc. HCl. The resulting mixture was filtered, and the filtrate was extracted with EtOAc. The combined organics were dried (sodium sulfate) and concentrated in vacuo to afford the title compound i-1e. m/z (ES) 365 (MH)$^+$.

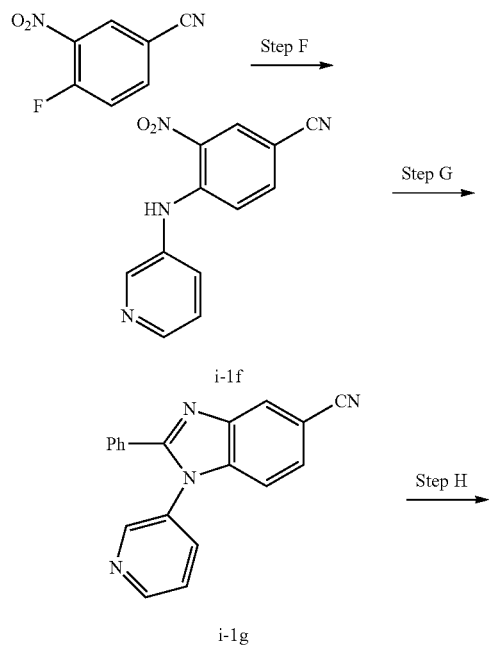

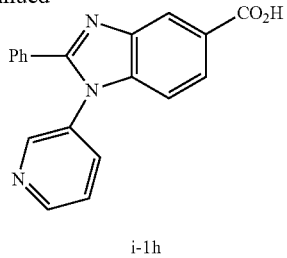

i-1h

Preparation of 2-phenyl-1-pyridin-3-yl-1H-benzimidazole-5-carboxylic acid (i-1h)

Step F: Preparation of 3-nitro-4-(pyridin-3-ylamino)benzonitrile (i-1f)

Compound i-1f was prepared following procedures similar to those described above in step A, substituting 3-aminopyridine for 4-(trifluoromethoxy)aniline.

Step G: Preparation of 2-phenyl-1-pyridin-3-yl-1H-benzimidazole-5-carbonitrile (i-1g)

A stirred solution of i-1f (80.0 mg, 0.330 mmol), benzaldehyde (33.5 µL, 0.330 mmol), Na$_2$S$_2$O$_4$ (58.0 mg, 0.330 mmol) in DMSO/EtOH (2.00 mL of a 1:3 mixture) was heated to 110° C. under an oxygen atmosphere overnight. The reaction mixture was cooled to rt, quenched with ammonium hydroxide and extracted with EtOAc. The combined organics were washed with brine, dried (sodium sulfate) and concentrated in vacuo. The resulting mixture was purified by preparative reversed phase HPLC on YMC Pack Pro C18 stationary phase (CH$_3$CN/H$_2$O as eluent, 0.05% TFA as modifier) to afford the title compound, i-1g.

Step H: Preparation of 2-phenyl-1-pyridin-3-yl-1H-benzimidazole-5-carboxylic acid (i-1h)

Compound i-1h was prepared following procedures similar to those described above in step E, substituting was prepared following procedures similar to those described above in step E, substituting i-1g for i-1d. m/z (ES) 316 (MH)$^+$.

Following procedures similar to those described for the preparation of intermediate i-1e, and, or i-1h, the following compounds in Tables i-1A1 and i-1A2 can be prepared.

TABLE i-1A1 i-1A

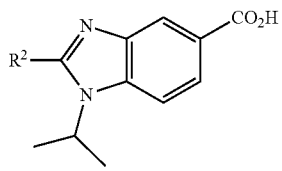

i-1B

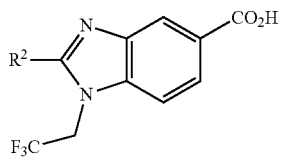

TABLE i-1A1-continued

[Structure i-1C: 1-tert-butyl-2-R²-benzimidazole-5-carboxylic acid]

[Structure i-1D: 1-(4-fluorobenzyl)-2-R²-benzimidazole-5-carboxylic acid]

[Structure i-1E: 1-cyclopropyl-2-R²-benzimidazole-5-carboxylic acid]

[Structure i-1F: 1-cyclobutyl-2-R²-benzimidazole-5-carboxylic acid]

[Structure i-1G: 1-(1-methylcyclopropyl)-2-R²-benzimidazole-5-carboxylic acid]

[Structure i-1H: 1-(pyridin-3-yl)-2-R²-benzimidazole-5-carboxylic acid]

| Ex. i-1A | Ex. i-1B | Ex. i-1C | Ex. i-1D | Ex. i-1E | Ex. i-1F | Ex. i-1G | Ex. i-1H | $R^2$ |
|---|---|---|---|---|---|---|---|---|
| a | a | a | a | a | a | a | a | Me |
| b | b | b | b | b | b | b | b | $CF_3$ |
| c | c | c | c | c | c | c | c | $^i$Pr |
| d | d | d | d | d | d | d | d | $^i$Bu |
| e | e | e | e | e | e | e | e | $^t$Bu |
| f | f | f | f | f | f | f | f | $^c$Pr |
| g | g | g | g | g | g | g | g | $^c$Bu |
| h | h | h | h | h | h | h | h | 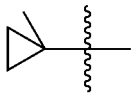 [SMILES: *C1(C)CC1] |

TABLE i-1A1-continued
| | | | | | | | | |
|---|---|---|---|---|---|---|---|---|
| i | i | i | i | i | i | i | i | 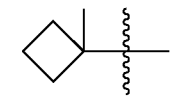 [SMILES: *C1(C)CCC1] |
| j | j | j | j | j | j | j | j | 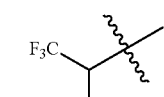 |
| k | k | k | k | k | k | k | k | 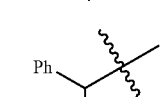 |
| l | l | l | l | l | l | l | — | Ph |
| m | m | m | m | m | m | m | m | 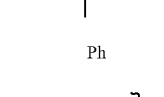 |
| n | n | n | n | n | n | n | n | 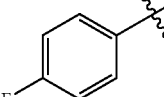 |
| o | o | o | o | o | o | o | o | 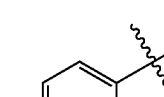 |
| p | p | p | p | p | p | p | p | 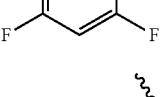 |
| q | q | q | q | q | q | q | q | 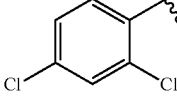 |
| r | r | r | r | r | r | r | r | 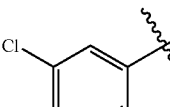 |
| s | s | s | s | s | s | s | s | 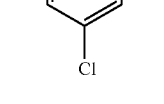 |
| t | t | t | t | t | t | t | t | Bn |

TABLE i-1A1-continued

| | | | | | | | | |
|---|---|---|---|---|---|---|---|---|
| u | u | u | u | u | u | u | u |  |
| v | v | v | v | v | v | v | v |  |
| w | w | w | w | w | w | w | w | 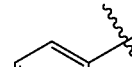 |

Parent Ion m/z (MH)$^+$ data for compounds i-1Ac: 247; i-1Ak: 309; i-1Al: 281; i-1Am: 299; i-1Ar: 365; i-1As: 417; i-1Bl: 321; i-1Bn: 357; i-1Bo: 389; i-1Bp: 389; i-1Bq: 405; i-1Br: 405; i-1Bu: 369; i-1Bv: 322; i-1Bw: 322; i-1Cr: 379; i-1Dl: 347; i-1Dn: 383; i-1Do: 415; i-1Dp: 415; i-1Dq: 431; i-1Dr: 431; i-1Du: 395; i-1Wv: 348; i-1Dw: 348; i-1El: 279; I-1En: 315; i-1Eo: 347; i-1Eq: 363; i-1Er: 363; i-1Es: 415; i-1Fl: 293; i-1Fn: 329; i-1Fo: 361; i-1Fq: 377; i-1Fr: 377; i-1Fu: 341; i-1Fv: 294; i-1Fw: 294; i-1Gr: 377; i-1Hn: 352; i-1Ho: 384; i-1Hq: 400; i-1Hr: 400; i-1Hu: 364; i-1Hv: 317; i-1Hw: 317.

TABLE i-1A2 i-1I

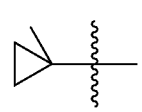

i-1J

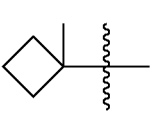

TABLE i-1A2-continued i-1K

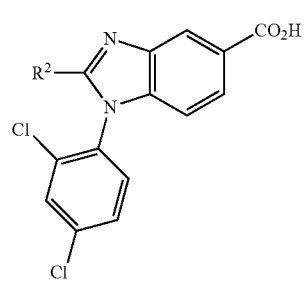

i-1L

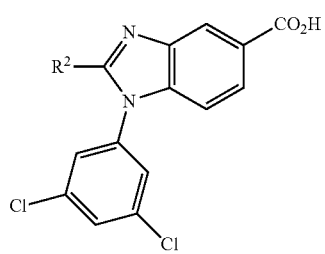

| Ex. i-1I | Ex. i-1J | Ex. i-1K | Ex. i-1L | R$^2$ |
|---|---|---|---|---|
| a | a | a | a | Me |
| b | b | b | b | CF$_3$ |
| c | — | c | c | $^i$Pr |
| d | d | d | d | $^i$Bu |
| e | e | e | e | $^t$Bu |
| f | f | f | f | $^c$Pr |
| g | g | g | g | $^c$Bu |
| h | h | h | h | 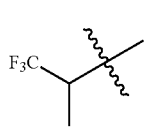 |
| i | i | i | i |  |
| j | j | j | j | F$_3$C— |

TABLE i-1A2-continued
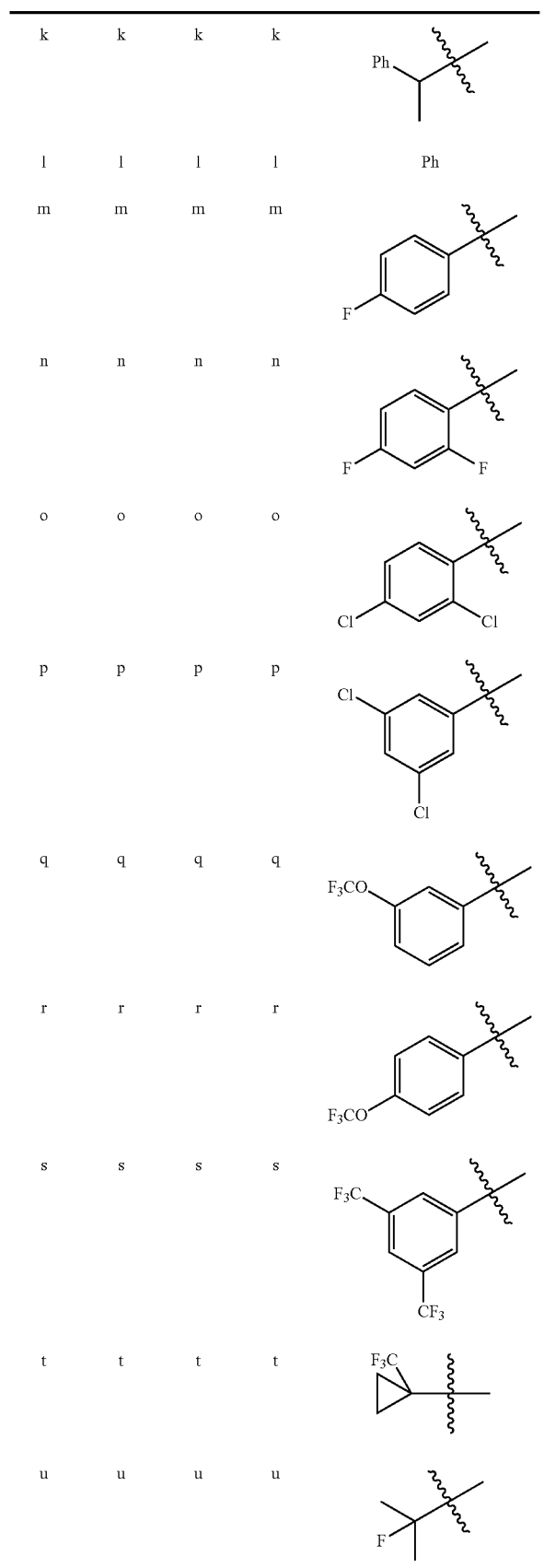
TABLE i-1A2-continued
Parent Ion m/z (MH)+ data for compounds i-1Ia: 253; i-1Is: 451; i-1Ja: 337; i-1Jb: 391; i-1Jc: 365; i-1Jd: 379; i-1Je: 379; i-1Jf: 363; 377; i-1Jh: 377; i-1Ji: 391; i-1Jj: 419; i-1Jk: 427; i-1Jl: 399; i-1Jt: 431; i-1Ju: 383; i-1Jv: 379; i-1Kc: 349; i-1Lc: 349.
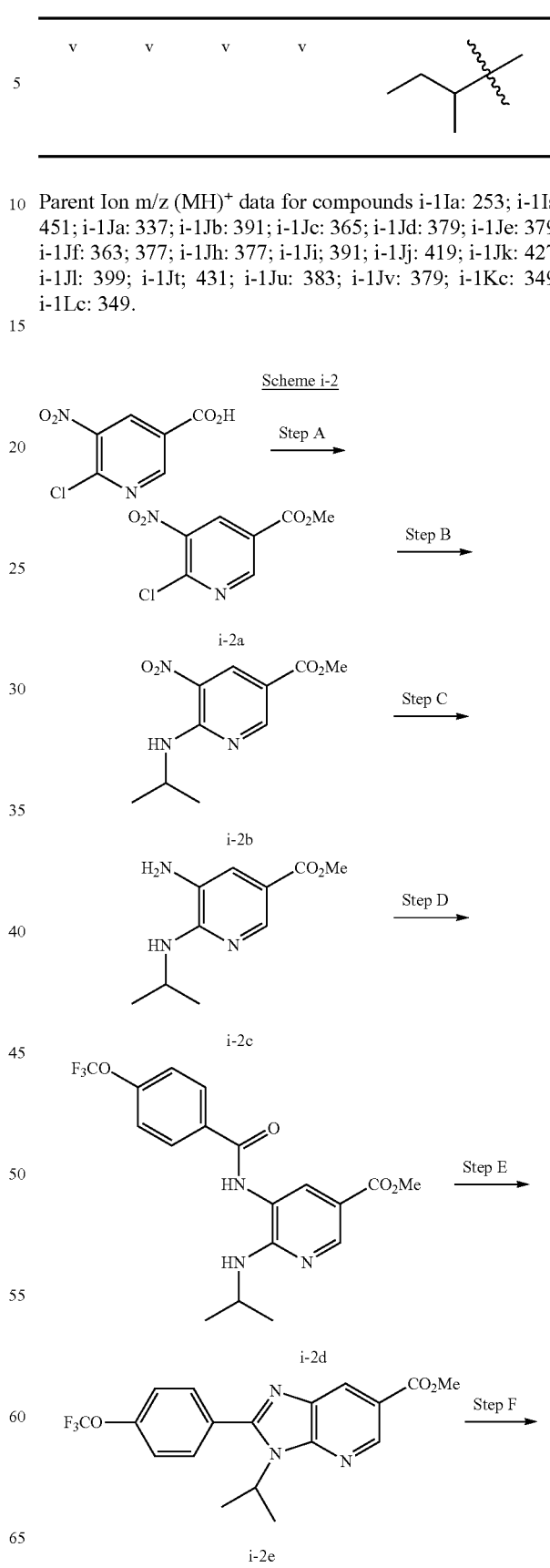

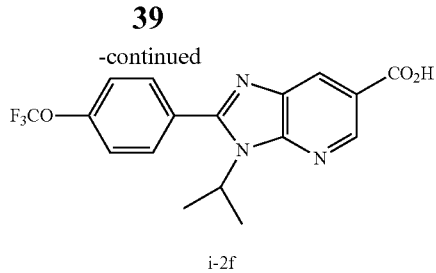

i-2f

Preparation of i-2f

Step A: Preparation of methyl 6-chloro-5-nitronicotinate (i-2a)

(Trimethylsilyl)diazomethane (8.25 mL of a 2.00 M solution in hexanes, 16.5 mmol) was added in three portions to a stirred solution of 6-chloro-5-nitronicotinic acid (1.00 g, 4.95 mmol) in methanol (12.0 mL) and DCM (24.0 mL) at 0° C. The reaction mixture was quenched with TPA and concentrated in vacuo to afford the title compound i-2a. m/z (ES) 217 (MH)$^+$. $^1$H NMR (500 MHz, CDCl$_3$): δ 9.20 (d, 1H, J=2.1 Hz), 8.79 (d, 1H, J=2.1 Hz), 4.05 (s, 3H).

Step B: Preparation of methyl 6-(isopropylamino)-5-nitronicotinate (i-2b)

i-2b was prepared following procedures similar to those described for the preparation of i-1a, substituting isopropylamine and i-2a for 4-(trifluoromethoxy)aniline and 4-fluoro-3-nitrobenzonitrile, respectively. $^1$H NMR (500 MHz, CDCl$_3$): δ 8.98 (m, 2H), 8.42 (m, 1H), 4.60 (m, 1H), 3.93 (s, 3H), 1.36 (d, 6H, J=6.5 Hz).

Step C: Preparation of methyl 5-amino-6-(isopropylamino)nicotinate (i-2c)

i-2c was prepared following procedures similar to those described for the preparation of i-1b, substituting i-2b for i-1a. $^1$H NMR (500 MHz, CDCl$_3$): δ 8.38 (d, 1H, J=2.0 Hz), 7.35 (d, 1H, J=2.0 Hz), 4.92 (d, 1H, J=5.3 Hz), 4.30 (m, 1H), 3.80 (s, 3H), 3.55 (br, 2H), 1.21 (d, 6H, J=6.4 Hz).

Step D: Preparation of methyl 6-(isopropylamino)-5-{[4-(trifluoromethoxy)benzoyl]amino}nicotinate (i-2d)

i-2d was prepared following procedures similar to those described for the preparation of i-1c, substituting i-2c for i-1b. $^1$H NMR (500 MHz, CDCl$_3$): δ 8.69 (d, 1H, J=2.0 Hz), 8.08 (br, 1H), 7.97 (d, 2H, J=8.2 Hz), 7.88 (s, 1H), 7.31 (d, 2H, J=8.5 Hz), 5.15 (d, 1H, J=7.4 Hz), 4.36 (m, 1H), 3.83 (s, 3H), 1.23 (d, 6H, J=6.6 Hz).

Step E: Preparation of methyl 3-isopropyl-2-[4-(trifluoromethoxy)phenyl]-3H imidazo[4,5-b]pyridine-6-carboxylate (i-2e)

i-2e was prepared following procedures similar to those described for the preparation of i-1d, substituting i-2d for i-1c.

Step F: Preparation of 3-isopropyl-2-[4-(trifluoromethoxy)phenyl]-3H-imidazo[4,5-b]pyridine-6-carboxylic acid (i-2f)

Lithium hydroxide (1.20 mL of a 3.0 M aq. solution, 3.60 mmol) was added to a stirred solution of i-2e (343 mg, 0.695 mmol) in dioxane (6.00 mL), and the resulting mixture was heated to 100° C. After 2 h, the reaction mixture was cooled to rt, and the excess base was quenched with 1.0 M HCl. The resulting mixture was concentrated in vacuo to afford the title compound i-2f. m/z (ES) 366 (MH)$^+$.

Following procedures similar to those described for the preparation of i-2f, the following compounds in Table i-2 can be prepared.

TABLE i-2

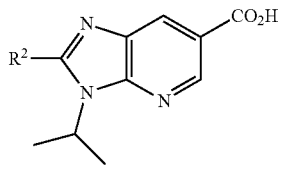

i-2A

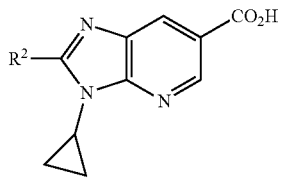

i-2B

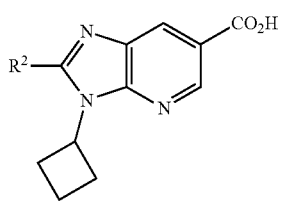

i-2C

TABLE i-2-continued
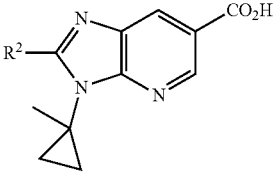
i-2D
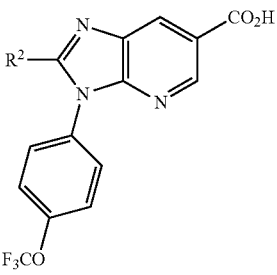
i-2E
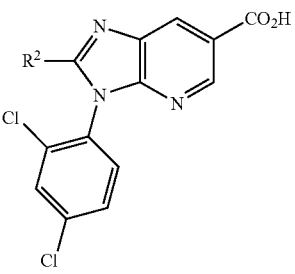
i-2F
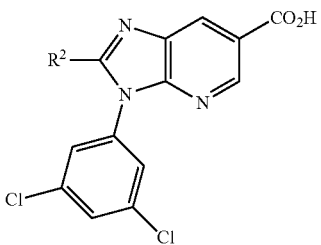
i-2G
| Ex. i-2A | Ex. i-2B | Ex. i-2C | Ex. i-2D | Ex. i-2E | Ex. i-2F | Ex. i-2G | R² |
|---|---|---|---|---|---|---|---|
| a | a | a | a | a | a | a | $^i$Pr |
| b | b | b | b | b | b | b | $^c$Pr |
| c | c | c | c | c | c | c | $^c$Bu |
| d | d | d | d | d | d | d | 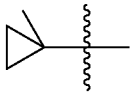 [SMILES: *C1(C)CC1] |
| e | e | e | e | e | e | e | 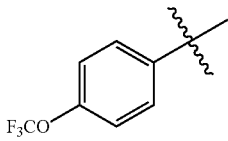 [SMILES: *c1ccc(OC(F)(F)F)cc1] |
| f | f | f | f | f | f | f | 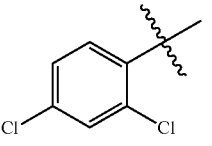 [SMILES: *c1ccc(Cl)cc1Cl] |

Scheme i-3

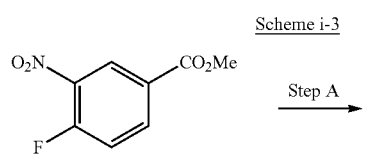

Step A →

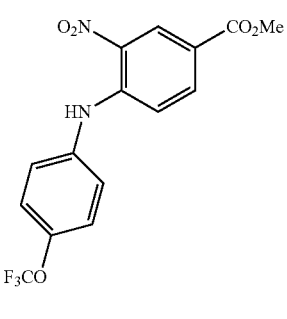

i-3a

Step B →

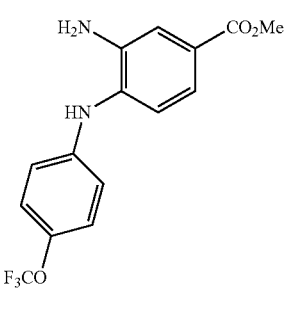

i-3b

Step C →

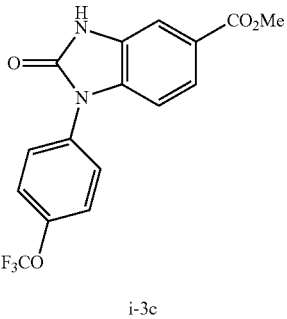

i-3c

Step D →

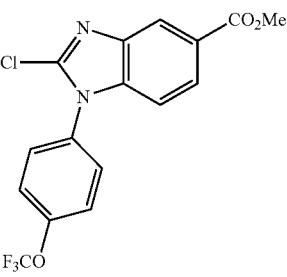

i-3d

Step E →

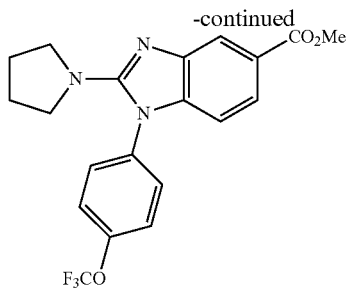

i-3e

Step F →

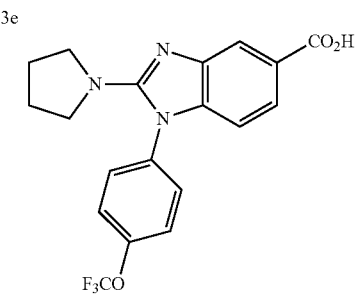

i-3f

Preparation of i-3f

Step A: Preparation of methyl 3-nitro-4-{[4-(trifluoromethoxy)phenyl]amino}benzoate (i-3a)

A stirred solution of methyl 4-fluoro-3-nitrobenzoate (853 mg, 4.28 mmol), 4-trifluoromethoxyaniline (759 mg, 4.28 mmol) and triethylamine (1.79 mL, 12.9 mmol) in DMF (5.00 mL) was heated to 70° C. for 24 h. The reaction mixture was concentrated in vacuo, and the resulting crude residue was purified by flash chromatography on silica gel (gradient elution; 0%-10% methanol/DCM as eluent) afforded the title compound i-3a. m/z (ES) 357 (MH)+. $^1$H NMR (500 MHz, CDCl$_3$): δ 9.77 (s, 1H), 8.96 (s, 1H), 8.03 (d, 1H, J=8.5 Hz), 7.34 (m, 4H), 7.16 (d, 1H, J=8.5 Hz), 3.95 (s, 3H).

Step B: Preparation of methyl 3-amino-4-{([4-(trifluoromethoxy)phenyl]amino}benzoate (i-3b)

i-3b was prepared following procedures similar to those described for the preparation of i-1b, substituting i-3a for i-1a, m/z (ES) 327 (MH)+.

Step C: Preparation of methyl 2-oxo-1-[4-(trifluoromethoxy)phenyl]-2,3-dihydro-1H-benzimidazole-5-carboxylate (i-3c)

1,1′-Carbonyldimidazole (1.04 g, 6.44 mmol) was added to a rapidly stirred solution of i-3b (1.05 g, 3.22 mmol) in THF (40.0 mL) at 0° C., and the resulting mixture was allowed to warm slowly to rt. The reaction mixture was quenched with brine and extracted with EtOAc. The combined organics were dried (magnesium sulfate) and concentrated in vacuo. Purification of the crude residue by flash chromatography on silica gel (gradient elution; 0%-10% methanol/DCM as eluent) afforded the title compound i-3c. m/z (ES) 353 (MH)+.

Step D: Preparation of methyl 2-chloro-1-[4-(trifluoromethoxy)phenyl]-1H-benzimidazole-5-carboxylate (i-3d)

A solution of i-3c (1.03 g, 2.92 mmol) in phosphorous oxychloride (5.00 mL) was heated to 110° C. After 3 h, the reaction mixture was cooled to rt, poured over ice and quenched with 1.0 N NaOH. The resulting mixture was extracted with EtOAc, and the combined organics were washed with water and brine, dried (magnesium sulfate) and concentrated in vacuo to afford the title compound i-3d. m/z (ES) 371 (MH)$^+$. $^1$H NMR (500 MHz, CDCl$_3$): δ 8.49 (s, 1H), 8.05 (m, 1H), 7.52 (m, 4H), 7.21 (dd, 1H, J=2.8, 8.6 Hz), 3.99 (s, 3H).

Step E: Preparation of methyl 2-pyrrolidin-1-yl-1-[4-(trifluoromethoxy)phenyl]-1H-benzimidazole-5-carboxylate (i-3e)

A solution of i-3d (98.0 mg, 0.264 mmol) and pyrrolidine (26.0 mL, 0.317 mmol) in isopropyl alcohol (1.50 mL) was heated in a sealed tube within a microwave reactor at 110° C. for 15 min. The reaction mixture was cooled to rt and concentrated in vacuo. Purification of the crude residue by flash chromatography on silica gel (gradient elution; 0%-80% EtOAc/hexanes as eluent) afforded the title compound i-3e. m/z (ES) 406 (MH)$^+$. $^1$H NMR (500 MHz, CDCl$_3$): δ 8.22 (d, 1H, J=1.5 Hz), 7.75 (dd, 1H, J=1.5, 8.5 Hz), 7.51 (d, 2H, J=6.5 Hz), 7.43 (d, 2H, J=8.5 Hz), 6.87 (d, 1H, J=8.0 Hz), 3.93 (s, 3H), 3.33 (m, 4H), 1.90 (m, 4H).

Step F: Preparation of 2-pyrrolidin-1-yl-1-[4-(trifluoromethoxy)phenyl]-1H-benzimidazole-5-carboxylic acid (i-3f)

i-3f was prepared following procedures similar to those described for the preparation of i-2f, substituting i-3e for i-2e. m/z (ES) 392 (MH)$^+$.

Following procedures similar to those described for the preparation of intermediate i-3f, the following compounds in Table i-3 can be prepared.

Parent Ion m/z (MH)⁺ data for compounds i-3e: 428; i-3g: 408.

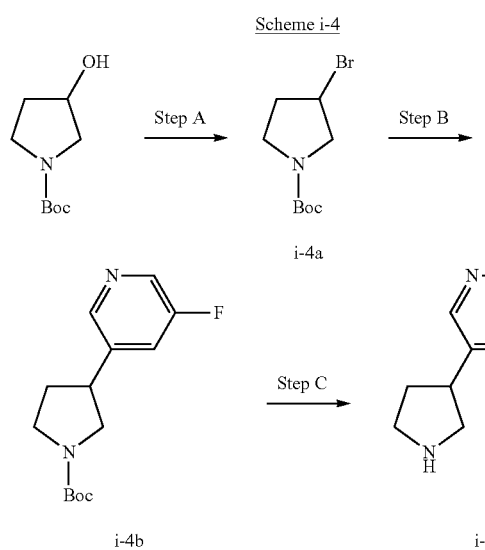

Scheme i-4 i-4a i-4b                    i-4c

Preparation of i-4-c

Step A: Preparation of tert-butyl 3-bromopyrrolidine-1-carboxylate (i-4-a)

Triphenylphosphine (727 mg, 2.77 mmol) was added to a stirred solution of tert-butyl 3-hydroxypyrrolidine-1-carboxylate (173 mg, 0.924 mmol) and carbon tetrabromide (919 mg, 2.77 mmol) in THF (3.00 mL) at 0° C., and the resulting mixture was allowed to warm slowly to rt. After 20 h, the reaction was filtered and concentrated in vacuo. Purification of the crude residue by flash chromatography on silica gel (gradient elution; 10%-40% EtOAc/hexanes as eluent) afforded the title compound i-4-a. m/z (ES) 250 (MH)⁺. ¹H NMR (500 MHz, CDCl₃): δ 4.49 (m, 1H), 3.81 (m, 2H), 3.63 (m, 1H), 3.53 (m, 1H), 2.33 (m, 1H), 2.26 (m, 1H), 1.49 (s, 9H).

Step B: Preparation of tert-butyl 3-(5-fluoropyridin-3-yl)pyrrolidine-1-carboxylate (i-4-b)

In a glove box, a suspension of nickel iodide (37.5 mg, 0.120 mmol), trans-2-aminocyclohexanol hydrochloride (18.2 mg, 0.120 mmol), (5-fluoropyridin-3-yl)boronic acid (282 mg, 2.00 mmol) and sodium bis(trimethylsilyl)amide (367 mg, 2.00 mmol) in isopropyl alcohol (3.30 mL) was allowed to stir for 5 min. i-4-a (250 mg, 0.460 mmol) was added, and the resulting mixture was heated to 80° C. for 5 h. The reaction mixture was cooled to rt, poured into satd. aq. NH₄Cl and extracted with EtOAc. The combined organics were washed with brine, dried (sodium sulfate) and concentrated in vacuo. Purification of the crude residue by flash chromatography on silica gel (gradient elution; 10%-80% EtOAc/hexanes as eluent) afforded the title compound i-4-b. m/z (ES) 267 (MH)⁺. ¹H NMR (500 MHz, CDCl₃): δ 8.39 (d, 1H, J=2.1 Hz), 8.37 (m, 1H), 7.31 (m, 1H), 3.88 (m, 1H), 3.64 (m, 1H), 3.24-3.52 (m, 3H), 2.35 (m, 1H), 2.01 (m, 1H), 1.51 (s, 9H).

Step C: Preparation of 3-fluoro-5-pyrrolidin-3-ylpyridine (i-4-c)

4.0 M HCl in dioxane (6.50 mL, 26.0 mmol) was added in two portions to a stirred solution of i-4-b (268 mg, 1.01 mmol) in methanol (10.0 mL) at 0° C. After 2 h, the excess HCl was purged via a stream of N₂, and the resulting mixture was concentrated in vacuo to afford the title compound i-4-c. m/z (ES) 167 (MH)⁺.

Following procedures similar to those described for the preparation of intermediate i-4-c, the following compounds in Table i-4 can be prepared.

TABLE i-4

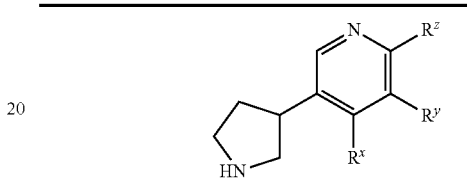

R$^x$, R$^y$, and R$^z$ are independently —H
or as defined for R⁴ in formula I.

| Ex. i-4 | R$^x$ | R$^y$ | R$^z$ |
|---|---|---|---|
| d | H | H | H |
| e | H | CF₃ | H |
| f | H | CN | H |
| g | H | Me | H |
| h | H | H | OMe |
| i | CF₃ | H | H |
| j | Me | H | H |
| k | H | H | Me |

Parent Ion m/z (MH)⁺ data for compounds i-4-d: 149; i-4-g: 163; i-4-h: 179.

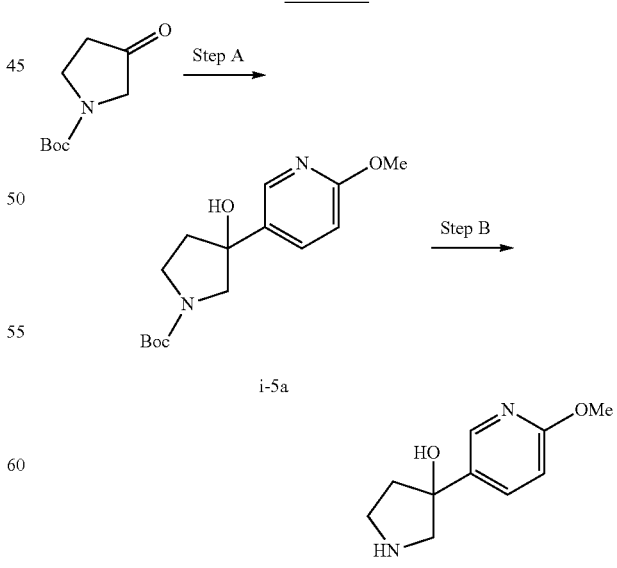

Scheme i-5 i-5a i-5b

Preparation of i-5b

Step A: Preparation of tert-butyl 3-hydroxy-3-(6-methoxypyridin-3-yl)pyrrolidine-1-carboxylate (i-5a)

5-bromo-2-methoxypyridine (324 μL, 2.50 mmol) was added dropwise to a stirred suspension of n-butyllithium (1.72 mL of a 1.6 M hexanes solution, 2.75 mmol) in ether (10.0 mL) at −78° C. After 10 min, a solution of N-Boc-3-pyrrolidinone (463 mg, 2.50 mmol) in ether (2.00 mL) was added dropwise, and the reaction mixture was allowed to stir at −78° C. After 2 h, the reaction was quenched with satd. aq. NH$_4$Cl and extracted with EtOAc. The combined organics were washed with brine, dried (sodium sulfate) and concentrated in vacuo. Purification of the crude residue by flash chromatography on silica gel (gradient elution; 10%-80% EtOAc/hexanes as eluent) afforded the title compound i-5a. m/z (ES) 295 (MH)$^+$. $^1$H NMR (500 MHz, CDCl$_3$): δ 8.31 (s, 1H), 7.71 (d, 1H, 7.1 Hz), 6.79 (dd, 1H, J=2.2, 8.6 Hz), 3.97 (s, 3H), 3.40-3.80 (m, 4H), 2.25 (m, 2H), 1.51 (s, 9H).

Step B: Preparation of 3-(6-methoxypyridin-3-yl)pyrrolidin-3-ol (i-5b)

i-5b was prepared following procedures similar to those described for the preparation of i-4c, substituting i-5a for i-4b. m/z (ES) 195 (MH)$^+$.

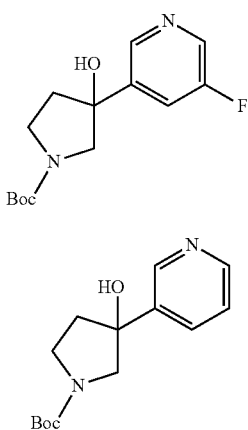

i-5x i-5y

Preparation of tert-butyl 3-(5-fluoropyridin-3-yl)-3-hydroxypyrrolidine-1-carboxylate (i-5x) and tert-butyl 3-hydroxy-3-pyridin-3-ylpyrrolidine-1-carboxylate (i-5y)

i-5x and i-5y were prepared following procedures similar to those described above in step A, substituting 3-bromo-5-fluoropyridine and 3-bromopyridine, respectively, for 5-bromo-2-methoxypyridine. For i-5x: m/z (ES) 283 (MH)$^+$. For i-5y: m/z (ES) 265 (MH)$^+$.

Following procedures similar to those described for the preparation of intermediate i-5b, the following compounds in Table i-5 can be prepared.

TABLE i-5

R$^x$, R$^y$, and R$^z$ are as defined for R$^4$ in formula I

| Ex. i-5 | R$^x$ | R$^y$ | R$^z$ |
|---|---|---|---|
| c | H | H | H |
| d | H | F | H |
| e | H | Cl | H |
| f | H | Me | H |
| g | H | OMe | H |
| h | H | CF$_3$ | H |
| i | H | CN | H |
| j | CF$_3$ | H | H |
| k | Me | H | H |
| l | H | H | Me |

Parent Ion m/z (MH)$^+$ data for compounds i-5c: 165; i-5d: 183; i-5e: 199; i-5f: 179; i-5g: 195; i-5h: 233; i-5i: 190.

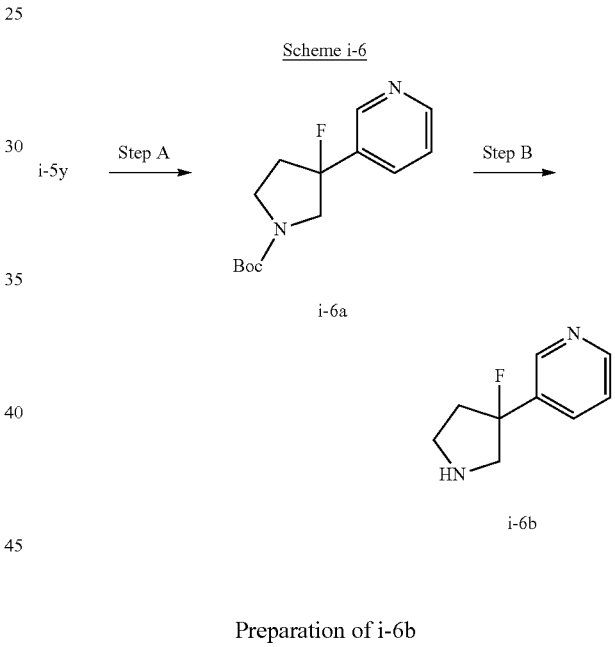

Scheme i-6

Preparation of i-6b

Step A: Preparation of tert-butyl 3-fluoro-3-pyridin-3-ylpyrrolidine-1-carboxylate (i-6a)

Bis(2-methoxyethyl)aminosulfur trifluoride (203 μL, 1.097 mmol) was added to a stirred solution of i-5c (290 mg, 1.097 mmol) in DCM (14.0 mL) at −78° C. After 45 min, the reaction mixture was quenched with said. aq. NaHCO$_3$ and extracted with DCM. The combined organics were washed with brine, dried (magnesium sulfate) and concentrated in vacuo. Purification of the crude residue by flash chromatography on silica gel (gradient elution; 0%-10% methanol/DCM as eluent) afforded the title compound i-6a. m/z (ES) 267 (MH)$^+$. NMR (500 MHz, CDCl$_3$): δ 8.71 (d, 1H, J=2.0 Hz), 8.63 (dd, 1H, J=1.0, 4.5 Hz), 7.77 (d, 1H, J=8.0 Hz), 7.36 (dd, 1H, J=5.0, 8.0 Hz), 3.99 (m, 1H), 3.78 (m, 1H), 3.66 (m, 2H), 2.26-2.53 (m, 2H), 1.51 (s, 9H).

Step B: Preparation of 3-(3-fluoropyrrolidin-3-yl)pyridine (i-6b)

i-6b was prepared following procedures similar to those described for the preparation of i-4-c, substituting i-6a for i-4-b. m/z (ES) 167 (MH)$^+$.

Following procedures similar to those described for the preparation of intermediate i-6b, the following compounds can be prepared.

i-6c

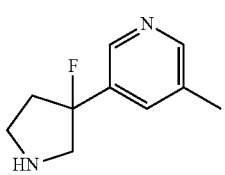
i-6d

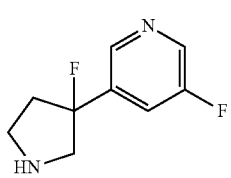
i-6e

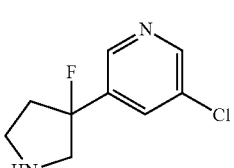
i-6f

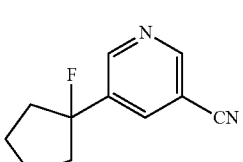
i-6g

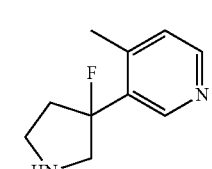
i-6h

Scheme i-7

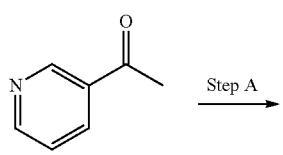
Step A

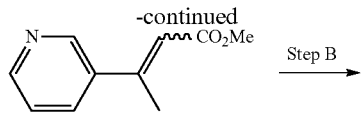
i-7a
Step B

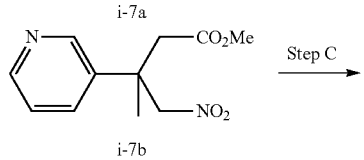
i-7b
Step C

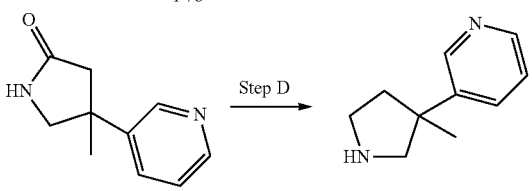
i-7c      i-7d

Preparation of i-7d

Step A: Preparation of methyl 3-pyridin-3-ylbut-2-enoate (i-7a)

Sodium hydride (192 mg of a 60% wt. suspension, 4.80 mmol) was added in several portions to a stirred solution of trimethylphosphonoacetate (712 μL, 4.40 mmol) in THF (20.0 mL). After 5 min, 1-pyridin-3-ylethanone (440 μL, 4.00 mmol) was added dropwise, and the resulting mixture was heated to reflux. After 20 h, the reaction mixture was cooled to rt, poured into satd. aq. NH$_4$Cl and extracted with EtOAc. The combined organics were washed with brine, dried (sodium sulfate) and concentrated in vacuo. Purification of the crude residue by flash chromatography on silica gel (gradient elution; 0%-60% EtOAc/hexanes as eluent) afforded the title compound i-7a as a separable mixture of two isomers. m/z (ES) 178 (MH)$^+$.

For i-7a (isomer A): $^1$H NMR (500 MHz, CDCl$_3$): δ 8.74 (s, 1H), 8.61 (m, 1H), 7.77 (dd, 1H, J=1.6, 8.0 Hz), 7.33 (m, 1H), 6.17 (d, 1H, J=0.9 Hz), 3.78 (s, 3H), 2.60 (d, 3H, J=1.1 Hz).

For i-7a (isomer B): $^1$H NMR (500 MHz, CDCl$_3$): δ 8.57 (dd, 1H, J=1.3, 4.8 Hz), 8.47 (d, 1H, J=2.3 Hz), 7.56 (m, 1H), 7.30 (dd, 1H, J=4.8, 7.8 Hz), 6.03 (s, 1H), 3.59 (s, 3H), 2.22 (d, 3H, J=0.9 Hz),

Step B: Preparation of methyl 3-methyl-4-nitro-3-pyridin-3-ylbutanoate (i-7b)

A solution of i-7a (318 mg, 1.80 mmol), nitromethane (194 μL, 3.59 mmol) and cesium carbonate (526 mg, 1.62 mmol) in DMSO (8.90 mL) was heated in a sealed tube within a microwave reactor at 140° C. for 25 min. The reaction mixture was cooled to rt, poured into satd. aq. NH$_4$Cl and extracted with EtOAc. The combined organics were washed with brine, dried (sodium sulfate) and concentrated in vacuo. Purification of the crude residue by flash chromatography on silica gel (gradient elution; 10%-60% EtOAc/hexanes as eluent) afforded the title compound i-7b. tri/z (ES) 239 (MH)$^+$. $^1$H NMR (500 MHz, CDCl$_3$): δ 8.66 (d, 1H, J=2.5 Hz), 8.56 (dd, 1H, J=1.5, 4.7 Hz), 7.67 (m, 1H), 7.33 (dd, 1H, J=4.8, 8.2 Hz), 4.96 (m, 2H), 3.64 (s, 3H), 2.98 (m, 2H), 1.70 (s, 3H).

Step C: Preparation of 4-methyl-4-pyridin-3-ylpyrrolidin-2-one (i-7c)

i-7b (75.0 mg, 0.315 mmol) in methanol (7.50 mL) was saturated with hydrogen (1 Atm.) and passed through a column of Pd—C using an H-Cube flow apparatus (1.0 mL/min). The column was rinsed with hydrogen-saturated methanol (25.0 mL), and the combined organics were concentrated in vacuo. The resulting crude residue was dissolved in EtOH (3.50 mL) and heated to reflux. After 2 h, the reaction mixture was concentrated in vacuo to afford the title compound i-7c. m/z (ES) 177 (MH)$^+$.

Step D: Preparation of 3-(3-methylpyrrolidin-3-yl)pyridine (i-7d)

A solution of i-7c (55.5 mg, 0.315 mmol) and borane-THF complex (1.26 mL of a 1.0 M THF solution, 1.26 mmol) in THF (1.50 mL) was heated in a sealed tube to 60° C. After 2 h, the reaction mixture was cooled to rt, and the excess borane was quenched with 1.0 M HCl. The resulting mixture was poured into 1.0 N NaOH, saturated with solid NaCl, and extracted with EtOAc. The combined organics were dried (sodium sulfate) and concentrated in vacuo to afford the title compound i-7d. m/z (ES) 163 (MH)$^+$.

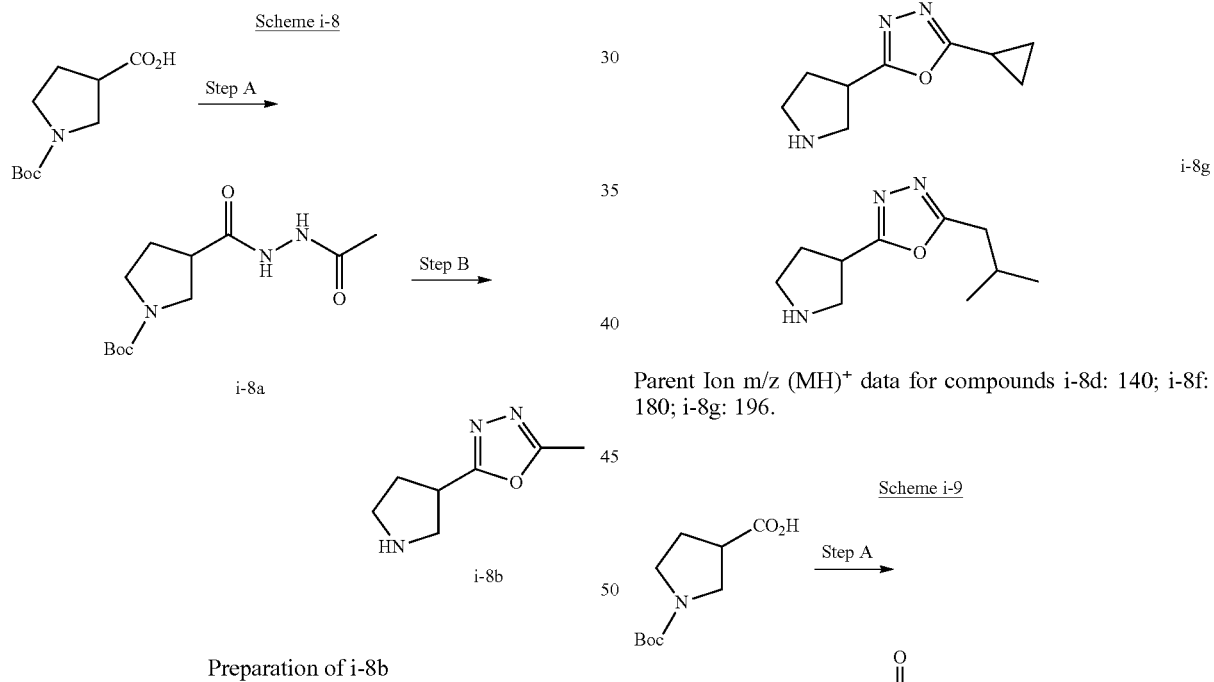

Preparation of i-8b

Step A: Preparation of tert-butyl 3-[(2-acetylhydrazino)carbonyl]pyrrolidine-1-carboxylate (i-8a)

Isobutyl chloroformate (152 μL, 1.16 mmol) was added to a stirred solution of 1-(tert-butoxycarbonyl)pyrrolidine-3-carboxylic acid (237 mg, 1.10 mmol) and 4-methylmorpholine (182 μL, 1.65 mmol) in THF (5.50 mL) at −78° C. After 15 min, added acetic hydrazide (2.0 mg, 1.10 mmol), and the resulting mixture was warmed slowly to rt. After 1 h, the reaction mixture was quenched with 0.5 M HCl and extracted with EtOAc. The combined organics were dried (sodium sulfate) and concentrated in vacuo to afford the title compound i-8a. m/z (ES) 272 (MH)$^+$.

Step B: Preparation of 2-methyl-5-pyrrolidin-3-yl-1,3,4-oxadiazole (i-8b)

A solution of i-8a (299 mg, 1.10 mmol) and phosphorous oxychloride (123 μL, 1.32 mmol) in acetonitrile (5.50 mL) was heated to reflux. After 1.5 h, the reaction mixture was cooled to rt and concentrated in vacuo to afford the title compound i-8b. m/z (ES) 154 (MH)$^+$.

Following procedures similar to those described for the preparation of intermediate i-8b, the following compounds can be prepared.

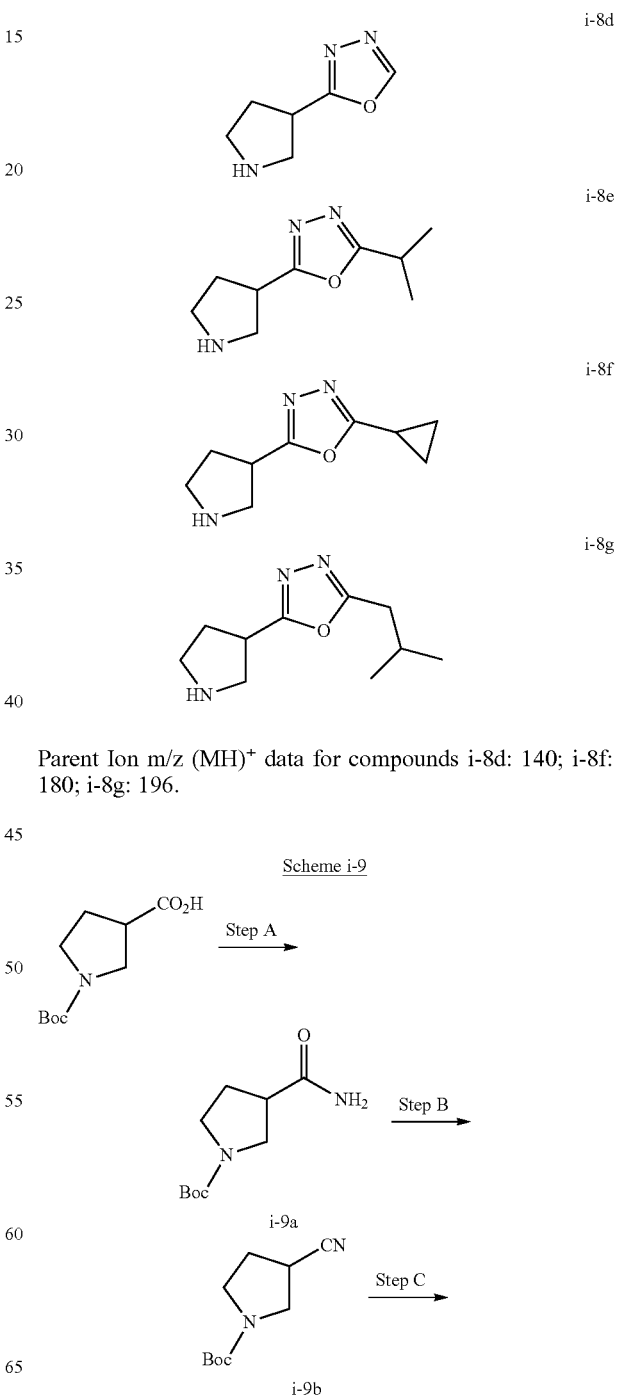

Parent Ion m/z (MH)$^+$ data for compounds i-8d: 140; i-8f: 180; i-8g: 196.

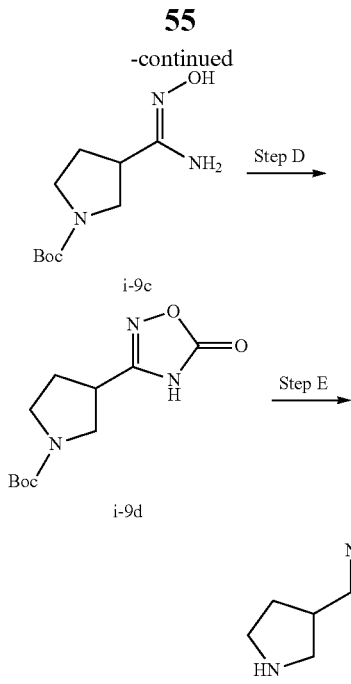

reaction mixture was quenched with satd. aq. NH₄Cl and extracted with EtOAc. The combined organics were washed with brine, dried (sodium sulfate) and concentrated in vacuo. Purification of the crude residue by flash chromatography on silica gel (gradient elution; 0%-25% EtOAc/hexanes as eluent) afforded the title compound i-9d. m/z (ES) 256 (MH)⁺.

Step E: Preparation of 3-pyrrolidin-3-yl-1,2,4-oxa-diazol-5(4H)-one (i-9e)

i-9e was prepared following procedures similar to those described for the preparation of i-4-c, substituting i-9d for i-4-b. m/z (ES) 156 (MH)⁺.

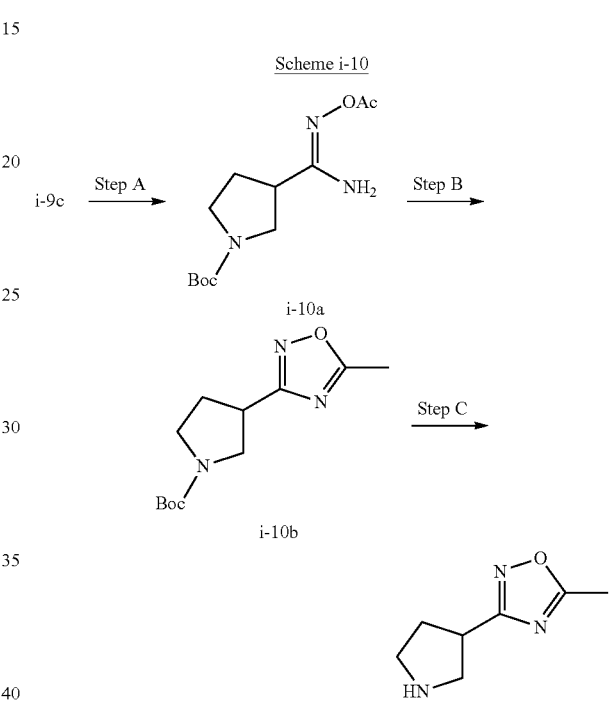

Preparation of i-9e

Step A: Preparation of tert-butyl 3-(aminocarbonyl)pyrrolidine-1-carboxylate (i-9a)

i-9a was prepared following procedures similar to those described for the preparation of i-8a, substituting methanolic ammonia for acetic hydrazide. m/z (ES) 215 (MH)⁺.

Step B: Preparation of tert-butyl 3-cyanopyrrolidine-1-carboxylate (i-9b)

Cyanuric chloride (214 mg, 1.16 mmol) was added to a stirred solution of i-9a (249 mg, 1.16 mmol) m DMF (5.80 mL) at 0° C. After 2 h, the reaction mixture was quenched with satd. aq. NaHCO₃ and extracted with EtOAc. The combined organics were washed with 1.0 N NaOH and brine, dried (sodium sulfate) and concentrated in vacuo to afford the title compound i-9b. m/z (ES) 197 (MH)⁺. ¹H NMR (500 MHz, CDCl₃): δ 3.40-3.80 (m, 4H), 3.11 (m, 1H), 2.28 (m, 2H), 1.49 (s, 9H).

Step C: Preparation of tert-butyl 3-[(Z)-amino(hydroxyimino)methyl]pyrrolidine-1-carboxylate (i-9c)

A solution of i-9b (228 mg, 1.16 mmol) and hydroxylamine (213 μL of a 50% w/v aq. solution, 3.48 mmol) in EtOH (5.80 mL) was heated to reflux. After 2 h, the reaction mixture was cooled to rt and concentrated in vacuo to afford the title compound i-9c. m/z (ES) 230 (MH)⁺.

Step D: Preparation of tert-butyl 3-(5-oxo-4,5-dihydro-1,2,4-oxadiazol-3-yl)pyrrolidine-1-carboxylate (i-9d)

Pyridine (29.0 μL, 0.360 mmol) was added to a stirred solution of i-9c (83.0 mg, 0.362 mmol) and triphosgene (193 mg, 0.652 mmol) in DCM (1.80 mL) at −78° C., and the resulting mixture was allowed to warm to rt. After 12 h, the Preparation of i-10c Step A: Preparation of tert-butyl 3-[[(acetyloxy)imino](amino)methyl]pyrrolidine-1-carboxylate (i-10a)

Acetic anhydride (36.2 μL, 0.384 mmol) was added to a stirred solution of i-9c (80.0 mg, 0.349 mmol) and triethylamine (68.0 μL, 0.488 mmol) in DCM (1.75 mL) at rt. After 1 h, the reaction mixture was quenched with satd. aq. NH₄Cl and extracted with EtOAc. The combined organics were washed with satd. aq. NaHCO₃ and brine, dried (sodium sulfate) and concentrated in vacuo to afford the title compound i-10a. m/z (ES) 272 (MH)⁺.

Step B: Preparation of tert-butyl 3-(5-methyl-1,2,4-oxadiazol-3-yl)pyrrolidine-1-carboxylate (i-10b)

A stirred solution of i-10a (95.0 mg, 0.349 mmol) in xylenes (3.50 mL) was heated to 120° C. After 12 h, the reaction mixture was concentrated in vacuo to afford the title compound i-10b. m/z (ES) 254 (MH)⁺.

Step C: Preparation of 5-methyl-3-pyrrolidin-3-yl-1,2,4-oxadiazole (i-10c)

i-10c was prepared following procedures similar to those described for the preparation of i-4-c, substituting i-10b for i-4-b. m/z (ES) 154 (MH)$^+$.

Following procedures similar to those described for the preparation of intermediate i-10c, the following compounds can be prepared.

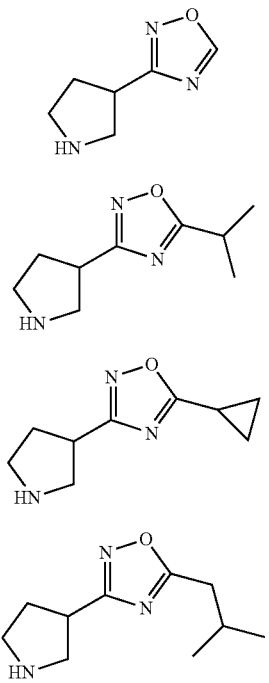

and pTSA (95.0 mg, 0.500 mmol) in toluene (50.0 mL) was heated to 95° C. After 10 h, the reaction mixture was cooled to rt, poured into satd. aq. NaHCO$_3$ and extracted with EtOAc. The combined organics were washed with brine, dried (sodium sulfate) and concentrated in vacuo to afford the title compound i-11a. m/z (ES) 239 (MH)$^+$. $^1$H NMR (500 MHz, CDCl$_3$): δ 8.23 (s, 2H), 4.84 (m, 1H), 3.50-3.70 (m, 4H), 2.50 (m, 1H), 2.22 (m, 1H), 1.51 (s, 9H).

Step B: Preparation of 4-pyrrolidin-3-yl-4H-1,2,4-triazole (i-11b)

i-11b was prepared following procedures similar to those described for the preparation of i-4-c, substituting i-11a for i-4-b. m/z (ES) 139 (MH)$^+$.

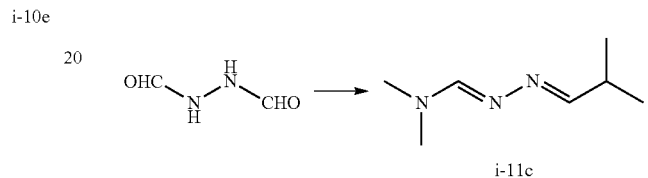

Preparation of N'-[(1E)-(dimethylamino)methylene]-N,N-dimethylhydrazonoformamide (i-11c)

Thionyl chloride (41.4 mL, 568 mmol) was added to a stirred solution of N-formylformic hydrazide (20.0 g, 227 mmol) in DMF (227 mL) at 0° C., and the resulting mixture was allowed to warm to rt. After 72 h, the reaction mixture was diluted with water, quenched with solid sodium carbonate and extracted with DCM. The combined organics were dried (sodium sulfate) and concentrated in vacuo to afford the title compound i-11c. $^1$H NMR (500 MHz, CDCl$_3$): δ 7.77 (s, 2H), 2.93 (s, 6H).

Scheme i-11

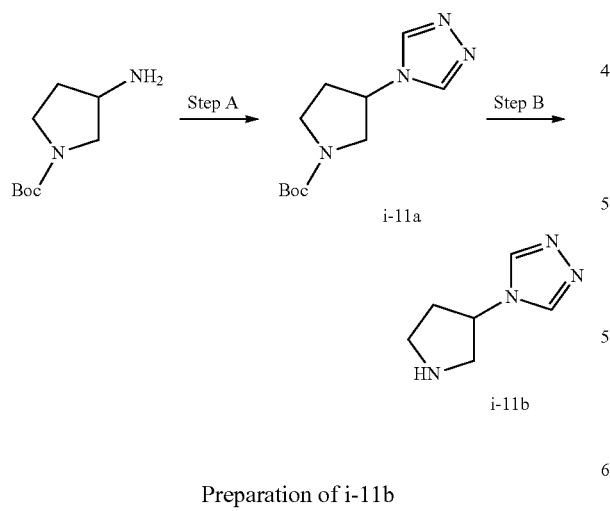

Preparation of i-11b

Step A: Preparation of tert-butyl 3-(4H-1,2,4-triazol-4-yl)pyrrolidine-1-carboxylate (i-11a)

A stirred solution of tert-butyl 3-aminopyrrolidine-1-carboxylate (848 μL, 5.00 mmol), i-11c (711 mg, 5.00 mmol)

Scheme i-12

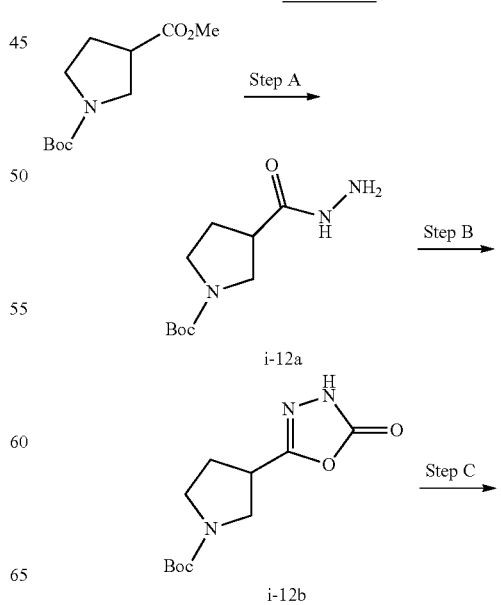

-continued

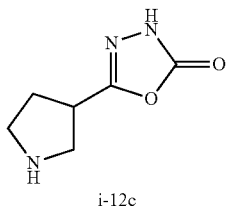

i-12c

Preparation of i-12c

Step A: Preparation of tert-butyl 3-(hydrazinocarbonyl)pyrrolidine-1-carboxylate (i-12a)

A solution of 1-tert-butyl 3-methylpyrrolidine-1,3-dicarboxylate (1.00 equiv.) and hydrazine (excess of 50% aq. solution) in ethanol (0.2 M final conc.) is heated to reflux. After the reaction is deemed complete, the reaction mixture is cooled to rt and partially concentrated. The resulting mixture is diluted with EtOAc, and the resulting organics are washed with water and brine, dried (sodium sulfate) and concentrated in vacuo to afford the title compound i-12a.

Step B: Preparation of tert-butyl 3-(5-oxo-4,5-dihydro-1,3,4-oxadiazol-2-yl)pyrrolidine-1-carboxylate (i-12b)

Phosgene (1.50 equiv. of a 20% toluene solution) is added to a solution of i-12a (1.00 equiv.) and pyridine (4.00 equiv.) in DCM (0.1 M final conc.) at −78° C. After the reaction is deemed complete, the reaction mixture is quenched with satd. aq. NaHCO$_3$ and extracted with EtOAc. The combined organics are washed with brine, dried (sodium sulfate) and concentrated in vacuo to afford the title compound i-12b.

Step C: Preparation of 5-pyrrolidin-3-yl-1,3,4-oxadiazol-2(3H)-one (i-12c)

i-12c can be prepared following procedures similar to those described for the preparation of i-4-c, substituting i-12b for i-4-b.

Scheme i-13

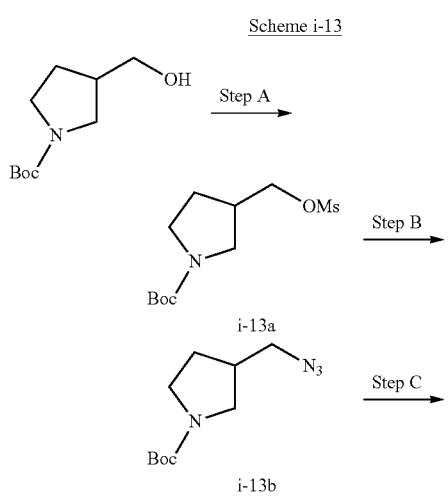

-continued

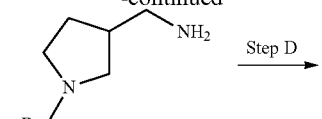

i-13c

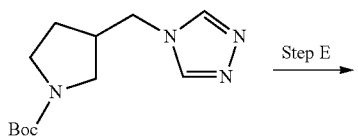

i-13d

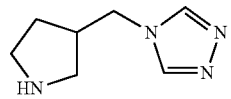

i-13e

Preparation of i-13e

Step A: Preparation of tert-butyl 3-{[(methylsulfonyl)oxy]methyl}pyrrolidine-1-carboxylate (i-13a)

Mesyl chloride (106 μL, 1.37 mmol) was added to a stirred solution of tert-butyl 3-(hydroxymethyl)pyrrolidine-1-carboxylate (250 mg, 1.242 mmol) and triethylamine (225 μL, 1.62 mmol) in DCM (13.0 mL) at 0° C. After 20 min, the reaction mixture was diluted with DCM, washed with brine, dried (sodium sulfate) and concentrated in vacuo to afford the title compound i-13a. $^1$H NMR (500 MHz, CDCl$_3$): δ 4.19 (m, 2H), 3.20-3.60 (m, 3H), 3.17 (m, 1H), 3.05 (s, 3H), 2.65 (m, 1H), 2.07 (m, 1H), 1.74 (m, 1H), 1.48 (s, 9H).

Step B: Preparation of tert-butyl 3-(azidomethyl)pyrrolidine-1-carboxylate (i-13b)

A stirred suspension of i-13a (347 mg, 1.24 mmol) and sodium azide (322 mg, 4.97 mmol) in DMSO (6.00 mL) was heated to 50° C. overnight. The reaction mixture was cooled to rt, poured into water and extracted with EtOAc. The combined organics were washed with brine, dried (sodium sulfate) and concentrated in vacuo to afford the title compound i-13b. $^1$H NMR (500 MHz, CDCl$_3$): δ 3.30-3.65 (m, 6H), 3.08 (m, 1H), 2.45 (m, 1H), 2.04 (m, 1H), 1.65 (m, 1H), 1.49 (s, 9H).

Step C: Preparation of tert-butyl 3-(aminomethyl)pyrrolidine-1-carboxylate (i-13c)

A stirred suspension of i-13b (105 mg, 0.464 mmol) and 10 wt. % palladium on carbon (49.0 mg, 0.046 mmol) in methanol (4.50 mL) was stirred under hydrogen (1 Atm.) at rt for 1 h. The reaction mixture was diluted with EtOAc and filtered through a short column of Celite®. The Celite® column was rinsed with additional portions of EtOAc, and the combined organic fractions were dried (sodium sulfate) and concentrated in vacuo to afford the title compound i-13c. m/z (ES) 201 (MH)$^+$.

Step D: Preparation of tert-butyl 3-(4H-1,2,4-triazol-4-ylmethyl)pyrrolidine-1-carboxylate (i-13d)

i-13d was prepared following procedures similar to those described for the preparation of i-11a, substituting i-13c for tert-butyl 3-aminopyrrolidine-1-carboxylate. m/z (ES) 253 (MH)$^+$.

Step E: Preparation of 4-(pyrrolidin-3-ylmethyl)-4H-1,2,4-triazole (i-13e)

i-13e was prepared following procedures similar to those described for the preparation of i-4-c, substituting i-13d for i-4-b. m/z (ES) 153 (MH)+.

Scheme i-14

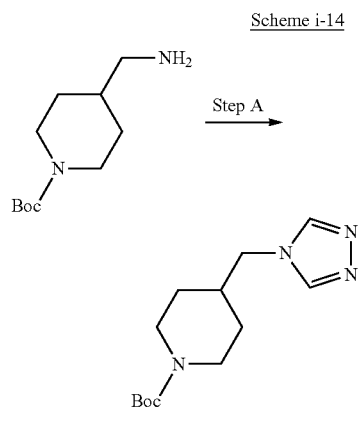

Preparation of 4-(4H-1,2,4-triazol-4-ylmethyl)piperieine (i-14b)

i-14b was prepared from tert-butyl 4-(aminomethyl)piperidine-1-carboxylate in two steps by following procedures, described for the preparation of i-11a, substituting tert-butyl 4-(aminomethyl)piperidine-1-carboxylate for tert-butyl 3-aminopyrrolidine-1-carboxylate in Step A. The product of this reaction, i-14a was subjected to conditions described for the preparation of i-4-c, substituting i-14a for i-4-b. m/z (ES) 167 (MH)+.

Scheme i-15

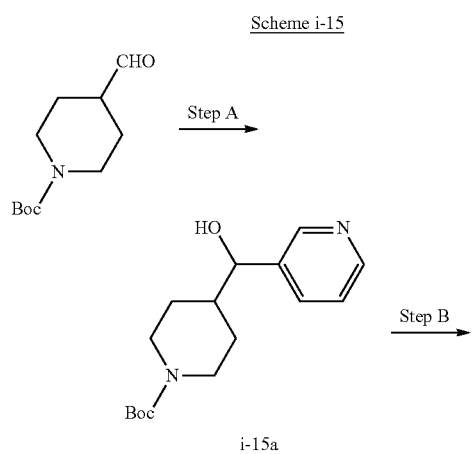

Preparation of i-15d

Step A: Preparation of tert-butyl 4-[hydroxy(pyridin-3-yl)methyl]piperidine-1-carboxylate (i-15a)

3-Bromopyridine (116 µL, 1.20 mmol) was added slowly dropwise to a stirred suspension of n-butyllithium (480 µL of a 2.5 M hexanes solution, 1.20 mmol) in THF (1.00 mL) at −78° C. After 15 min, tert-butyl 4-formylpiperidine-1-carboxylate (213 mg, 1.00 mmol) was added, and the resulting mixture was allowed to stir at −78° C. After 1 h, the reaction was quenched with 1.0 M HCl, poured into satd. aq. NaHCO$_3$ and extracted with EtOAc. The combined organics were washed with brine, dried (sodium sulfate) and concentrated in vacuo. Purification of the crude residue by flash chromatography on silica gel (gradient elution; 10%-100% EtOAc/DCM as eluent) afforded the title compound i-15a. $^1$H NMR (500 MHz, CDCl$_3$): δ 8.55 (m, 2H), 7.70 (d, 1H, J=8.0 Hz), 7.32 (dd, 1H, J=4.9, 7.4 Hz), 4.49 (m, 1H), 4.15 (m, 4H), 2.65 (m, 2H), 1.83 (m, 1H), 1.79 (m, 1H), 1.46 (s, 9H), 1.31 (m, 1H).

Step B: Preparation of tert-butyl 4-[(acetyloxy)(pyridin-3-yl)methyl]piperidine-1-carboxylate (i-15b)

Acetic anhydride (204 µL, 2.16 mmol) was added to a stirred solution of i-15a (158 mg, 0.540 mmol) and triethylamine (377 µL, 2.70 mmol) in DCE (2.70 mL). After 6 h, the reaction mixture was quenched with 0.5 M HCl and extracted with DCM. The combined organics were washed with satd. aq. NaHCO$_3$ and brine, dried (sodium sulfate) and concentrated in vacuo to afford the title compound i-15b. m/z (ES) 335 (MH)+.

Step C: Preparation of tert-butyl 4-[(pyridin-3-yl)methyl]piperidine-1-carboxylate (i-15c)

A stirred suspension of i-15b (181 mg, 0.540 mmol), ammonium formate (141 pt, 2.87 mmol) and 10 wt. % palladium on carbon (57.0 mg, 0.054 mmol) in methanol (5.50 mL) was stirred at rt for 12 h. The reaction mixture was diluted with methanol and filtered through a short column of Celite®. The Centel) column was rinsed with additional portions of methanol, and the combined organic fractions were concentrated in vacuo to afford the title compound i-15c. m/z (ES) 277 (MH)$^+$.

Step D: Preparation of 3-(piperidin-4-ylmethyl)pyridine (i-15d)

i-15d was prepared following procedures similar to those described for the preparation of i-4-c, substituting i-15c for i-4-b. m/z (ES) 177 (MH)$^+$.

Following procedures similar to those described above for preparing intermediate i-15d, the following additional intermediates can be prepared.

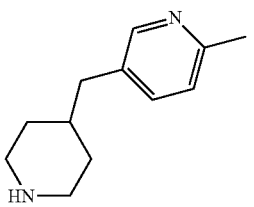
i-15e

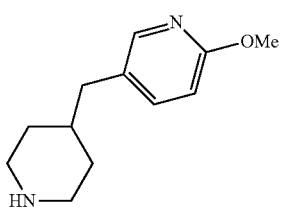
i-15f

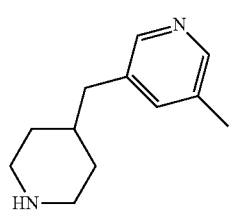
i-15g

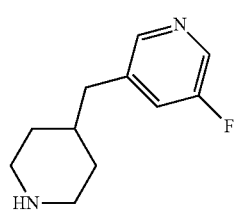
i-15h

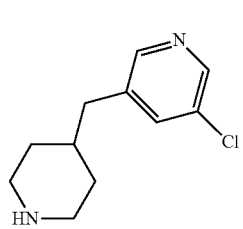
i-15i

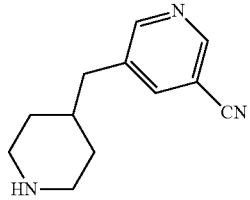
i-15j

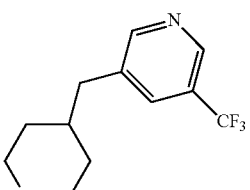
i-15k

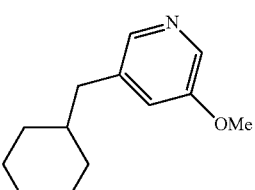
i-15l

Scheme i-16

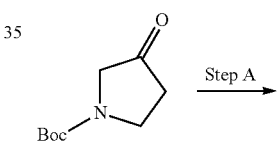

Step A →

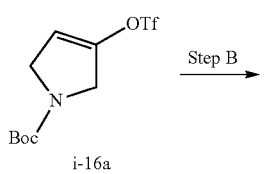
i-16a

Step B →

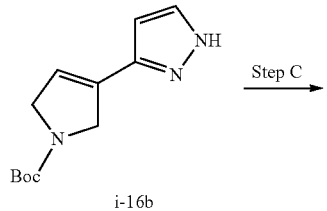
i-16b

Step C →

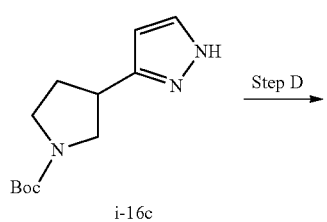
i-16c

Step D →

-continued

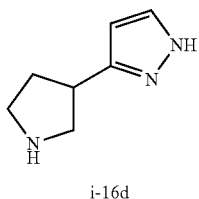

i-16d

Preparation of i-16d

Step A: Preparation of tert-butyl 3-{[(trifluoromethyl)sulfonyl]oxy}-2,5-dihydro-1H-pyrrole-1-carboxylate (i-16a)

Lithium hexamethyldisilazane (5.50 mL of a 1.0 M ether solution, 5.50 mmol) was added to a solution of tert-butyl 3-oxopyrrolidine-1-carboxylate (925 mg, 5.00 mmol) in THF (15.0 mL) at −78° C., After 1 h, a solution of 2-[N,N-bis(trifluoromethylsulfonyl)amino]-5-chloropyridine (2.16 g, 5.50 mmol) in THF (10.0 mL) was added dropwise, and the resulting mixture was allowed to stir at −78° C. After 2 h, the reaction mixture was quenched with satd. aq. NH$_4$Cl and extracted with EtOAc, The combined organics were washed with water and brine, dried (sodium sulfate), and concentrated in vacuo. Purification of the crude residue by flash chromatography on silica gel (gradient elution; 1%-2% EtOAc/petroleum ether as eluent) afforded the title compound i-16a.

Step B: Preparation of tert-butyl 3-(1H-pyrazol-3-yl)-2,5-dihydro-1H-pyrrole-1-carboxylate (i-16b)

A mixture of i-16a (317 mg, 1.00 mmol), 3-pyrazole boronic acid (123 mg, 1.10 mmol), [1,1'-bis(diphenylphosphino)ferrocene]dichloropalladium (II)-DCM complex (25.0 mg, 0.031 mmol) and sodium carbonate (2.00 mL of a 2.0 M aq. solution, 2.00 mmol) in dioxane (6.00 mL) was heated to 90° C. After 4 h, the reaction mixture was cooled to rt and filtered through a short column of Celite®. The Celite® column was rinsed with EtOAc, and the combined organics were washed with water and brine, dried (sodium sulfate) and concentrated in vacuo. Purification of the crude residue by flash chromatography on silica gel (gradient elution; 0%-23% EtOAc/hexanes as eluent) afforded the title compound i-16b. m/z (ES) 236 (MH)$^+$.

Step C: Preparation of tert-butyl 3-(1H-pyrazol-3-yl)-pyrrolidine-1-carboxylate (i-16c)

A stirred suspension of i-16b (165 mg, 0.700 mmol) and 10% palladium on carbon (20.0 mg, 0.022 mmol) in methanol (20.0 mL) was stirred under hydrogen (1 Atm.) at rt. After 1.5 h, the reaction mixture was diluted with methanol and filtered through a short column of Celite®. The Celite® column was rinsed with additional portions of methanol, and the combined organic fractions were concentrated in vacuo to afford the title compound i-16c. m/z (ES) 238 (MH)$^+$.

Step D: Preparation of 3-pyrrolidin-3-yl-1H-pyrazole (i-16d)

i-16d was prepared following procedures similar to those described for the preparation of i-4-c, substituting i-16c for i-4-b. m/z (ES) 138 (MH)$^+$.

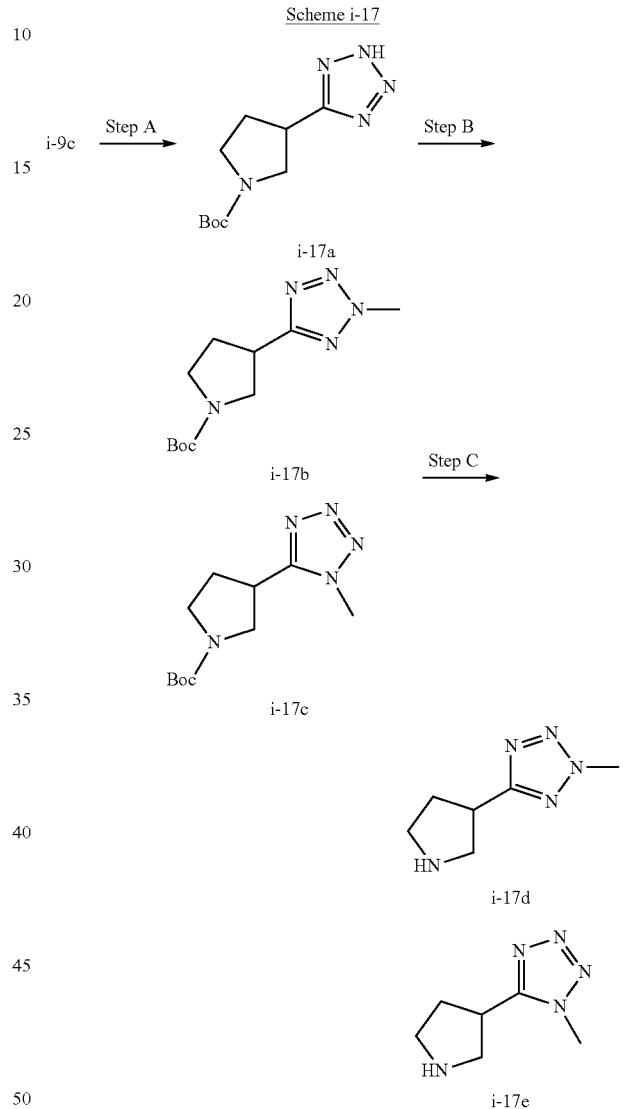

Preparation of i-17d and i-17e

Step A: Preparation of tert-butyl 3-(2H-tetrazol-5-yl)pyrrolidine-1-carboxylate (i-17a)

A mixture of i-9c (200 mg, 1.00 mmol), sodium azide (195 mg, 3.00 mmol) and ammonium chloride (109 mg, 3.00 mmol) in DMF (3.00 mL) was heated to 120° C. After 18 h, the reaction mixture was cooled to rt, and 1.0 M HCl was added to the stirring mixture. After an additional 30 min, the reaction mixture was diluted with water and extracted with DCM. The combined organics were washed with brine, dried (sodium sulfate) and concentrated in vacuo to afford the title compound i-17a. m/z (ES) 240 (MH)$^+$.

Step B: Preparation of tert-butyl 3-(2-methyl-2H-tetrazol-5-yl)pyrrolidine-1-carboxylate i-17b)

Iodomethane (37.0 µL, 0.600 mmol) was added to a stirred solution of i-17a (120 mg, 0.500 mmol) and potassium carbonate (97.0 mg, 0.700 mmol) in acetonitrile (5.00 mL), and the resulting mixture was heated to reflux. After 3 h, the reaction mixture was cooled to rt, filtered and concentrated in vacuo. The crude residue was dissolved in DCM, and the organics were washed with water and brine, dried (sodium sulfate) and concentrated in vacuo to afford the title compound, i-17b, and regioisomer, i-17c. m/z (ES) 254 (MH)$^+$.

Step C: Preparation of 2-methyl-5-pyrrolidine-3-yl-2H-tetrazole (i-17d)

i-17d and i-17e were prepared following procedures similar to those described for the preparation of i-4-c, substituting i-17b and i-17c, respectively, for i-4-b. m/z (ES) 154 (MH)$^+$.

Following procedures similar to those described above for preparing intermediates i-17d and i-17e, the following additional intermediates can be prepared from i-17a.

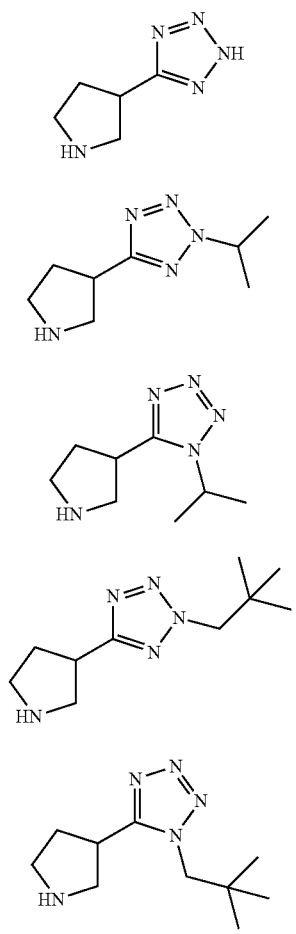

Parent Ion m/z (MH)$^+$ data for compounds i-17f: 140; i-17g: 182; i-17i: 210.

Scheme i-18

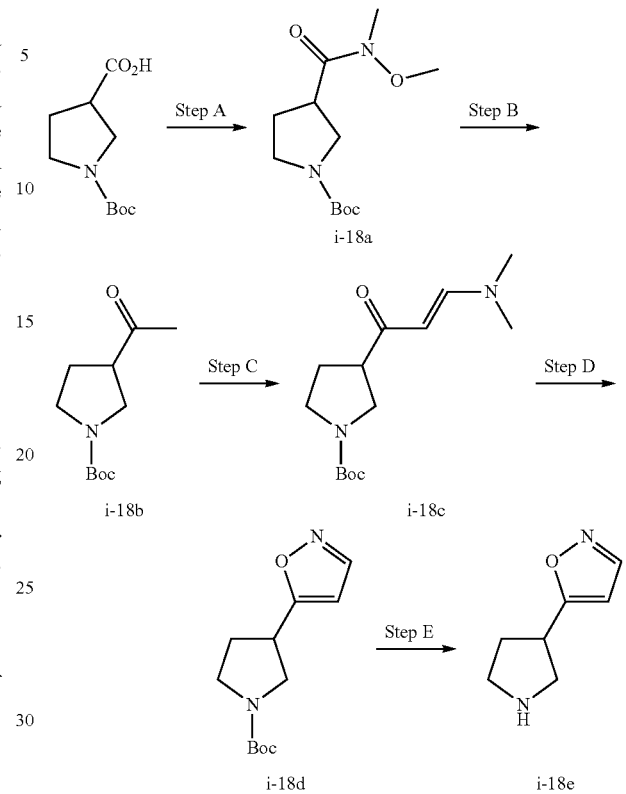

Preparation of i-18e

Step A: Preparation of tert-butyl 3-{[methoxy(methyl)amino]carbonyl}pyrrolidine-1-carboxylate (i-18a)

HATU (4.56 g, 12.0 mmol) was added to 1-(tert-butoxycarbonyl)pyrrolidine-3-carboxylic acid (2.15 g, 10.0 mmol), N-methoxy-N-methylamine hydrochloride (1.16 g, 12.0 mmol), and triethylamine (4.18 mL, 30.0 mmol) in DCM (50.0 mL), and the resulting mixture was allowed to stir at rt. After 12 h, the reaction mixture was diluted with DCM, and the combined organics were washed with water and brine, dried (sodium sulfate) and concentrated in vacuo to afford the title compound i-18a. m/z (ES) 259 (MH)$^+$.

Step B: Preparation of tert-butyl 3-acetylpyrrolidine-1-carboxylate (i-18b)

Methyl magnesium bromide (750 µL of a 3.0 M ether solution, 2.25 mmol) was added to a stirred solution of i-18a (258 mg, 1.00 mmol) in THF (2.50 mL) at −78° C., and after 1 h, the reaction mixture was warmed slowly to 0° C. After 3 h, the reaction mixture was quenched with satd. aq. NH$_4$Cl, and the resulting mixture was extracted with EtOAc. The combined organics were washed with water and brine, dried (sodium sulfate) and concentrated in vacuo. Purification of the crude residue by flash chromatography on silica gel (gradient elution; 10%-20% EtOAc/petroleum ether as eluent) afforded the title compound i-18b. m/z (ES) 214 (MH)$^+$.

Step C: Preparation of tert-butyl 3-[(2E)-3-(dimethylamino)prop-2-enoyl]pyrrolidine-1-carboxylate (i-18c)

A stirred solution of i-18b (213 mg, 1.00 mmol) and N,N,-dimethylformamide dimethylacetal (260 mg, 2.00 mmol) was heated to 85° C. After 8 h, the reaction mixture was cooled to rt and concentrated in vacuo to afford the title compound i-18c.

Step D: Preparation of tert-butyl 3-isoxazol-5-ylpyrrolidine-1-carboxylate (i-18d)

A stirred solution of i-18c (80.0 mg, 0.310 mmol) and hydroxylamine hydrochloride (22.9 mg, 0.330 mmol) in methanol (3.00 mL) was heated to reflux. After 7 h, the reaction mixture was cooled to rt, poured into water and extracted with EtOAc. The combined organics were washed with brine, dried (sodium sulfate) and concentrated in vacuo. Purification of the crude residue by preparative thin-layer chromatography on silica gel (50% EtOAc/petroleum ether as eluent) afforded the title compound i-18c. m/z (ES) 239 (MH)$^+$.

Step E: Preparation of 5-pyrrolidin-3-ylisoxazole (i-18e)

i-18e was prepared following procedures similar to those described for the preparation of i-4c, substituting i-18d for i-4b. m/z (ES) 139 (MH)$^+$.

After 30 min, the reaction mixture was concentrated in vacuo, and the residue was dissolved in EtOAc. The organics were washed with water and brine, dried (magnesium sulfate) and concentrated in vacuo. Purification of the crude residue by preparative thin-layer chromatography on silica gel (30% EtOAc/petroleum ether as eluent) afforded the title compound i-19a. NMR (400 MHz, CDCl$_3$): δ 4.12 (s, 1H), 3.98 (s, 1H), 3.65-3.39 (m, 4H), 2.23-2.10 (m, 2H), 1.70-1.60 (b, 1H), 1.48 (s, 9H).

Step B: Preparation of tert-butyl 3-(2-methyl-1,3-thiazol-4-yl)pyrrolidine-1-carboxylate (i-19b)

A mixture of i-19b (60.0 mg, 0.210 mmol), thioacetamide (31.5 mg, 0.420 mmol) and sodium bicarbonate (35.8 mg, 0.420 mmol) in ethanol (1.00 mL) were heated in a sealed tube within a microwave reactor at 120° C. for 15 min. The reaction mixture was cooled to rt, concentrated in vacuo, and the resulting residue was partitioned between EtOAc and water. The layers were separated, and the organics were washed with satd. aq. NaHCO$_3$ and brine, dried (sodium sulfate) and concentrated in vacuo. Purification of the crude residue by preparative thin-layer chromatography on silica gel (50% EtOAc/petroleum ether as eluent) afforded the title compound i-19b.

Step C: Preparation of 2-meth 1-4-pyrrolidin-3-yl-1,3-thiazole (i-19c)

i-19c was prepared following procedures similar to those described for the preparation of i-4c, substituting i-19b for i-4b. m/z (ES) 169 (MH)$^+$.

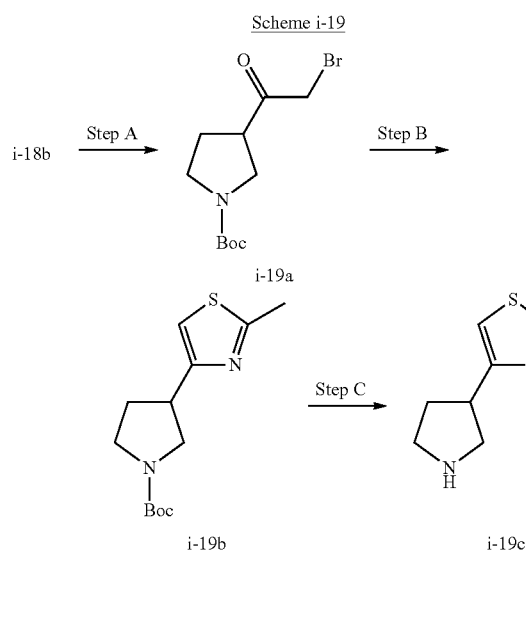

Preparation of i-19c

Step A: Preparation of tert-butyl 3-(bromoacetyl)pyrrolidine-1-carboxylate (i-19a)

Chlorotrimethylsilane (1.13 mL, 10.6 mmol) was added dropwise to a stirred solution of lithium hexamethyldisilylamide (1.20 ml of a 1.0 M THF solution, 1.20 mmol) in THF (40.0 mL) at −78° C. After 5 min, a solution of i-18b (213 mg, 1.00 mmol) in THF (4.00 mL) was added dropwise, and the resulting mixture was warmed to 0° C. over 30 min, at which point N-bromosuccinimide (210 mg, 1.21 mmol) was added.

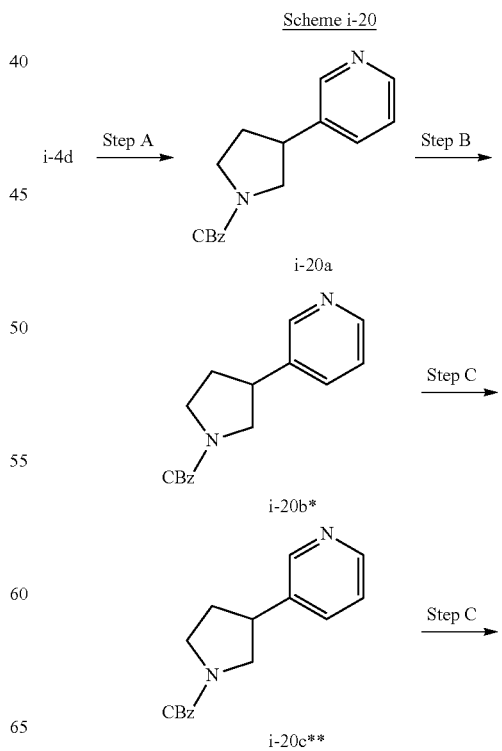

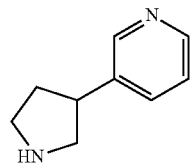

i-20d*

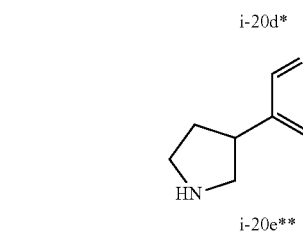

i-20e**

*= the faster eluting enantiomer
**= the slower eluting enantiomer

Preparation of i-20e

Step A: Preparation of benzyl 3-pyridin-3-ylpyrrolidine-1-carboxylate (i-20a)

Benzyl chloroformate (53.6 μL, 0.375 mmol) was added to a stirred solution of i-4d (53.0 mg, 0.356 mmol) and triethylamine (74.8 μL, 0.536 mmol) in DCM (1.80 mL) at rt. After 12 h, the reaction mixture was concentrated in vacuo, and the resulting crude residue was purified by flash chromatography on silica gel (gradient elution; 50%-100% EtOAc/hexane as eluent) afforded the title compound i-20a. $^1$H NMR (500 MHz, CDCl$_3$): δ 8.54 (d, 2H, J=5.7 Hz), 7.57 (d, 1H, J=7.1 Hz), 7.30-7.43 (m, 6H), 5.20 (d, 2H, J=3.4 Hz), 3.98 (m, 1H), 3.71 (m, 1H), 3.55 (m, 1H), 3.44 (m, 2H), 2.36 (m, 1H), 2.04 (m, 1H). m/z (ES) 283 (MH)$^+$.

Step B: Preparation of (i-20b) and (i-20c)

Enantiomers i-20b and i-20c were separated using preparative normal phase chiral HPLC. A solution of i-20a in MeOH was injected onto a CHIRALCEL® OD-H (available from Chiral Technologies, Inc., Exton, Pa.) semi-preparative (250× 20 mm) HPLC column (eluting with 20% MeOH/CO$_2$ with a column temperature of 40° C. at 50 mL/min with UV detection at 220 nm). The enantiomers were separated with the faster eluting enantiomer i-20b having a retention time of 11.64 min and the slower eluting enantiomer i-20c having a retention time of 13.32 min. The separated fractions were concentrated to provide the enantiomers i-20b and i-20c.

Step C: Preparation of 3-pyrrolidin-3-ylpyridine (i-20e)

Palladium on carbon (19.6 mg, 10 wt. % on activated carbon) was added to a solution of i-20b (26.0 mg, 0.092 mmol) in methanol (1.80 mL), and the resulting mixture was hydrogenated (balloon pressure) for 1.5 h. The reaction mixture was filtered through a pad of Celite, and the solid layer was rinsed with EtOAc. The combined filtrate was concentrated in vacuo to afford the title compound i-20d. m/z (ES) 149 (MH)$^+$.

Compound i-20e was prepared following similar procedures to those described above in step C, substituting i-20c for i-20b. m/z (ES) 149 (MH)$^+$.

In the Tables associated with the following Examples, compounds having mass spectral data were synthetically prepared.

Example 1

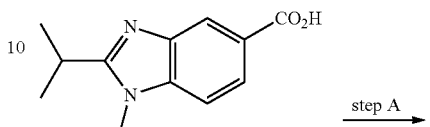

i-1e

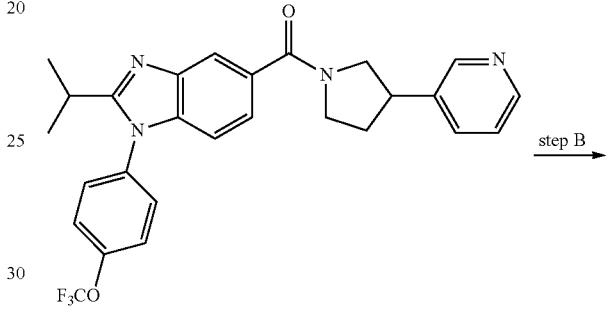

*= the faster eluting enantiomer
**= the slower eluting enantiomer

Step A: Preparation of 2-isopropyl-5-[(3-pyridin-3-ylpyrrolidin-1-yl)carbonyl]-1-[4-(trifluoromethoxy) phenyl]-1H-benzimidazole (1a)

i-4-d (105 mg, 0.710 mmol) was added to a stirred solution of i-1e (231 mg, 0.634 mmol), N-(3-dimethylaminopropyl)-N-ethylcarbodiimide hydrochloride (158 mg, 0.824 mmol) and 1-hydroxybenzotriazole (97.0 mg, 0.634 mmol) in DMF. After 2 h, the reaction mixture was diluted with acetonitrile and water, and the resulting mixture was purified by preparative reversed phase HPLC on YMC Pack Pro C18 stationary phase (CH$_3$CN/H$_2$O as eluent, 0.05% TFA as modifier), followed by lyophilization of the purified fractions afforded the title compound 1a. m/z (ES) 495 (MH)$^+$.

Step B: Preparation of (1b) and (1c)

Enantiomers 1b and 1c were separated using preparative normal phase chiral HPLC. A solution of 1a in MeOH was injected onto a CHIRALCEL® OD-H (available from Chiral Technologies, Inc., Exton, Pa.) semi-preparative (250×20 mm) HPLC column (eluting with 20% MeOH/CO$_2$ with a column temperature of 40° C. at 50 mL/min with UV detection at 220 nm). The enantiomers were separated with the faster eluting enantiomer 1b having a retention time of 9.05 min and the slower eluting enantiomer 1c having a retention time of 11.68 min. The separated fractions were concentrated to provide the enantiomers 1b and 1c. For 1c: m/z (ES) 495 (MH)$^+$.

Following procedures similar to those described for the preparation of compound 1a, the following compounds in Tables 1A, 1B, 1C and 1D can be prepared.
TABLE 1A
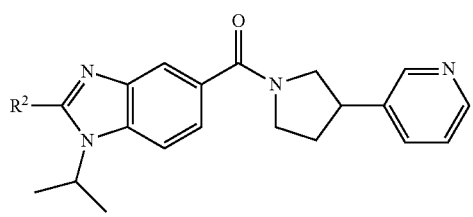
1A
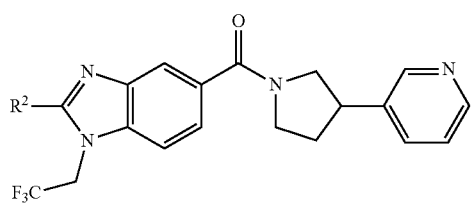
1B
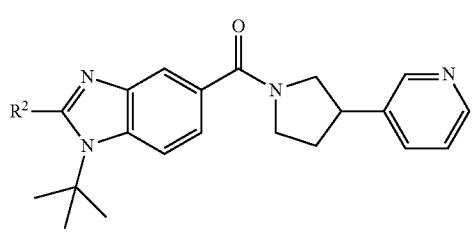
1C
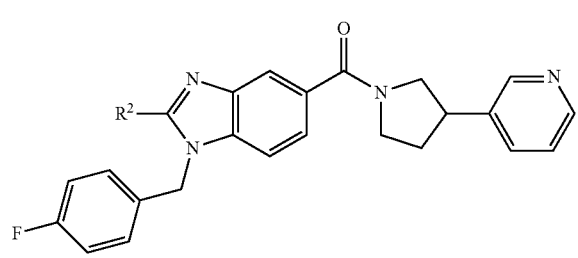
1D
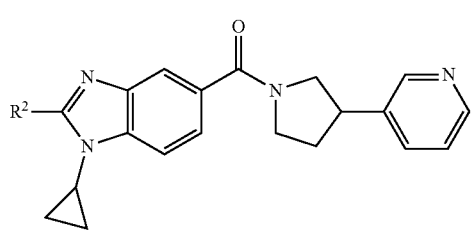
1E
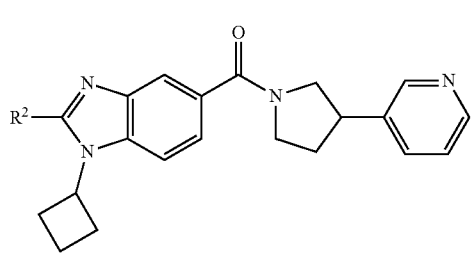
1F
1G TABLE 1A-continued
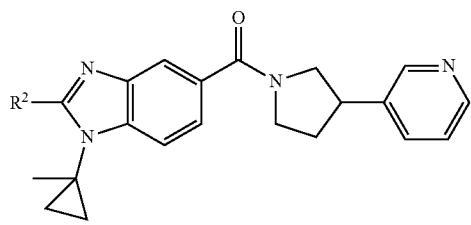
1H
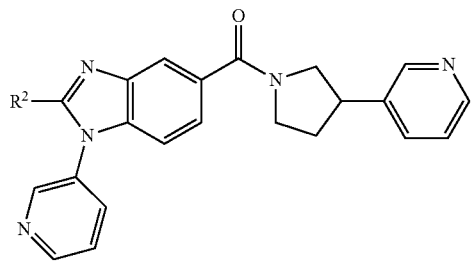
| Ex. 1A | Ex. 1B | Ex. 1C | Ex. 1D | Ex. 1E | Ex. 1F | Ex. 1G | Ex. 1H | $R^2$ |
|---|---|---|---|---|---|---|---|---|
| a | a | a | a | a | a | a | a | Me |
| b | b | b | b | b | b | b | b | $CF_3$ |
| c | c | c | c | c | c | c | c | $^i$Pr |
| d | d | d | d | d | d | d | d | $^i$Bu |
| e | e | e | e | e | e | e | e | $^t$Bu |
| f | f | f | f | f | f | f | f | $^c$Pr |
| g | g | g | g | g | g | g | g | $^c$Bu |
| h | h | h | h | h | h | h | h | 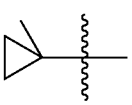 |
| i | i | i | i | i | i | i | i | 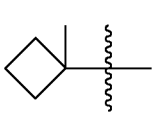 [SMILES: *C1(C)CCC1] |
| j | j | j | j | j | j | j | j | 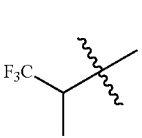 |
| k | k | k | k | k | k | k | k |  |
| l | l | l | l | l | l | l | l | Ph |
| m | m | m | m | m | m | m | m | 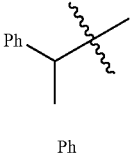 |
| n | n | n | n | n | n | n | n | 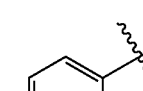 |

| | | | | | | | | |
|---|---|---|---|---|---|---|---|---|
| o | o | o | o | o | o | o | o | 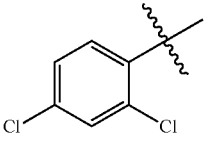 [SMILES: *c1ccc(Cl)cc1Cl] |
| p | p | p | p | p | p | p | p | 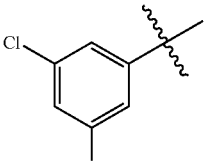 |
| q | q | q | q | q | q | q | q | 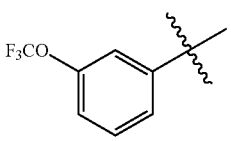 [SMILES: *c1cccc(OC(F)(F)F)c1] |
| r | r | r | r | r | r | r | r | 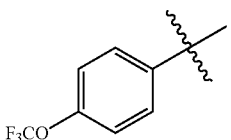 |
| s | s | s | s | s | s | s | s | 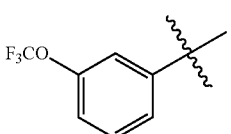 |
| t | t | t | t | t | t | t | t | Bn |
| u | u | u | u | u | u | u | u | 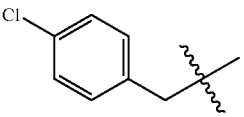 [SMILES: *Cc1ccc(Cl)cc1] |
| v | v | v | v | v | v | v | v | 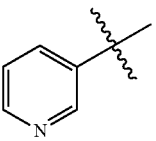 [SMILES: *c1cccnc1] |
| w | w | w | w | w | w | w | w | 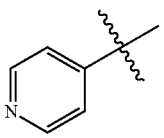 [SMILES: *c1ccncc1] |

Table 1A. Parent Ion m/z (MH)+ data for compounds

For 1Ac: 1,2-diisopropyl-5-[(3-pyridin-3-ylpyrrolidin-1-yl)carbonyl]-1H-benzimidazole: m/z (ES)=377 (MH)+'''

For 1Ak: 1-isopropyl-2-(1-phenylethyl)-5-[(3-pyridin-3-ylpyrrolidin-1-yl)carbonyl]-1H-benzimidazole: m/z (ES)=439 (MH)+

For 1Al: 1-isopropyl-2-phenyl-5-[(3-pyridin-3-ylpyrrolidin-1-yl)carbonyl]-1H-benzimidazole: m/z (ES)=411 (MH)+

For 1Am: 2-(4-fluorophenyl)-1-isopropyl-5-[(3-pyridin-3-ylpyrrolidin-1-yl)carbonyl]-1H-benzimidazole: m/z (ES)=429 (MH)+

For 1Ar: 1-isopropyl-5-[(3-pyridin-3-ylpyrrolidin-1-yl)carbonyl]-2-[4-(trifluoromethoxy)phenyl]-1H-benzimidazole: m/z (ES)=495 (MH)+

(Compound 1Ar is a single enantiomer, for which the absolute stereochemistry was not determined. 1Ar was isolated as the faster eluting enantiomer following chiral HPLC purification.)

For 1As: 2-[3,5-bis(trifluoromethyl)phenyl]-1-isopropyl-5-[(3-pyridin-3-ylpyrrolidin-1-yl)carbonyl]-1H-benzimidazole: m/z (ES)=547 (MH)+

For 1Bl: 2-phenyl-5-[(3-pyridin-3-ylpyrrolidin-1-yl)carbonyl]-1-(2,2,2-trifluoroethyl)-1H-benzimidazole: m/z (ES)=451 (MH)+
For 1Bn: 2-(2,4-difluorophenyl)-5-[(3-pyridin-3-ylpyrrolidin-1-yl)carbonyl]-1-(2,2,2-trifluoroethyl)-1H-benzimidazole: m/z (ES)=487 (MH)+
For 1Bo: 2-(2,4-dichlorophenyl)-5-[(3-pyridin-3-ylpyrrolidin-1-yl)carbonyl]-1-(2,2,2-trifluoroethyl)-1H-benzimidazole: m/z (ES)=519 (MH)+
For 1Bp: 2-(3,5-dichlorophenyl)-5-[(3-pyridin-3-ylpyrrolidin-1-yl)carbonyl]-1-(2,2,2-trifluoroethyl)-1H-benzimidazole: m/z (ES)=519 (MH)+
For 1Bq: 5-[(3-pyridin-3-ylpyrrolidin-1-yl)carbonyl]-1-(2,2,2-trifluoroethyl)-2-[3-(trifluoromethoxy)phenyl]-1H-benzimidazole: m/z (ES)=535 (MH)+
For 1Br: 5-[(3-pyridin-3-ylpyrrolidin-1-yl)carbonyl]-1-(2,2,2-trifluoroethyl)-2-[4-(trifluoromethoxy)phenyl]-1H-benzimidazole: m/z (ES)=535 (MH)+
For 1Bu: 2-(4-chlorobenzyl)-5-[(3-pyridin-3-ylpyrrolidin-1-yl)carbonyl]-1-(2,2,2-trifluoroethyl)-1H benzimidazole: m/z (ES)=499 (MH)+
For 1Bv: 2-pyridin-3-yl-5-[(3-pyridin-3-ylpyrrolidin-1-yl)carbonyl]-1-(2,2,2-trifluoroethyl)-1H-benzimidazole: m/z (ES)=452 (MH)+
For 1Bw: 2-pyridin-4-yl-5-[(3-pyrimidin-5-ylpyrrolidin-1-yl)carbonyl]-1-(2,2,2-trifluoroethyl)-1H-benzimidazole: m/z (ES)=452 (MH)+
For 1Cr: 1-tert-butyl-5-[(3-pyridin-3-ylpyrrolidin-1-yl)carbonyl]-2-[4-(trifluoromethoxy)phenyl]-1H-benzimidazole: m/z (ES)=509 (MH)+
For 1Dl: 1-(4-fluorobenzyl)-2-phenyl-5-[(3-pyridin-3-ylpyrrolidin-1-yl)carbonyl]-1H-benzimidazole: m/z (ES)=477 (MH)+
For 1Dn: 2-(2,4-difluorophenyl)-1-(4-fluorobenzyl)-5-[(3-pyridin-3-ylpyrrolidin-1-yl)carbonyl]-1H-benzimidazole: m/z (ES)=513 (MH)+
For 1Do: 2-(2,4-dichlorophenyl)-1-(4-fluorobenzyl)-5-[(3-pyridin-3-ylpyrrolidin-1-yl)carbonyl]-1H-benzimidazole: m/z (ES)=545 (MH)+
For 1Dp: 2-(3,5-dichlorophenyl)-1-(4-fluorobenzyl)-5-[(3-pyridin-3-ylpyrrolidin-1-yl)carbonyl]-1H-benzimidazole: m/z (ES)=545 (MH)+
For 1Dq: 1-(4-fluorobenzyl)-5-[(3-pyridin-3-ylpyrrolidin-1-yl)carbonyl]-2-[3-(trifluoromethoxy)phenyl]-1H-benzimidazole: m/z (ES)=561 (MH)+
For 1Dr: 1-(4-fluorobenzyl)-5-[(3-pyridin-3-ylpyrrolidin-1-yl)carbonyl]-2-[4-(trifluoromethoxy)phenyl]-1H-benzimidazole: m/z (ES)=561 (MH)+
For 1Du: 2-(4-chlorobenzyl)-1-(4-fluorobenzyl)-5-[(3-pyridin-3-ylpyrrolidin-1-yl)carbonyl]-1H-benzimidazole: m/z (ES)=525 (MH)+
For 1Dv: 1-(4-fluorobenzyl)-2-pyridin-3-yl-5-[(3-pyridin-3-ylpyrrolidin-1-yl)carbonyl]-1H-benzimidazole: m/z (ES)=478 (ME)+
For 1Dw: 1-(4-fluorobenzyl)-2-pyridin-4-yl-5-[(3-pyridin-3-ylpyrrolidin-1-yl)carbonyl]-1H-benzimidazole: m/z (ES)=478 (MH)+
For 1El: 1-cyclopropyl-2-phenyl-5-[(3-pyridin-3-ylpyrrolidin-1-yl)carbonyl]-1H-benzimidazole: m/z (ES)=409 (MH)+
For 1En: 1-cyclopropyl-2-(2,4-difluorophenyl)-5-[(3-pyridin-3-ylpyrrolidin-1-yl)carbonyl]-1H-benzimidazole: m/z (ES)=445 (MH)+
For 1Eo: 1-cyclopropyl-2-(2,4-dichlorophenyl)-5-[(3-pyridin-3-ylpyrrolidin-1-yl)carbonyl]-1H-benzimidazole: m/z (ES)=477 (MH)+

For 1Eq: 1-cyclopropyl-5-[(3-pyridin-3-ylpyrrolidin-1-yl)carbonyl]-2-[3-(trifluoromethoxy)phenyl]-1H-benzimidazole: m/z (ES)=493 (MH)+
For 1Er: 1-cyclopropyl-5-[(3-pyridin-3-ylpyrrolidin-1-yl)carbonyl]-2-[4-(trifluoromethoxy)phenyl]-1H-benzimidazole: m/z (ES)=493 (MH)+
For 1Es: 2-[3,5-bis(trifluoromethyl)phenyl]-1-cyclopropyl-5-[(3-pyridin-3-ylpyrrolidin-1-yl)carbonyl]-1H-benzimidazole: m/z (ES)=545 (MH)+
For 1Fl: 1-cyclobutyl-2-phenyl-5-[(3-pyridin-3-ylpyrrolidin-1-yl)carbonyl]-1H-benzimidazole: m/z (ES)=423 (MH)+
For 1Fn: 1-cyclobutyl-2-(2,4-difluorophenyl)-5-[(3-pyridin-3-ylpyrrolidin-1-yl)carbonyl]-1H-benzimidazole: m/z (ES)=459 (MH)+
For 1Fo: 1-cyclobutyl-2-(2,4-dichlorophenyl)-5-[(3-pyridin-3-ylpyrrolidin-1-yl)carbonyl]-1H-benzimidazole: m/z (ES)=491 (MH)+
For 1Fq: 1-cyclobutyl-5-[(3-pyridin-3-ylpyrrolidin-1-yl)carbonyl]-2-[3-(trifluoromethoxy)phenyl]-1H-benzimidazole: m/z (ES)=507 (MH)+
For 1Fr: 1-cyclobutyl-5-[(3-pyridin-3-ylpyrrolidin-1-yl)carbonyl]-2-[4-(trifluoromethoxy)phenyl]-1H-benzimidazole: m/z (ES)=507 (MH)+
For 1Fu: 2-(4-chlorobenzyl)-1-cyclobutyl-5-[(3-pyridin-3-ylpyrrolidin-1-yl)carbonyl]-1,1-benzimidazole: m/z (ES)=471 (MH)+
For 1Fv: 1-cyclobutyl-2-pyridin-3-yl-5-[(3-pyridin-3-ylpyrrolidin-1-yl)carbonyl]-1H-benzimidazole: m/z (ES)=424 (MH)+
For 1Fw: 1-cyclobutyl-2-pyridin-4-yl-5-[(3-pyridin-3-ylpyrrolidin-1-yl)carbonyl]-1H-benzimidazole: m/z (ES)=424 (MH)+
For 1Gr: 1-(1-methylcyclopropyl)-5-[(3-pyridin-3-ylpyrrolidin-1-yl)carbonyl]-2-[4-(trifluoromethoxy)phenyl]-1H-benzimidazole: m/z (ES)=507 (MH)+
For 1Hl: 2-phenyl-1-pyridin-3-yl-5-[(3-pyridin-3-ylpyrrolidin-1-yl)carbonyl]-1H-benzimidazole: m/z (ES)=446 (MH)+
For 1Hn: 2-(2,4-difluorophenyl)-1-pyridin-3-yl-5-[(3-pyridin-3-ylpyrrolidin-1-yl)carbonyl]-1H-benzimidazole: m/z (ES)=482 (MH)+
For 1Ho: 2-(2,4-dichlorophenyl)-1-pyridin-3-yl-5-[(3-pyridin-3-ylpyrrolidin-1-yl)carbonyl]-1H-benzimidazole: m/z (ES)=514 (MH)+
For 1Hp: 2-(3,5-dichlorophenyl)-1-pyridin-3-yl-5-[(3-pyridin-3-ylpyrrolidin-1-yl)carbonyl]-1H-benzimidazole: m/z (ES)=514 (MH)+
For 1Hq: 1-pyridin-3-yl-5-[(3-pyridin-3-ylpyrrolidin-1-yl)carbonyl]-2-[3-(trifluoromethoxy)phenyl]-1H-benzimidazole: m/z (ES)=530 (MH)+
For 1 Hr: 1-pyridin-3-yl-5-[(3-pyridin-3-ylpyrrolidin-1-yl)carbonyl]-2-[4-(trifluoromethoxy)phenyl]-1H-benzimidazole: m/z (ES)=530 (MH)+
For 1Hu: 2-(4-chlorobenzyl)-1-pyridin-3-yl-5-[(3-pyridin-3-ylpyrrolidin-1-yl)carbonyl]-1H-benzimidazole: m/z (ES)=494 (MH)+
For 1Hv: 1,2-dipyridin-3-yl-5-[3-pyridin-3-ylpyrrolidin-1-yl)carbonyl]-1H-benzimidazole: m/z (ES)=447 (MH)+
For 1Hw: 1-pyridin-3-yl-2-pyridin-4-yl-5-[3-pyridin-3-ylpyrrolidin-1-yl)carbonyl]-1H-benzimidazole: m/z (ES)=447 (MH)+

TABLE 1B
1I 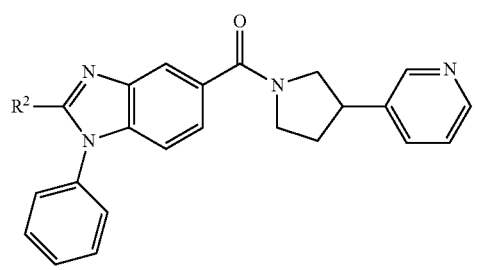
1J 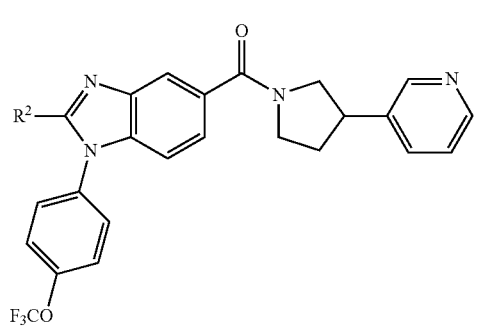
1K 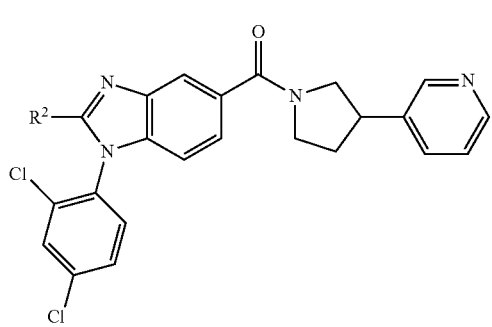
1L 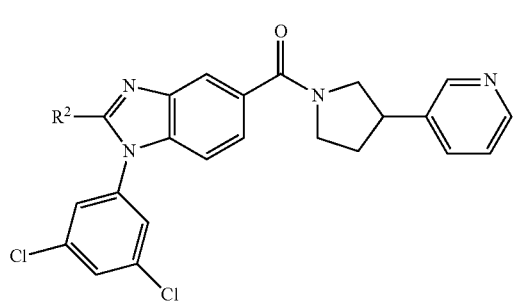
| Ex. 1I | Ex. 1J | Ex. 1K | Ex. 1L | R² |
|---|---|---|---|---|
| a | a | a | a | Me |
| b | b | b | b | CF$_3$ |
| c | c | c | c | $^i$Pr |
| d | d | d | d | $^i$Bu |
| e | e | e | e | $^t$Bu |
| f | f | f | f | $^c$Pr |
| g | g | g | g | $^c$Bu |
| h | h | h | h |  |
TABLE 1B-continued
| | | | | |
|---|---|---|---|---|
| i | i | i | i | 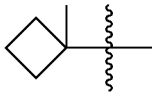 [SMILES: *C1(C)CCC1] |
| j | j | j | j | 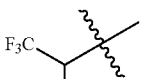 |
| k | k | k | k | 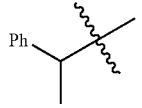 |
| l | l | l | l | Ph |
| m | m | m | m | 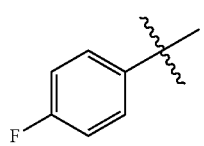 [SMILES: *c1ccc(F)cc1] |
| n | n | n | n | 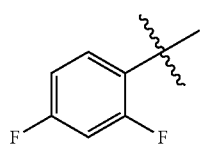 [SMILES: *c1ccc(F)cc1F] |
| o | o | o | o | 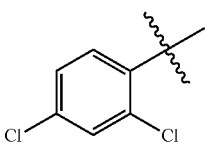 [SMILES: *c1ccc(Cl)cc1Cl] |
| p | p | p | p | 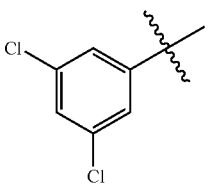 [SMILES: *c1cc(Cl)cc(Cl)c1] |
| q | q | q | q | 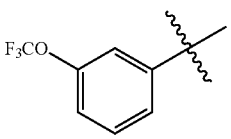 [SMILES: *c1cccc(OC(F)(F)F)c1] |
| r | r | r | r | 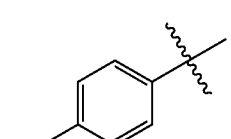 |
| s | s | s | s | 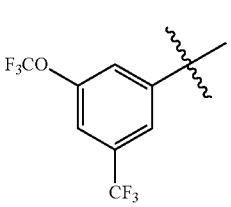 |

TABLE 1B-continued

| | | | | |
|---|---|---|---|---|
| t | t | t | t | 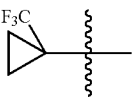 |
| u | u | u | u | 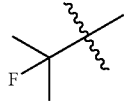 |
| v | v | v | v | 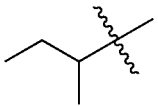 [SMILES: *C(C)CC] |

Table 1B. Parent Ion m/z (MH)+ data for compounds

For 1Ia: 2-methyl-1-phenyl-5-[(3-pyridin-3-ylpyrrolidin-1-yl)carbonyl]-1H-benzimidazole: m/z (ES)=383 (MH)+

For 1Is: 2-[3,5-bis(trifluoromethyl)phenyl]-1-phenyl-5-[(3-pyridin-3-ylpyrrolidin-1-yl)carbonyl]-1H-benzimidazole: m/z (ES)=581 (MH)+

For 1Ja: 2-methyl-5-[(3-pyridin-3-ylpyrrolidin-1-yl)carbonyl]-1-[4-(trifluoromethoxy)phenyl]-1H-benzimidazole: m/z (ES)=467 (MH)+

For 1Jb: 5-[(3-pyridin-3-ylpyrrolidin-1-yl)carbonyl]-1-[4-(trifluoromethoxy)phenyl]-2-(trifluoromethyl)-1H-benzimidazole: m/z (ES)=521 (MH)+

For 1Jc: 2-isopropyl-5-[(3-pyridin-3-ylpyrrolidin-1-yl)carbonyl]-1-[4-(trifluoromethoxy)phenyl]-1H-benzimidazole: m/z (ES)=495 (MH)+

For 1Jd: 2-isobutyl-5-[(3-pyridin-3-ylpyrrolidin-1-yl)carbonyl]-1-[4-(trifluoromethoxy)phenyl]-1H-benzimidazole: m/z (ES)=509 (MH)+

For 1Je: 2-tert-butyl-5-[(3-pyridin-3-ylpyrrolidin-1-yl)carbonyl]-1-[4-(trifluoromethoxy)phenyl]-1H-benzimidazole: m/z (ES)=509 (MH)+

For 1Jf: 2-cyclopropyl-5-[(3-pyridin-3-ylpyrrolidin-1-yl)carbonyl]-1-[4-(trifluoromethoxy)phenyl]-1H-benzimidazole: m/z (ES)=493 (MH)+

For 1Jg: 2-cyclobutyl-5-[(3-pyridin-3-ylpyrrolidin-1-yl)carbonyl]-1-[4-(trifluoromethoxy)phenyl]-1H-benzimidazole: m/z (ES)=507 (MH)+

For 1Jh: 2-(1-methylcyclopropyl)-5-[(3-pyridin-3-ylpyrrolidin-1-yl)carbonyl]-1-[4-(trifluoromethoxy)phenyl]-1H-benzimidazole: m/z (ES)=507 (MH)+

(Compound 1Jh is a single enantiomer, for which the absolute stereochemistry was not determined. 1Jh was isolated as the slower eluting enantiomer following chiral HPLC purification.)

For 1Ji: 2-(1-methylcyclobutyl)-5-[(3-pyridin-3-ylpyrrolidin-1-yl)carbonyl]-1-[4-(trifluoromethoxy)phenyl]-1H-benzimidazole: m/z (ES)=521 (ME)+

(Compound 1Ji was prepared as a single enantiomer, for which the absolute stereochemistry was not determined, substituting i-20e for i-4-d.)

For 1Jj: 5-[(3-pyridin-3-ylpyrrolidin-1-yl)carbonyl]-1-[4-(trifluoromethoxy)phenyl]-2-(2,2,2-trifluoro-1-methylethyl)-1H-benzimidazole: m/z (ES)=549 (MH)+

For 1Jk: 2-(1-phenylethyl)-5-[(3-pyridin-3-ylpyrrolidin-1-yl)carbonyl]-1-[4-(trifluoromethoxy)phenyl]-1H-benzimidazole: m/z (ES)=557 (MH)+

For 1Jl: 2-phenyl-5-[(3-pyridin-3-ylpyrrolidin-1-yl)carbonyl]-1-[4-(trifluoromethoxy)phenyl]-1H-benzimidazole: m/z (ES)=529 (MH)+

For 1Jt: 5-[(3-pyridin-3-ylpyrrolidin-1-yl)carbonyl]-1-[4-(trifluoromethoxy)phenyl]-2-[1-(trifluoromethyl)cyclopropyl]-1H-benzimidazole: m/z (ES)=561 (MH)+

For 1Ju: 2-(1-fluoro-1-methylethyl)-5-[(3-pyridin-3-ylpyrrolidin-1-yl)carbonyl]-1-[4-(trifluoromethoxy)phenyl]-1H-benzimidazole: m/z (ES)=513 (MH)+

For 1Jv: 2-sec-butyl-5-[(3-pyridin-3-ylpyrrolidin-1-yl)carbonyl]-1-[4-(trifluoromethoxy)phenyl]-1H-benzimidazole: m/z (ES)=509 (MH)+

For 1Kc: 1-(2,4-dichlorophenyl)-2-isopropyl-5-[(3-pyridin-3-ylpyrrolidin-1-yl)carbonyl]-1H-benzimidazole: m/z (ES)=479 (MH)+

(Compound 1Kc was prepared as a single enantiomer, for which the absolute stereochemistry was not determined, substituting i-20e for i-4-d.)

For 1Lc: 1-(3,5-dichlorophenyl)-2-isopropyl-5-[(3-pyridin-3-ylpyrrolidin-1-yl)carbonyl]-1H-benzimidazole: m/z (ES)=479 (MH)+

TABLE 1C

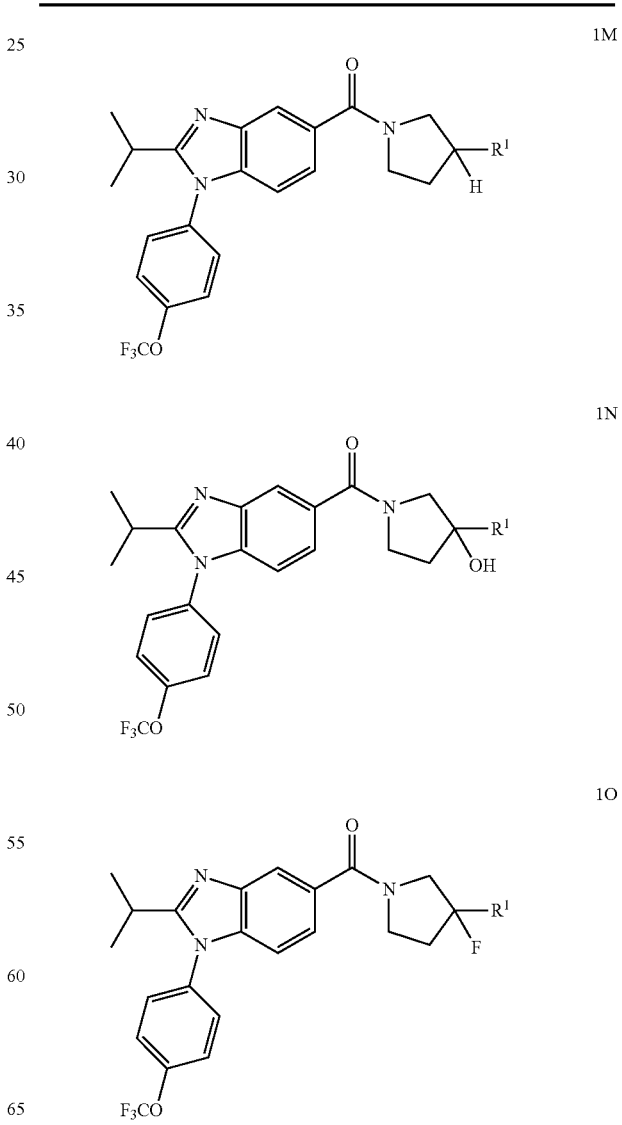

TABLE 1C-continued

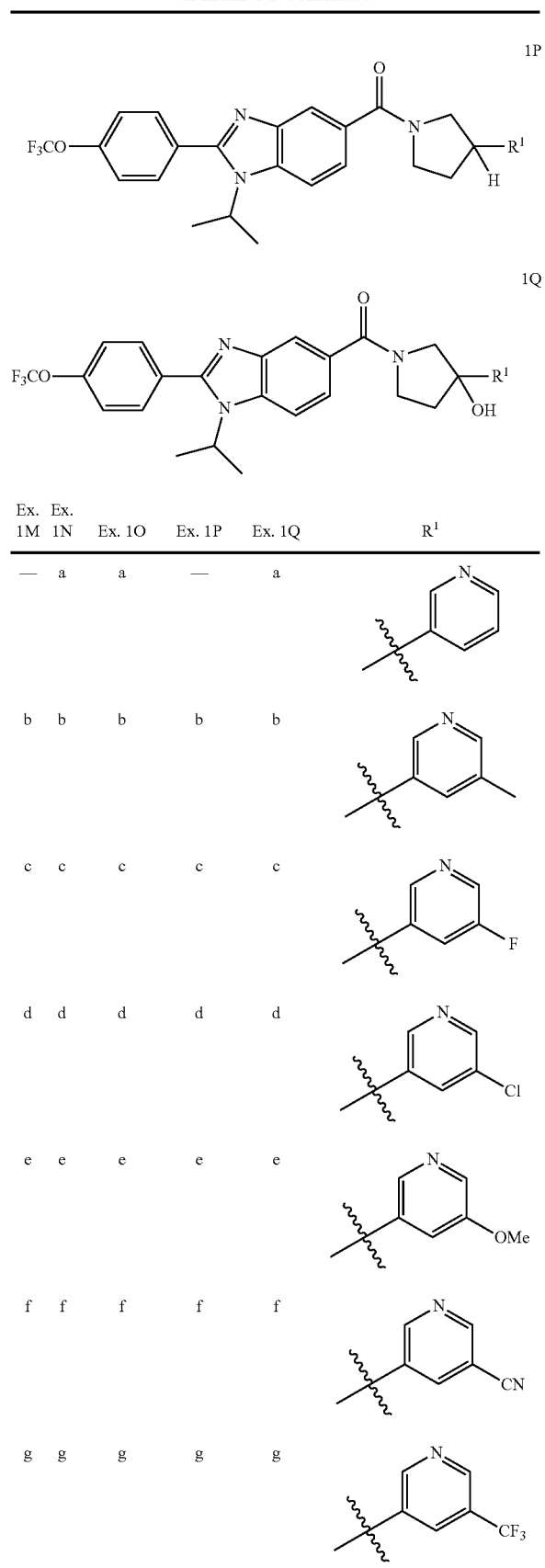

| Ex. 1M | Ex. 1N | Ex. 1O | Ex. 1P | Ex. 1Q | R¹ |
|---|---|---|---|---|---|
| — | a | a | — | a | pyridin-3-yl |
| b | b | b | b | b | 5-methylpyridin-3-yl |
| c | c | c | c | c | 5-fluoropyridin-3-yl |
| d | d | d | d | d | 5-chloropyridin-3-yl |
| e | e | e | e | e | 5-methoxypyridin-3-yl |
| f | f | f | f | f | 5-cyanopyridin-3-yl |
| g | g | g | g | g | 5-trifluoromethylpyridin-3-yl |
| h | h | h | h | h | 6-methoxypyridin-3-yl |
| i | i | i | i | i | pyrimidin-5-yl |
| j | j | j | j | j | 5-methyl-1,3,4-oxadiazol-2-yl |
| k | k | k | k | k | 4H-1,2,4-triazol-4-ylmethyl |

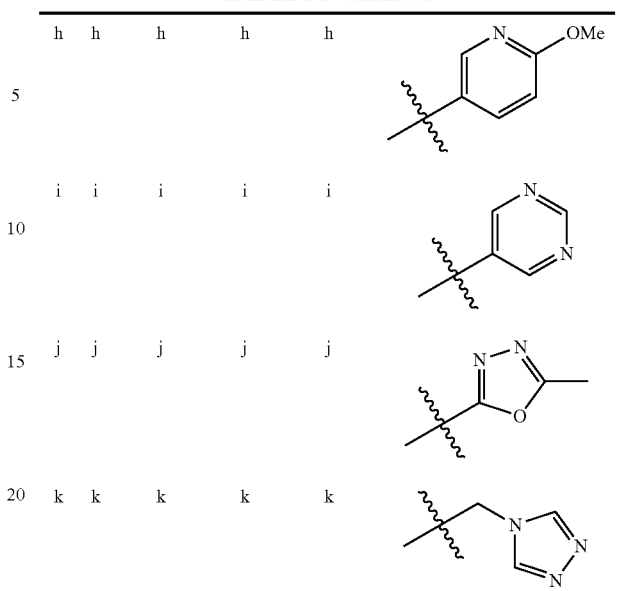

Table 1C. Parent Ion m/z (MH)⁺ data for compounds:

For 1Mb: 2-isopropyl-5-{[3-(5-methylpyridin-3-yl)pyrrolidin-1-yl]carbonyl}-1-[4-(trifluoromethoxy)phenyl]-1H-benzimidazole: m/z (ES)=509 (MH)⁺

For 1Mc: 2-isopropyl-5-{[3-(5-fluoropyridin-3-yl)pyrrolidin-1-yl]carbonyl}-1-[4-(trifluoromethoxy)phenyl]-1H-benzimidazole: m/z (ES)=513 (MH)⁺

For 1Me: 2-isopropyl-5-{[3-(5-methoxypyridin-3-yl)pyrrolidin-1-yl]carbonyl}-1-[4-(trifluoromethoxy)phenyl]-1H-benzimidazole: m/z (ES)=525 (MH)⁺

For 1Mj: 2-isopropyl-5-{[3-(5-methyl-1,3,4-oxadiazol-2-yl)pyrrolidin-1-yl]carbonyl}-1-[4-(trifluoromethoxy)phenyl]-1H-benzimidazole: m/z (ES)=500 (MH)⁺

For 1Mk: 2-isopropyl-5-{[3-(4H-1,2,4-triazol-4-ylmethyl)pyrrolidin-1-yl]carbonyl}-1-[4-(trifluoromethoxy)phenyl]-1H-benzimidazole: m/z (ES)=499 (MH)⁺

For 1Na: 1-({2-isopropyl-1-[4-(trifluoromethoxy)phenyl]-1H-benzimidazol-5-yl}carbonyl)-3-pyridin-3-ylpyrrolidin-3-ol: m/z (ES)=511 (MH)⁺

For 1Nb: 1-({2-isopropyl-1-[4-(trifluoromethoxy)phenyl]-1H-benzimidazol-5-yl}carbonyl)-3-(5-methylpyridin-3-yl)pyrrolidin-3-ol: m/z (ES)=525 (MH)⁺

For 1Nc: 3-(5-fluoropyridin-3-yl)-1-({2-isopropyl-1-[4-trifluoromethoxy)phenyl]-1H-benzimidazol-5-yl}carbonyl)pyrrolidin-3-ol: m/z (ES)=529 (MH)⁺

For 1Nd: 3-(5-chloropyridin-3-yl)-1-({2-isopropyl-1-[4-(trifluoromethoxy)phenyl]-1H-benzimidazol-5-yl}carbonyl)pyrrolidin-3-ol: m/z (ES)=545 (MH)⁺

For 1Ne: 1-({2-isopropyl-1-[4-(trifluoromethoxy)phenyl]-1H-benzimidazol-5-yl}carbonyl)-3-(5-methoxypyridin-3-yl)pyrrolidin-3-ol: m/z (ES)=541 (MH)⁺

For 1Nf: 5-[3-hydroxy-1-({2-isopropyl-1-[4-trifluoromethoxy)phenyl]-1H-benzimidazol-5-yl}carbonyl)pyrrolidin-3-yl]nicotinonitrile: m/z (ES)=536 (MH)⁺

For 1Ng: 1-({2-isopropyl-1-[4-trifluoromethoxy)phenyl]-1H-benzimidazol-5-yl}carbonyl)-3-[5-(trifluoromethyl)pyridin-3-yl]pyrrolidin-3-ol: m/z (ES)=579 (MH)⁺

For 1Nh: 1-({2-isopropyl-1-[4-trifluoromethoxy)phenyl]-1H-benzimidazol-5-yl}carbonyl)-3-(2-methoxypyridin-5-yl)pyrrolidin-3-ol: m/z (ES)=541 (MH)⁺

For 1Oa: 5-[(3-fluoro-3-pyridin-3-ylpyrrolidin-1-yl)carbonyl]-2-isopropyl-1-[4-(trifluoromethoxy)phenyl]-1H-benzimidazole: m/z (ES)=513 (MH)⁺

For 1Pi: 1-isopropyl-5-[(3-pyrimidin-5-ylpyrrolidin-1-yl)carbonyl]-2-[4-(trifluoromethoxy)phenyl]-1H-benzimidazole: m/z (ES)=496 (MH)+

For 1Pj: 1-isopropyl-5-{[3-(5-methyl-1,3,4-oxadiazol-2-yl)pyrrolidin-1-yl]carbonyl}-2-[4-(trifluoromethoxy)phenyl]-1H-benzimidazole: m/z (ES)=500 (MH)+

For 1Qa: 1-({1-isopropyl-2-[4-(trifluoromethoxy)phenyl]-1H-benzimidazol-5-yl}carbonyl)-3-pyridin-3-ylpyrrolidin-3-ol: m/z (ES)=511 (MH)+

TABLE 1D

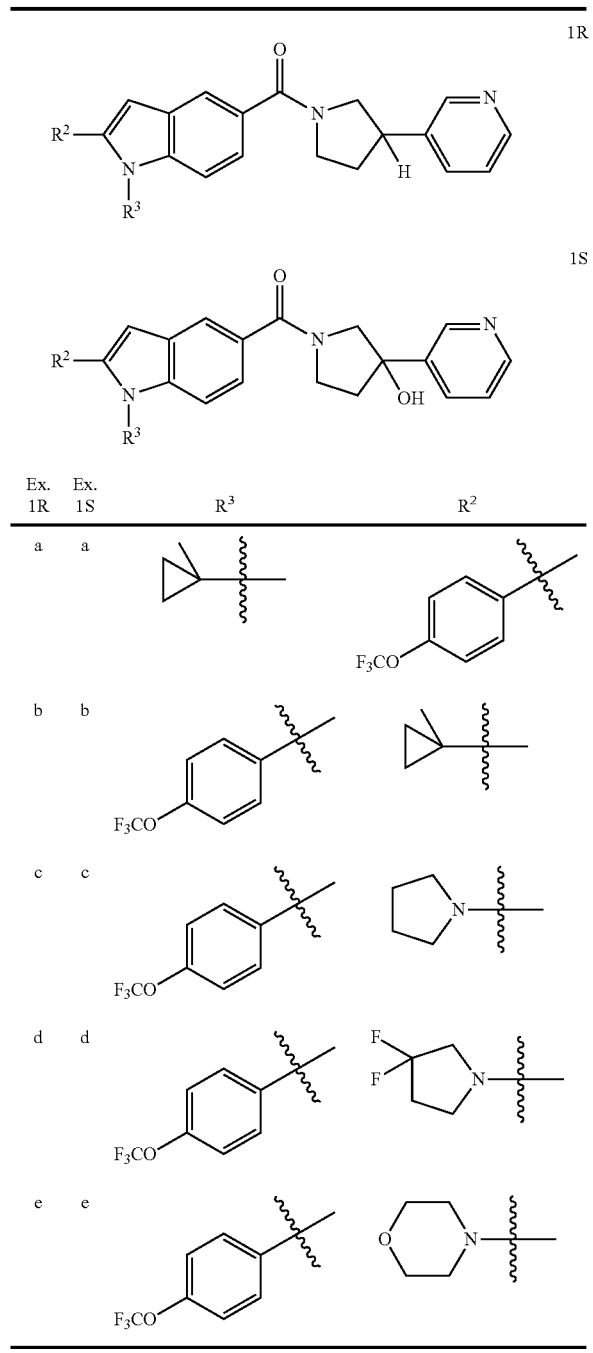

Table 1D. Parent Ion m/z (MH)+ data for compounds

For 1Rc: 5-[(3-pyridin-3-ylpyrrolidin-1-yl)carbonyl]-2-pyrrolidin-1-yl-1-[4-(trifluoromethoxy)phenyl]-1H-benzimidazole: m/z (ES)=522 (MH)+

For 1Rd: 2-(3,3-difluoropyrrolidin-1-yl)-5-[(3-pyridin-3-ylpyrrolidin-1-yl)carbonyl]-1-[4-(trifluoromethoxy)phenyl]-1H-benzimidazole: m/z (ES) 558 (MH)+

For 1Re: 2-morpholin-4-yl-5-[(3-pyridin-3-ylpyrrolidin-1-yl)carbonyl]-1-[4-(trifluoromethoxy)phenyl]-1H-benzimidazole: m/z (ES) 538 (MH)+

For 1Sa: 1-({1-(1-methylcyclopropyl)-2-[4-(trifluoromethoxy)phenyl]-1H-benzimidazol-5-yl}carbonyl)-3-pyridin-3-ylpyrrolidin-3-ol: m/z (ES)=523 (MH)+

(Compound 1Sa is a single enantiomer, for which the absolute stereochemistry was not determined. 1Sa was isolated as the slower eluting enantiomer following chiral HPLC purification.)

For 1Sb: 2-({1-(1-methylcyclopropyl)-1-[4-(trifluoromethoxy)phenyl]-1H-benzimidazol-5-yl}carbonyl)-3-pyridin-3-ylpyrrolidin-3-ol: m/z (ES)=523 (MH)+

For 1Sd: 1-({2-(3,3-difluoropyrrolidin-1-yl)-1-[4-(trifluoromethoxy)phenyl]-1H-benzimidazol-5-yl}carbonyl)-3-pyridin-3-ylpyrrolidin-3-ol: m/z (ES)=574 (MH)+

Example 2

Preparation of 3-isopropyl-6-[(3-pyridin-3-ylpyrrolidin-1-yl)carbonyl]-2-[4-(trifluoromethoxy)phenyl]-3H-imidazo[4,5-b]pyridine (2a)

i-2f $\xrightarrow{\text{step A}}$

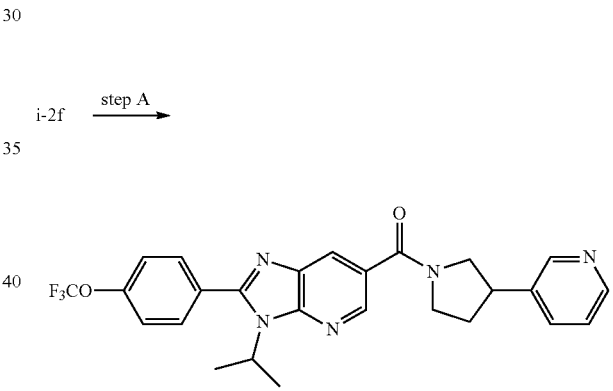

Compound 2a was prepared following procedures similar to those described for the preparation of 1a, substituting i-2f, for i-1e. m/z (ES) 496 (MH)+.

Example 3

Following procedures similar to those described for the preparation of 1a, compounds of Formula I wherein y is —CH$_2$— and m=1 or 2 are prepared by coupling intermediates i-13e, i-14b, or i-15d to i-15l to intermediates of formula

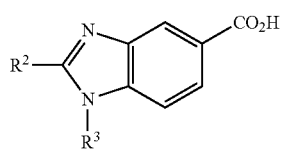

such as i-1e, i-1h, i-2f, i-3f and intermediates in Tables i-1A1, i-1A2, i-2, i-3.

Example 4

PAF Binding Assay

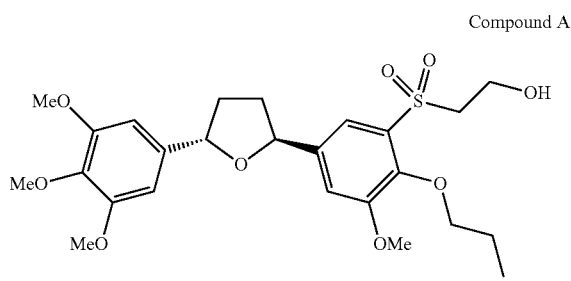 [SMILES: CCCOc1c(OC)cc([C@@H]2CC[C@@H](c3cc(OC)c(OC)c(OC)c3)O2)cc1S(=O)(=O)CCO]

Compound A

PAFR was derived from membranes from CHO cells overexpressing the full-length human PAFR. Supernatant from the cell homogenate pellet (3000×g) is pelleted (35000×g), and the resulting pellet is resuspended in a Tris HCl buffer (50 mM Tris HCl pH 7.4, 5 mM MgCl$_2$, 30% glycerol) to afford a parent PAFR stock that is diluted in PAF binding buffer (50 mM HEPES pH 7.0, 10 mM MgCl$_2$, 5 mM CaCl$_2$, 5 mM D-(+)glucose, 0.25% fatty-acid free BSA) to afford a PAFR assay stock (120 µg/mL) prior to each use.

Binding buffer (48 µL) and competitor compound (i.e., the compound to be tested) in DMSO (2 µL) were added to a 96-well plate. Cold PAF C-18 (200 nM final concentration) was used to determine non-specific binding. 25000 cpm of $^3$H-PAF (25 µL of a stock solution in PAF binding buffer) was added to all wells, and the plates sealed and shaken at rt for 5 min. PAFR assay stock (3 µg/well) was added, and the plate was sealed and shaken at rt for 2 h. SPA beads[1] (10 µL of a 25 mg/mL suspension in binding buffer) were added to all wells, and the plates were sealed and shaken for 30 min. The plates were centrifuged (1900 rpm for 5 min.), allowed to stand for 30 min. and read on a Microbeta TriLux counter.

Specific binding is defined as total binding minus non-specific binding. Total binding was the amount of $^3$H-PAF bound to SPA beads in the absence of competitor; non-specific binding was $^3$H-PAF bound in the presence of 30 µM Compound A.[2] The IC$_{50}$ values were obtained by computer analysis of the experimental data.[3] Percent inhibition was calculated as 100−[(Sample-Non-specific bound)/(Total bound Non-specific bound)×100]

Representative tested compounds of the invention were determined to have an IC$_{50}$<500 nM, and most of the tested compounds had an IC$_{50}$<100 nM. Preferred compounds had an IC$_{50}$<40 nM. IC$_{50}$ results follow for Examples 1c, 1Ar, 1Fr, 1Gr and 1Qa:

| Example | Binding IC$_{50}$ |
|---------|-------------------|
| 1c      | 11 nM             |
| 1Ar     | 2 nM              |
| 1Fr     | 9 nM              |
| 1Gr     | 10 nM             |
| 1Qa     | 9 nM              |

REFERENCES

1. Wheat Germ Agglutinin (WGA) PVT SPA Scintillation Beads; GE Healthcare.
2. Hwang, S. B., et al. *J. Lipid Mediat.* 1993, 7, 115434.
3. Kinetic, EBDA, Ligand, Lowry. A collection of Radioligand Binding Analysis Programs by G. A. MacPherson. Elsevier-BIOSOFT.

While the invention has been described with reference to certain particular embodiments thereof, numerous alternative embodiments will be apparent to those skilled in the art from the teachings described herein. Recitation of a specific compound in the claims (i.e., a species) without a chiral designation is intended to encompass the racemate, enantiomeric mixtures, each individual enantiomer, a diastereoisomeric mixture and each individual diastereoisomer of the compound where such forms are possible due to the presence of one or more asymmetric centers. All patents, patent applications and publications cited herein are incorporated by reference in their entirety.

What is claimed is:
1. A compound having structural Formula I:

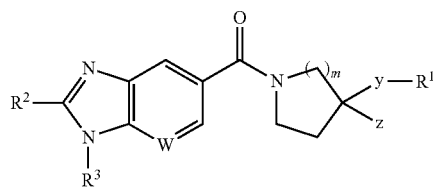

and the pharmaceutically acceptable salts thereof wherein:
R$^1$ is selected from the group consisting of
  (a) a 5-membered heterocyclic ring containing 1 to 4 heteroatoms selected from 1 to 4 of N, 0 (zero) to 1 of O, and 0 (zero) to 1 of S, wherein the ring is optionally substituted with R$^4$, and
  (b) a 6-membered heterocyclic ring containing 1 to 2 of N, wherein the ring is optionally substituted with R$^4$;
R$^2$ is selected from the group consisting of
  (a) —C$_{1-6}$alkyl optionally substituted with one or more substituents selected from the group consisting of:
    (i) fluoro,
    (ii) hydroxy,
    (iii) Hetcy optionally substituted with one or more substituents selected from the group consisting of —F, —OH and methyl, and
    (iv) phenyl optionally substituted with one or more substituents selected from the group consisting of —F, —Cl, —OH, —CN, —OC$_{1-4}$alkyl optionally substituted with one or more substituents selected from the group consisting of fluoro and cyano, and —C$_{1-4}$alkyl optionally substituted with one or more substituents selected from the group consisting of fluoro, cyano and —OC(O)C$_{1-4}$alkyl,
  (b) —C$_{3-6}$cycloalkyl optionally substituted with one or more substituents selected from the group consisting of:
    (i) fluoro,
    (ii) hydroxy, and
    (iii) —C$_{1-4}$alkyl optionally substituted with one or more of fluoro, (c) —N(C$_{1-3}$alkyl)$_2$ optionally substituted with one or more substituents selected from the group consisting of fluoro and hydroxy,
(d) phenyl optionally mono- or di-substituted with R$^5$,
(e) Hetcy optionally substituted with one or more substituents selected from the group consisting of fluoro, hydroxy and methyl
(f) a 5-membered heterocyclic ring containing 1 to 4 heteroatoms selected from 1 to 4 of N, 0 (zero) to 1 of O, and 0 (zero) to 1 of S, wherein the ring is optionally mono- or di-substituted with R$^5$, and
(g) a 6-membered heterocyclic ring containing 1 to 2 of N, wherein the ring is optionally mono- or di-substituted with R$^5$;

R$^3$ is selected from the group consisting of
(a) —C$_{1-6}$alkyl optionally substituted with one or more substituents selected from the group consisting of:
(i) fluoro,
(ii) hydroxy, and
(iii) phenyl optionally substituted with one or more substituents selected from the group consisting of —F, —Cl, —CN, —OH, —OMe, —OC(O)C$_{1-4}$alkyl, —CF$_3$ and —OCF$_3$,
(b) —C$_{3-6}$cycloalkyl optionally substituted with one or more substituents selected from the group consisting of:
(i) fluoro,
(ii) hydroxy,
(iii) —C$_{1-4}$alkyl optionally substituted with one or more of fluoro, and
(iv) —OC$_{1-4}$alkyl optionally substituted with one or more of fluoro,
(c) phenyl optionally mono- or di-substituted with R$^5$, and
(d) a 6-membered heterocyclic ring containing 1 to 2 of N, wherein the ring is optionally mono- or di-substituted with R$^5$;

R$^4$ is selected independently at each occurrence from the group consisting of (a) —F, (b) —Cl, (c) hydroxy, (d) cyano, (e) oxo, (f) amino, (g) —C$_{1-6}$alkyl optionally substituted with one or more of fluoro, (h) —C$_{3-6}$cycloalkyl optionally substituted with one or more of fluoro, and (i) —OC$_{1-6}$alkyl optionally substituted with one or more of fluoro;

R$^5$ is selected independently at each occurrence from the group consisting of (a) —F, (b) —Cl, (c) —OH, (d) —OC(O)C$_{1-4}$alkyl, (e) —NR$^a$R$^b$, (f) —CN, (g) —C$_{1-4}$alkyl optionally substituted with one or more of fluoro and (h) —OC$_{1-4}$alkyl optionally substituted with one or more of fluoro;

R$^a$ and R$^b$ are independently selected from the group consisting of (a) hydrogen, (b) —C$_{1-4}$alkyl optionally substituted with one or more substituents selected from the group consisting of (i) fluoro, (ii) hydroxy and (iii) phenyl optionally substituted with one or more substituents selected from the group consisting of —F, —Cl, —OCH$_3$, —CF$_3$ and —OCF$_3$, and (c) —C$_{3-6}$cycloalkyl optionally substituted with one or more substituents selected from the group consisting of fluoro, hydroxy and —C$_{1-4}$alkyl;
or R$^a$ and R$^b$ together with the nitrogen to which they are both attached represent azetidinyl, pyrrolidinyl, piperidinyl, piperazinyl or morpholinyl, each optionally substituted with one or more substituents selected from —OH and —F;
m is the integer 1;
W is selected from N and CH;
y is selected from a bond and —CR$^{6a}$R$^{6b}$—;
z is selected from the group consisting of hydrogen, fluoro, hydroxy, and —C$_{1-4}$alkyl optionally substituted with one or more of —OH and —F;
R$^{6a}$ and R$^{6b}$ are independently selected from the group consisting of (a) —H, (b) hydroxy, (c) —C$_{1-4}$alkyl optionally substituted with one or more of fluoro, (d) —OC$_{1-4}$alkyl optionally substituted with one or more of fluoro and (e) —OC(O)C$_{1-4}$alkyl;
or R$^{6a}$ and R$^{6b}$ are joined together with the carbon to which they are both attached to form a —C$_{3-6}$cycloalk-diyl ring; and
Hetcy is selected from the group consisting of azetidinyl, pyrrolidinyl, piperidinyl, piperazinyl and morpholinyl.

2. The compound of claim 1 wherein y is a bond.

3. The compound of claim 1 having a structural Formula selected from the group consisting of:

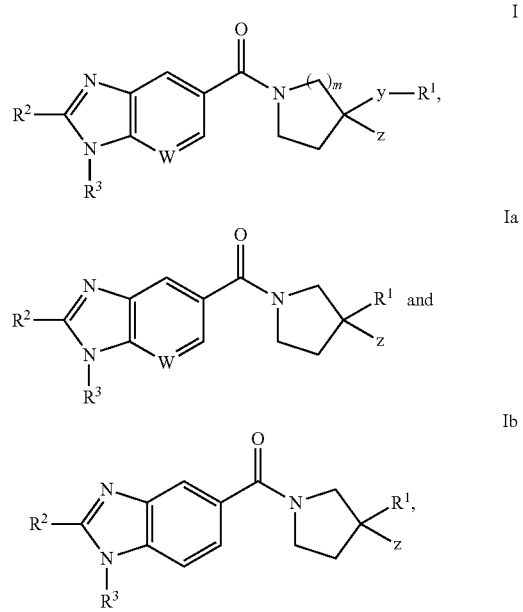

and the pharmaceutically acceptable salts thereof.

4. The compound of claim 3 wherein R$^1$ is selected from the group consisting of pyridyl, pyrimidinyl, oxadiazolyl, tetrazolyl, triazolyl, pyrazolyl, thiazolyl, and isoxazolyl, each of which is optionally substituted with R$^4$.

5. The compound of claim 4 wherein R$^1$ is selected from the group consisting of pyridyl optionally substituted with R$^4$, and oxadiazolyl optionally substituted with R$^4$.

6. The compound of claim 4 having a structural Formula selected from the group consisting of:

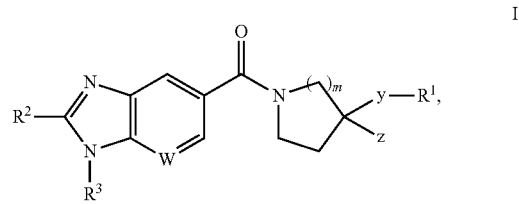

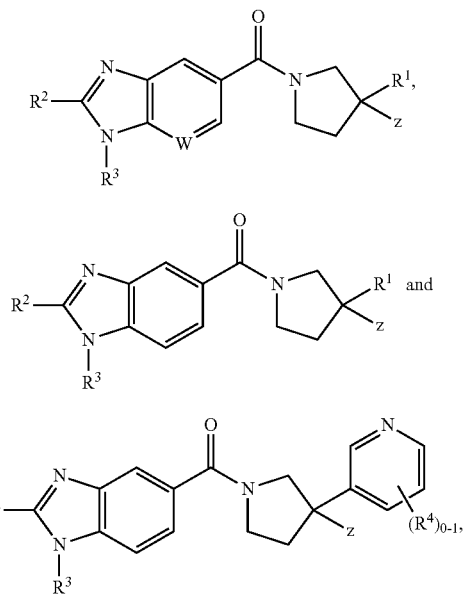

and pharmaceutically acceptable salts thereof, wherein $R^4$ is absent or is independently selected at each occurrence from the group consisting of fluoro, chloro, hydroxy, oxo, methyl, —$CF_3$, methoxy, ethoxy and cyano.

7. The compound of claim 6 wherein $R^3$ is selected from the group consisting of —$C_{1-4}$alkyl optionally substituted with phenyl, wherein the phenyl is optionally substituted with 1 to 2 substituents selected from the group consisting of —F, —Cl and —$OCF_3$; —$C_{3-6}$cycloalkyl optionally substituted with methyl; pyridinyl optionally mono- or di-substituted with $R^5$; and phenyl optionally mono- or di-substituted with $R^5$.

8. The compound of claim 7 wherein $R^2$ is selected from the group consisting of optionally substituted —$C_{1-4}$alkyl; optionally substituted —$C_{3-6}$cycloalkyl; optionally substituted Hetcy; and phenyl optionally mono- or di-substituted with $R^5$.

9. The compound of claim 8 wherein Hetcy is selected from optionally substituted pyrrolidinyl, optionally substituted piperidinyl and optionally substituted morpholinyl.

10. The compound of claim 9 wherein $R^5$ is absent or is independently selected at each occurrence from —F, —Cl, -Me, —OMe, —OEt, —$CF_3$ and —$OCF_3$.

11. The compound of claim 10 wherein $R^3$ is selected from isopropyl; t-butyl; cyclobutyl; cyclopropyl optionally substituted with methyl; and phenyl optionally mono- or di-substituted with $R^5$.

12. The compound of claim 11 wherein $R^2$ is selected from the group consisting of isopropyl; branched butyl; cyclopropyl optionally substituted with methyl; cyclobutyl optionally substituted with methyl; morpholinyl; pyrrolidinyl optionally mono- or di-substituted with fluoro; piperidinyl optionally substituted with hydroxy or fluoro; and phenyl optionally mono- or di-substituted with $R^5$.

13. The compound of claim 6 wherein:
a) $R^2$ is selected from the group consisting of phenyl, 5-membered heterocycle and 6-membered heterocycle, and $R^3$ is selected from the group consisting of —$C_{1-6}$alkyl and —$C_{3-6}$cycloalkyl, wherein $R^2$ and $R^3$ are each optionally substituted; or b) $R^2$ is selected from the group consisting of —$C_{1-6}$alkyl, —$C_{3-6}$cycloalkyl, —$N(C_{1-3}$alkyl$)_2$ and Hetcy, and $R^3$ is selected from the group consisting of phenyl and 6-membered heterocycle, wherein $R^2$ and $R^3$ are each optionally substituted.

14. The compound of claim 6 wherein z selected from the group consisting of —H and hydroxy.

15. The compound of claim 1 selected from the group consisting of:
2-isopropyl-5-[(3-pyridin-3-ylpyrrolidin-1-yl)carbonyl]-1-[4-(trifluoromethoxy)phenyl]-1H-benzimidazole;
1,2-diisopropyl-5-[(3-pyridin-3-ylpyrrolidin-1-yl)carbonyl]-1H-benzimidazole;
1-isopropyl-2-(1-phenylethyl)-5-[(3-pyridin-3-ylpyrrolidin-1-yl)carbonyl]-1H-benzimidazole;
1-isopropyl-2-phenyl-5-[(3-pyridin-3-ylpyrrolidin-1-yl)carbonyl]-1H-benzimidazole;
2-(4-fluorophenyl)-1-isopropyl-5-[(3-pyridin-3-ylpyrrolidin-1-yl)carbonyl]-1H-benzimidazole;
1-isopropyl-5-[(3-pyridin-3-ylpyrrolidin-1-yl)carbonyl]-2-[4-(trifluoromethoxy)phenyl]-1H-benzimidazole;
2-[3,5-bis(trifluoromethyl)phenyl]-1-isopropyl-5-[(3-pyridin-3-ylpyrrolidin-1-yl)carbonyl]-1H-benzimidazole;
2-phenyl-5-[(3-pyridin-3-ylpyrrolidin-1-yl)carbonyl]-1-(2,2,2-trifluoroethyl)-1H-benzimidazole;
2-(2,4-difluorophenyl)-5-[(3-pyridin-3-ylpyrrolidin-1-yl)carbonyl]-1-(2,2,2-trifluoroethyl)-1H-benzimidazole;
2-(2,4-dichlorophenyl)-5-[(3-pyridin-3-ylpyrrolidin-1-yl)carbonyl]-1-(2,2,2-trifluoroethyl)-1H-benzimidazole;
2-(3,5-dichlorophenyl)-5-[(3-pyridin-3-ylpyrrolidin-1-yl)carbonyl]-1-(2,2,2-trifluoroethyl)-1H-benzimidazole;
5-[(3-pyridin-3-ylpyrrolidin-1-yl)carbonyl]-1-(2,2,2-trifluoroethyl)-2-[3-(trifluoromethoxy)phenyl]-1H-benzimidazole;
5-[(3-pyridin-3-ylpyrrolidin-1-yl)carbonyl]-1-(2,2,2-trifluoroethyl)-2-[4-(trifluoromethoxy)phenyl]-1H-benzimidazole;
2-(4-chlorobenzyl)-5-[(3-pyridin-3-ylpyrrolidin-1-yl)carbonyl]-1-(2,2,2-trifluoroethyl)-1H-benzimidazole;
2-pyridin-3-yl-5-[(3-pyridin-3-ylpyrrolidin-1-yl)carbonyl]-1-(2,2,2-trifluoroethyl)-1H-benzimidazole;
2-pyridin-4-yl-5-[(3-pyrimidin-5-ylpyrrolidin-1-yl)carbonyl]-1-(2,2,2-trifluoroethyl)-1H-benzimidazole;
1-tert-butyl-5-[(3-pyridin-3-ylpyrrolidin-1-yl)carbonyl]-2-[4-(trifluoromethoxy)phenyl]-1H-benzimidazole;
1-(4-fluorobenzyl)-2-phenyl-5-[(3-pyridin-3-ylpyrrolidin-1-yl)carbonyl]-1H-benzimidazole;
2-(2,4-difluorophenyl)-1-(4-fluorobenzyl)-5-[(3-pyridin-3-ylpyrrolidin-1-yl)carbonyl]-1H-benzimidazole;
2-(2,4-dichlorophenyl)-1-(4-fluorobenzyl)-5-[(3-pyridin-3-ylpyrrolidin-1-yl)carbonyl]-1H-benzimidazole;
2-(3,5-dichlorophenyl)-1-(4-fluorobenzyl)-5-[(3-pyridin-3-ylpyrrolidin-1-yl)carbonyl]-1H-benzimidazole;
1-(4-fluorobenzyl)-5-[(3-pyridin-3-ylpyrrolidin-1-yl)carbonyl]-2-[3-(trifluoromethoxy)phenyl]-1H-benzimidazole;
1-(4-fluorobenzyl)-5-[(3-pyridin-3-ylpyrrolidin-1-yl)carbonyl]-2-[4-(trifluoromethoxy)phenyl]-1H-benzimidazole;
2-(4-chlorobenzyl)-1-(4-fluorobenzyl)-5-[(3-pyridin-3-ylpyrrolidin-1-yl)carbonyl]-1H-benzimidazole;
1-(4-fluorobenzyl)-2-pyridin-3-yl-5-[(3-pyridin-3-ylpyrrolidin-1-yl)carbonyl]-1H-benzimidazole;
1-(4-fluorobenzyl)-2-pyridin-4-yl-5-[(3-pyridin-3-ylpyrrolidin-1-yl)carbonyl]-1H-benzimidazole;
1-cyclopropyl-2-phenyl-5-[(3-pyridin-3-ylpyrrolidin-1-yl)carbonyl]-1H-benzimidazole;

1-cyclopropyl-2-(2,4-difluorophenyl)-5-[(3-pyridin-3-ylpyrrolidin-1-yl)carbonyl]-1H-benzimidazole;
1-cyclopropyl-2-(2,4-dichlorophenyl)-5-[(3-pyridin-3-ylpyrrolidin-1-yl)carbonyl]-1H-benzimidazole;
1-cyclopropyl-5-[(3-pyridin-3-ylpyrrolidin-1-yl)carbonyl]-2-[3-(trifluoromethoxy)phenyl]-1H-benzimidazole;
1-cyclopropyl-5-[(3-pyridin-3-ylpyrrolidin-1-yl)carbonyl]-2-[4-(trifluoromethoxy)phenyl]-1H-benzimidazole;
2-[3,5-bis(trifluoromethyl)phenyl]-1-cyclopropyl-5-[(3-pyridin-3-ylpyrrolidin-1-yl)carbonyl]-1H-benzimidazole;
1-cyclobutyl-2-phenyl-5-[(3-pyridin-3-ylpyrrolidin-1-yl)carbonyl]-1H-benzimidazole;
1-cyclobutyl-2-(2,4-difluorophenyl)-5-[(3-pyridin-3-ylpyrrolidin-1-yl)carbonyl]-1H-benzimidazole;
1-cyclobutyl-2-(2,4-dichlorophenyl)-5-[(3-pyridin-3-ylpyrrolidin-1-yl)carbonyl]-1H-benzimidazole;
1-cyclobutyl-5-[(3-pyridin-3-ylpyrrolidin-1-yl)carbonyl]-2-[3-(trifluoromethoxy)phenyl]-1H-benzimidazole;
1-cyclobutyl-5-[(3-pyridin-3-ylpyrrolidin-1-yl)carbonyl]-2-[4-(trifluoromethoxy)phenyl]-1H-benzimidazole;
2-(4-chlorobenzyl)-1-cyclobutyl-5-[(3-pyridin-3-ylpyrrolidin-1-yl)carbonyl]-1H-benzimidazole;
1-cyclobutyl-2-pyridin-3-yl-5-[(3-pyridin-3-ylpyrrolidin-1-yl)carbonyl]-1H-benzimidazole;
1-cyclobutyl-2-pyridin-4-yl-5-[(3-pyridin-3-ylpyrrolidin-1-yl)carbonyl]-1H-benzimidazole;
1-(1-methylcyclopropyl)-5-[(3-pyridin-3-ylpyrrolidin-1-yl)carbonyl]-2-[4-(trifluoromethoxy)phenyl]-1H-benzimidazole;
2-phenyl-1-pyridin-3-yl-5-[(3-pyridin-3-ylpyrrolidin-1-yl)carbonyl]-1H-benzimidazole;
2-(2,4-difluorophenyl)-1-pyridin-3-yl-5-[(3-pyridin-3-ylpyrrolidin-1-yl)carbonyl]-1H-benzimidazole;
2-(2,4-dichlorophenyl)-1-pyridin-3-yl-5-[(3-pyridin-3-ylpyrrolidin-1-yl)carbonyl]-1H-benzimidazole;
2-(3,5-dichlorophenyl)-1-pyridin-3-yl-5-[(3-pyridin-3-ylpyrrolidin-1-yl)carbonyl]-1H-benzimidazole;
1-pyridin-3-yl-5-[(3-pyridin-3-ylpyrrolidin-1-yl)carbonyl]-2-[3-(trifluoromethoxy)phenyl]-1H-benzimidazole;
1-pyridin-3-yl-5-[(3-pyridin-3-ylpyrrolidin-1-yl)carbonyl]-2-[4-(trifluoromethoxy)phenyl]-1H-benzimidazole;
2-(4-chlorobenzyl)-1-pyridin-3-yl-5-[(3-pyridin-3-ylpyrrolidin-1-yl)carbonyl]-1H-benzimidazole;
1,2-dipyridin-3-yl-5-[(3-pyridin-3-ylpyrrolidin-1-yl)carbonyl]-1H-benzimidazole;
1-pyridin-3-yl-2-pyridin-4-yl-5-[(3-pyridin-3-ylpyrrolidin-1-yl)carbonyl]-1H-benzimidazole;
2-methyl-1-phenyl-5-[(3-pyridin-3-ylpyrrolidin-1-yl)carbonyl]-1H-benzimidazole;
2-[3,5-bis(trifluoromethyl)phenyl]-1-phenyl-5-[(3-pyridin-3-ylpyrrolidin-1-yl)carbonyl]-1H-benzimidazole;
2-methyl-5-[(3-pyridin-3-ylpyrrolidin-1-yl)carbonyl]-1-[4-(trifluoromethoxy)phenyl]-1H-benzimidazole;
5-[(3-pyridin-3-ylpyrrolidin-1-yl)carbonyl]-1-[4-(trifluoromethoxy)phenyl]-2-(trifluoromethyl)-1H-benzimidazole;
2-isopropyl-5-[(3-pyridin-3-ylpyrrolidin-1-yl)carbonyl]-1-[4-(trifluoromethoxy)phenyl]-1H-benzimidazole;
2-isobutyl-5-[(3-pyridin-3-ylpyrrolidin-1-yl)carbonyl]-1-[4-(trifluoromethoxy)phenyl]-1H-benzimidazole;
2-tert-butyl-5-[(3-pyridin-3-ylpyrrolidin-1-yl)carbonyl]-1-[4-(trifluoromethoxy)phenyl]-1H-benzimidazole;
2-cyclopropyl-5-[(3-pyridin-3-ylpyrrolidin-1-yl)carbonyl]-1-[4-(trifluoromethoxy)phenyl]-1H-benzimidazole;
2-cyclobutyl-5-[(3-pyridin-3-ylpyrrolidin-1-yl)carbonyl]-1-[4-(trifluoromethoxy)phenyl]-1H-benzimidazole;
2-(1-methylcyclopropyl)-5-[(3-pyridin-3-ylpyrrolidin-1-yl)carbonyl]-1-[4-(trifluoromethoxy)phenyl]-1H-benzimidazole;
2-(1-methylcyclobutyl)-5-[(3-pyridin-3-ylpyrrolidin-1-yl)carbonyl]-1-[4-(trifluoromethoxy)phenyl]-1H-benzimidazole;
5-[(3-pyridin-3-ylpyrrolidin-1-yl)carbonyl]-1-[4-(trifluoromethoxy)phenyl]-2-(2,2,2-trifluoro-1-methylethyl)-1H-benzimidazole;
2-(1-phenylethyl)-5-[(3-pyridin-3-ylpyrrolidin-1-yl)carbonyl]-1-[4-(trifluoromethoxy)phenyl]-1H-benzimidazole;
2-phenyl-5-[(3-pyridin-3-ylpyrrolidin-1-yl)carbonyl]-1-[4-(trifluoromethoxy)phenyl]-1H-benzimidazole;
5-[(3-pyridin-3-ylpyrrolidin-1-yl)carbonyl]-1-[4-(trifluoromethoxy)phenyl]-2-[1-(trifluoromethyl)cyclopropyl]-1H-benzimidazole;
2-(1-fluoro-1-methylethyl)-5-[(3-pyridin-3-ylpyrrolidin-1-yl)carbonyl]-1-[4-(trifluoromethoxy)phenyl]-1H-benzimidazole;
2-sec-butyl-5-[(3-pyridin-3-ylpyrrolidin-1-yl)carbonyl]-1-[4-(trifluoromethoxy)phenyl]-1H-benzimidazole;
1-(2,4-dichlorophenyl)-2-isopropyl-5-[(3-pyridin-3-ylpyrrolidin-1-yl)carbonyl]-1H-benzimidazole;
1-(3,5-dichlorophenyl)-2-isopropyl-5-[(3-pyridin-3-ylpyrrolidin-1-yl)carbonyl]-1H-benzimidazole;
2-isopropyl-5-{[3-(5-methylpyridin-3-yl)pyrrolidin-1-yl]carbonyl}-1-[4-(trifluoromethoxy)phenyl]-1H-benzimidazole;
2-isopropyl-5-{[3-(5-fluoropyridin-3-yl)pyrrolidin-1-yl]carbonyl}-1-[4-(trifluoromethoxy)phenyl]-1H-benzimidazole;
2-isopropyl-5-{[3-(5-methoxypyridin-3-yl)pyrrolidin-1-yl]carbonyl}-1-[4-(trifluoromethoxy)phenyl]-1H-benzimidazole;
2-isopropyl-5-{[3-(5-methyl-1,3,4-oxadiazol-2-yl)pyrrolidin-1-yl]carbonyl}-1-[4-(trifluoromethoxy)phenyl]-1H-benzimidazole;
2-isopropyl-5-{[3-(4H-1,2,4-triazol-4-ylmethyl)pyrrolidin-1-yl]carbonyl}-1-[4-(trifluoromethoxy)phenyl]-1H-benzimidazole;
1-({2-isopropyl-1-[4-(trifluoromethoxy)phenyl]-1H-benzimidazol-5-yl}carbonyl)-3-pyridin-3-ylpyrrolidin-3-ol;
1-({2-isopropyl-1-[4-(trifluoromethoxy)phenyl]-1H-benzimidazol-5-yl}carbonyl)-3-(5-methylpyridin-3-yl)pyrrolidin-3-ol;
3-(5-fluoropyridin-3-yl)-1-({2-isopropyl-1-[4-(trifluoromethoxy)phenyl]-1H-benzimidazol-5-yl}carbonyl)pyrrolidin-3-ol;
3-(5-chloropyridin-3-yl)-1-({2-isopropyl-1-[4-(trifluoromethoxy)phenyl]-1H-benzimidazol-5-yl}carbonyl)pyrrolidin-3-ol;
1-({2-isopropyl-1-[4-(trifluoromethoxy)phenyl]-1H-benzimidazol-5-yl}carbonyl)-3-(5-methoxypyridin-3-yl)pyrrolidin-3-ol;
5-[3-hydroxy-1-({2-isopropyl-1-[4-(trifluoromethoxy)phenyl]-1H-benzimidazol-5-yl}carbonyl)pyrrolidin-3-yl]nicotinonitrile;
1-({2-isopropyl-1-[4-(trifluoromethoxy)phenyl]-1H-benzimidazol-5-yl}carbonyl)-3-[5-(trifluoromethyl)pyridin-3-yl]pyrrolidin-3-ol;

1-({2-isopropyl-1-[4-(trifluoromethoxy)phenyl]-1H-benzimidazol-5-yl}carbonyl)-3-(2-methoxypyridin-5-yl)pyrrolidin-3-ol;

5-[(3-fluoro-3-pyridin-3-ylpyrrolidin-1-yl)carbonyl]-2-isopropyl-1-[4-(trifluoromethoxy)phenyl]-1H-benzimidazole;

1-isopropyl-5-[(3-pyrimidin-5-ylpyrrolidin-1-yl)carbonyl]-2-[4-(trifluoromethoxy)phenyl]-1H-benzimidazole;

1-isopropyl-5-{[3-(5-methyl-1,3,4-oxadiazol-2-yl)pyrrolidin-1-yl]carbonyl}-2-[4-(trifluoromethoxy)phenyl]-1H-benzimidazole;

1-({1-isopropyl-2-[4-(trifluoromethoxy)phenyl]-1H-benzimidazol-5-yl}carbonyl)-3-pyridin-3-ylpyrrolidin-3-ol;

5-[(3-pyridin-3-ylpyrrolidin-1-yl)carbonyl]-2-pyrrolidin-1-yl-1-[4-(trifluoromethoxy)phenyl]-1H-benzimidazole;

2-(3,3-difluoropyrrolidin-1-yl)-5-[(3-pyridin-3-ylpyrrolidin-1-yl)carbonyl]-1-[4-(trifluoromethoxy)phenyl]-1H-benzimidazole;

2-morpholin-4-yl-5-[(3-pyridin-3-ylpyrrolidin-1-yl)carbonyl]-1-[4-(trifluoromethoxy)phenyl]-1H-benzimidazole;

1-({1-(1-methylcyclopropyl)-2-[4-(trifluoromethoxy)phenyl]-1H-benzimidazol-5-yl}carbonyl)-3-pyridin-3-ylpyrrolidin-3-ol;

2-({1-(1-methylcyclopropyl)-1-[4-(trifluoromethoxy)phenyl]-1H-benzimidazol-5-yl}carbonyl)-3-pyridin-3-ylpyrrolidin-3-ol;

1-({2-(3,3-difluoropyrrolidin-1-yl)-1-[4-(trifluoromethoxy)phenyl]-1H-benzimidazol-5-yl}carbonyl)-3-pyridin-3-ylpyrrolidin-3-ol; and 3-isopropyl-6-[(3-pyridin-3-ylpyrrolidin-1-yl)carbonyl]-2-[4-(trifluoro methoxy)phenyl]-3H-imidazo[4,5-b]pyridine;

and the pharmaceutically acceptable salts thereof.

16. The compound of claim 1 selected from the group consisting of:

2-isopropyl-5-[(3-pyridin-3-ylpyrrolidin-1-yl)carbonyl]-1-[4-(trifluoromethoxy)phenyl]-1H-benzimidazole;

2-isopropyl-5-{[3-(5-methylpyridin-3-yl)pyrrolidin-1-yl]carbonyl}-1-[4-(trifluoromethoxy)phenyl]-1H-benzimidazole;

1-cyclobutyl-5-[(3-pyridin-3-ylpyrrolidin-1-yl)carbonyl]-2-[4-(trifluoromethoxy)phenyl]-1H-benzimidazole;

1-({1-isopropyl-2-[4-(trifluoromethoxy)phenyl]-1H-benzimidazol-5-yl}carbonyl)-3-pyridin-3-ylpyrrolidin-3-ol;

2-sec-butyl-5-[(3-pyridin-3-ylpyrrolidin-1-yl)carbonyl]-1-[4-(trifluoromethoxy)phenyl]-1H-benzimidazole;

1-isopropyl-5-[(3-pyridin-3-ylpyrrolidin-1-yl)carbonyl]-2-[4-(trifluoromethoxy)phenyl]-1H-benzimidazole;

2-(1-methylcyclopropyl)-5-[(3-pyridin-3-ylpyrrolidin-1-yl)carbonyl]-1-[4-(trifluoromethoxy)phenyl]-1H-benzimidazole;

2-isopropyl-5-{[3-(5-methyl-1,3,4-oxadiazol-2-yl)pyrrolidin-1-yl]carbonyl}-1-[4-(trifluoromethoxy)phenyl]-1H-benzimidazole;

1-({1-(1-methylcyclopropyl)-2-[4-(trifluoromethoxy)phenyl]-1H-benzimidazol-5-yl}carbonyl)-3-pyridin-3-ylpyrrolidin-3-ol;

5-[(3-pyridin-3-ylpyrrolidin-1-yl)carbonyl]-2-pyrrolidin-1-yl-1-[4-(trifluoromethoxy)phenyl]-1H-benzimidazole;

2-morpholin-4-yl-5-[(3-pyridin-3-ylpyrrolidin-1-yl)carbonyl]-1-[4-(trifluoromethoxy)phenyl]-1H-benzimidazole;

1-(2,4-dichlorophenyl)-2-isopropyl-5-[(3-pyridin-3-ylpyrrolidin-1-yl)carbonyl]-1H-benzimidazole;

2-isopropyl-5-{[3-(5-fluoropyridin-3-yl)pyrrolidin-1-yl]carbonyl}-1-[4-(trifluoromethoxy)phenyl]-1H-benzimidazole;

1-cyclopropyl-2-(2,4-dichlorophenyl)-5-[(3-pyridin-3-ylpyrrolidin-1-yl)carbonyl]-1H-benzimidazole;

2-isopropyl-5-{[3-(5-methoxypyridin-3-yl)pyrrolidin-1-yl]carbonyl}-1-[4-(trifluoromethoxy)phenyl]-1H-benzimidazole; and 1-(1-methylcyclopropyl)-5-[(3-pyridin-3-ylpyrrolidin-1-yl)carbonyl]-2-[4-(trifluoromethoxy)phenyl]-1H-benzimidazole;

and the pharmaceutically acceptable salts thereof.

17. A method of treating atherosclerosis comprising administering a therapeutically effective amount of a compound of claim 1 to a patient in need of such treatment.

18. A method for treating pain, comprising administering a therapeutically effective amount of a compound of claim 1 to a patient in need of such treatment.

19. A pharmaceutical composition comprised of a therapeutically effective amount of a compound of claim 1 and a pharmaceutically acceptable carrier, optionally comprised of a therapeutically effective amount of one or more additional active agents.

\* \* \* \* \*